US008449914B2

(12) United States Patent
Andersen et al.

(10) Patent No.: US 8,449,914 B2
(45) Date of Patent: May 28, 2013

(54) CONTROLLED RELEASE CARVEDILOL COMPOSITIONS

(75) Inventors: Christine Andersen, Vedbaek (DK); Gina Fischer, Vaerlose (DK); Daniel Bar-Shalom, Kokkedal (DK); Lillian Slot, Virum (DK); Anne-Marie Lademann, Charlottenlund (DK)

(73) Assignee: Egalet Ltd., Vaerlose (DK)

( * ) Notice: Subject to any disclaimer, the term of this patent is extended or adjusted under 35 U.S.C. 154(b) by 219 days.

(21) Appl. No.: 12/076,105

(22) Filed: Mar. 13, 2008

(65) Prior Publication Data

US 2008/0268057 A1 Oct. 30, 2008

Related U.S. Application Data

(63) Continuation of application No. 10/703,084, filed on Nov. 7, 2003, now abandoned.

(30) Foreign Application Priority Data

Nov. 8, 2002 (DK) .................................. 2002 01725

(51) Int. Cl.
*A61K 9/10* (2006.01)
*A61K 9/12* (2006.01)

(52) U.S. Cl.
USPC ............... 424/486; 424/45; 424/46; 424/436; 424/451; 514/444; 514/411

(58) Field of Classification Search
USPC ................. 424/263, 274, 468, 489, 251, 486, 424/436; 514/411, 908; 548/444
See application file for complete search history.

(56) References Cited

U.S. PATENT DOCUMENTS

| | | | |
|---|---|---|---|
| 4,330,338 A | 5/1982 | Banker | |
| 4,389,393 A | 6/1983 | Schor et al. | |
| 4,503,067 A * | 3/1985 | Wiedemann et al. | 514/411 |
| 4,844,984 A | 7/1989 | Eckenhoff et al. | |
| 4,873,080 A | 10/1989 | Brickl et al. | |
| 4,892,742 A | 1/1990 | Shah | |
| 4,898,733 A | 2/1990 | De Prince et al. | |
| 5,068,112 A | 11/1991 | Samejima et al. | |
| 5,213,808 A | 5/1993 | Bar-Shalom et al. | |
| 5,419,917 A | 5/1995 | Chen et al. | |
| 5,422,123 A | 6/1995 | Conte et al. | |
| 5,741,524 A | 4/1998 | Staniforth et al. | |
| 6,056,968 A | 5/2000 | Gilbert et al. | |
| 6,383,471 B1 * | 5/2002 | Chen et al. | 424/45 |
| 6,488,962 B1 | 12/2002 | Berner et al. | |
| 6,534,085 B1 | 3/2003 | Zeligs | |
| 6,562,375 B1 | 5/2003 | Sako et al. | |
| 6,632,832 B1 * | 10/2003 | Burman et al. | 514/411 |
| 6,709,678 B2 | 3/2004 | Gruber | |
| 6,730,326 B2 * | 5/2004 | Beyer et al. | 424/489 |
| 6,787,156 B1 | 9/2004 | Bar-Shalom | |
| 2001/0036959 A1 * | 11/2001 | Gabel et al. | 514/411 |
| 2001/0036960 A1 * | 11/2001 | Decker et al. | 514/411 |
| 2002/0054911 A1 | 5/2002 | Oh | |
| 2003/0035836 A1 * | 2/2003 | Shanghvi et al. | 424/468 |
| 2003/0118643 A1 * | 6/2003 | Gabel et al. | 424/465 |
| 2004/0151772 A1 | 8/2004 | Andersen et al. | |
| 2004/0234602 A1 | 11/2004 | Fischer et al. | |
| 2004/0253310 A1 | 12/2004 | Fischer et al. | |
| 2005/0019399 A1 | 1/2005 | Fischer et al. | |
| 2005/0019405 A1 | 1/2005 | Bar-Shalom | |
| 2005/0089569 A1 | 4/2005 | Bar-Shalom | |
| 2005/0163837 A1 | 7/2005 | Boehm et al. | |
| 2007/0003617 A1 | 1/2007 | Fischer et al. | |
| 2007/0042044 A1 | 2/2007 | Fischer et al. | |
| 2008/0234352 A1 | 9/2008 | Fischer et al. | |
| 2008/0254122 A1 | 10/2008 | Fischer et al. | |
| 2008/0254123 A1 | 10/2008 | Fischer et al. | |
| 2008/0254124 A1 | 10/2008 | Bar-Shalom | |

FOREIGN PATENT DOCUMENTS

| | | |
|---|---|---|
| DE | 2332484 | 6/1972 |
| DE | 2415490 | 4/1973 |
| EP | 0 893 440 | 1/1999 |
| EP | 0 908 181 | 4/1999 |
| EP | 0 335 560 | 1/2002 |
| EP | 1 371 360 | 5/2005 |
| GB | 2170104 | 7/1986 |
| GB | 2182559 | 5/1987 |
| JP | 60/255719 | 12/1985 |
| JP | 07/1001 | 4/1995 |
| WO | WO 86/04817 | 8/1986 |
| WO | WO 89/09066 | 10/1989 |
| WO | WO 90/08536 | 8/1990 |
| WO | WO 91/04015 | 4/1991 |
| WO | WO 92/09270 | 6/1992 |
| WO | WO 95/22962 | 8/1995 |
| WO | WO-9951208 | * 3/1999 |
| WO | WO 9951208 | * 3/1999 |
| WO | WO 99/24017 | 5/1999 |
| WO | WO 99/44591 | 9/1999 |
| WO | WO 99/51208 | 10/1999 |
| WO | WO 00/32174 | 6/2000 |
| WO | WO 01/35958 | 5/2001 |
| WO | WO 01/51035 | 7/2001 |
| WO | WO 01/51036 | 7/2001 |

(Continued)

OTHER PUBLICATIONS

U.S. Appl. No. 11/915,655, filed Nov. 27, 2007, Bar-Shalom et al.

(Continued)

*Primary Examiner* — Michael G Hartley
*Assistant Examiner* — Jagadishwar Samala
(74) *Attorney, Agent, or Firm* — Carol L. Francis; Bozicevic, Field & Francis, LLP

(57) ABSTRACT

A controlled release pharmaceutical composition for oral use comprising carvedilol. The composition releases carvedilol after oral administration to a mammal, including a human, in such a manner that a prolonged residence of carvedilol is obtained in the circulatory system compared with the known compositions of carvedilol. Furthermore, a composition according to the present invention makes available to the body a suitable plasma concentration of one or both of the enantiomeric species, namely R(+) and/or S(−) carvedilol for obtaining the desired therapeutic effect.

32 Claims, 17 Drawing Sheets

FOREIGN PATENT DOCUMENTS

| | | |
|---|---|---|
| WO | WO 01/74356 | 10/2001 |
| WO | WO 01/74357 | 10/2001 |
| WO | WO 02/065834 | 8/2002 |
| WO | WO 02/092078 | 11/2002 |
| WO | WO 2005/007074 | 1/2005 |
| WO | WO 2005/027878 | 3/2005 |

OTHER PUBLICATIONS

Bravo et al., *J. Pharmaceutical Science*, vol. 5, No. 3, pp. 213-219 (2002).
The Condensed Chemical Dictionary, 9th edition, p. 584 (1977).
Giunchedi et al., *International Journal of Pharmaceutics*, vol. 85, pp. 141-147 (1992).
Hoshi et al., Cellulose and its Derivatives, pp. 24-25 (1992).
Miyazaki et al., "In situ-gelling gellan formulations as vehicles for oral drug delivery," *J. Control Release*, vol. 60, pp. 287-295 (1999).
Rowe et al., *Handbook of Pharmaceutical Excipients*, Pharmaceutical Presse, 4$^{th}$ edition, pp. 257-258 (2003).
www.wikipedia.org, web page on phosphoric acid.
Yamakita et al., *Biol. Pharm. Bull*, vol. 18, No. 10, pp. 1409-1416 (1995).
Office Action issued Oct. 24, 2006 by the Examiner in U.S. Appl. No. 10/703,084 (US 2004/0151772).
Office Action issued Jun. 14, 2007 by the Examiner in U.S. Appl. No. 10/703,084 (US 2004/0151772).
Office Action issued Aug. 3, 2006 by the Examiner in U.S. Appl. No. 10/490,169 (US 2004/0253310).
Office Action issued Mar. 2, 2007 by the Examiner in U.S. Appl. No. 10/490,169 (US 2004/0253310).
Office Action issued Dec. 20, 2007 by the Examiner in U.S. Appl. No. 10/827,521 (US 2005/0019405).
Office Action issued Jul. 25, 2006 by the Examiner in U.S. Appl. No. 10/490,308 (US 2004/0234602).
Office Action issued Mar. 9, 2007 by the Examiner in U.S. Appl. No. 10/490,308 (US 2004/0234602).
Office Action issued Oct. 3, 2006 by the Examiner in U.S. Appl. No. 10/490,170 (US 2005/0019399).
Office Action issued May 9, 2007 by the Examiner in U.S. Appl. No. 10/490,170 (US 2005/0019399).
Office Action issued Oct. 22, 2002 by the Examiner in U.S. Appl. No. 09/647,590.
Office Action issued May 11, 2001 by the Examiner in U.S. Appl. No. 09/647,590.
Office Action issued Jul. 14, 2003 by the Examiner in U.S. Appl. No. 09/647,590.
Office Action issued Jan. 30, 2002 by the Examiner in U.S. Appl. No. 09/647,590.
Office Action issued May 14, 2008 by the Examiner in U.S. Appl. No. 10/845,522 (US 2005/0089569).
Office Action issued Jun. 16, 2006 by the Examiner in U.S. Appl. No. 10/845,522 (US 2005/0089569).
Office Action issued Oct. 27, 2005 by the Examiner in U.S. Appl. No. 10/845,522 (US 2005/0089569).
Office Action issued Jul. 29, 2005 by the Examiner in U.S. Appl. No. 10/845,522 (US 2005/0089569).
Office Action issued Mar. 21, 2007 by the Examiner in U.S. Appl. No. 10/845,522 (US 2005/0089569).
Office Action issued Dec. 23, 2008 by the Examiner in U.S. Appl. No. 10/550,685 (US 2007/0042044).
Office Action issued Dec. 15, 2008 by the Examiner in U.S. Appl. No. 12/213,087 (US 2008/0254124).
Office Action issued Jun. 16, 2009 by the Examiner in U.S. Appl. No. 10/550,453 (US 2007/0042044).
Office Action issued Jan. 13, 2009 by the Examiner in U.S. Appl. No. 10/845,522 (US 2005/0089569).
Office Action issued Jun. 17, 2009 by the Examiner in U.S. Appl. No. 10/550,685 (US 2007/0042044).
Office Action issued on Nov. 10, 2009, by the Examiner in U.S. Appl. No. 10/550,453 (US 2007/0003617).

* cited by examiner

FIG. 13
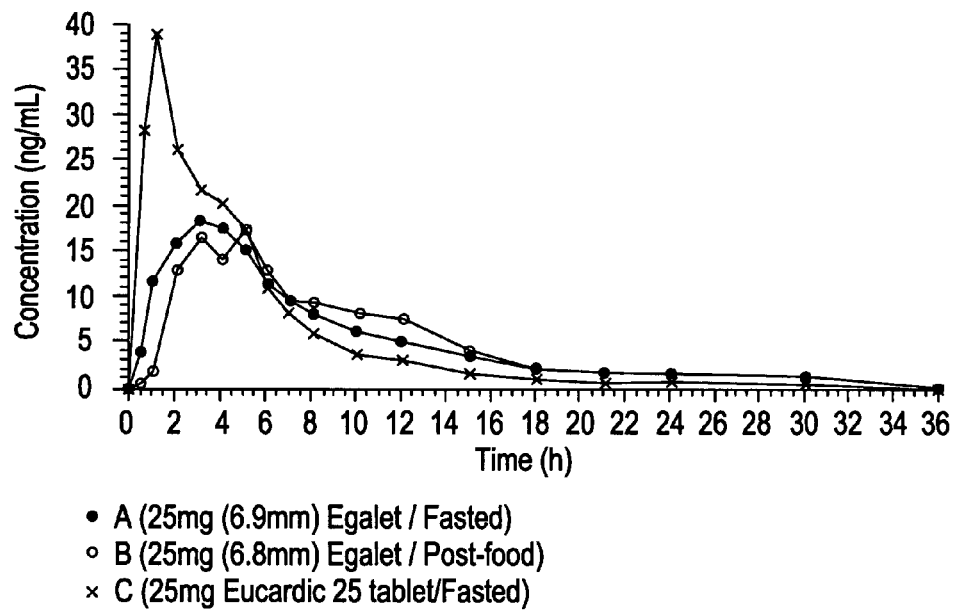
Mean [R(+) Carvedilol] (n=12)
- A (25mg (6.9mm) Egalet / Fasted)
- B (25mg (6.8mm) Egalet / Post-food)
- C (25mg Eucardic 25 tablet/Fasted)
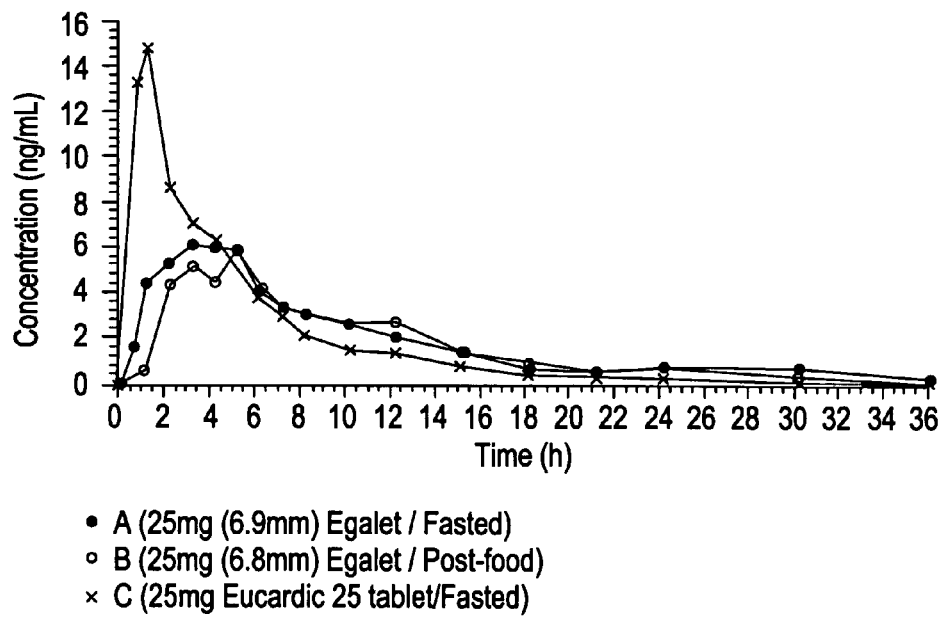
Mean [S(-) Carvedilol] (n=12)
- A (25mg (6.9mm) Egalet / Fasted)
- B (25mg (6.8mm) Egalet / Post-food)
- C (25mg Eucardic 25 tablet/Fasted)

CONTROLLED RELEASE CARVEDILOL COMPOSITIONS

FIELD OF THE INVENTION

The present invention relates to a controlled release pharmaceutical composition for oral use comprising carvedilol. The composition releases carvedilol after oral administration to a mammal, including a human, in such a manner that a prolonged residence of carvedilol is obtained in the circulatory system compared with the known compositions of carvedilol. Furthermore, a composition according to the present invention makes available to the body a suitable plasma concentration of one or both of the enantiomeric species, namely R(+) and/or S(−) carvedilol for obtaining the desired therapeutic effect.

Any suitable controlled release technique may be employed in order to obtain a composition according to the invention. To illustrate the principles of the invention, the present inventors have made use of a matrix technology developed and protected by the same company as to which the present application is assigned to, namely Egalet a/s, Denmark. Accordingly, the present invention also relates to such specific compositions, i.e. a coated matrix composition in which the matrix composition comprises a solid dispersion of i) carvedilol in any form including a prodrug or analog thereof which may at least partially be in an amorphous or crystalline form, ii) a polyethylene glycol and/or a polyethylene oxide having a molecular weight of at least about 20,000 in crystalline and/or amorphous form or a mixture such polymers, and i) optionally, a stabilizing agent, and the composition being designed to release the active substance with a substantially zero order release. The composition is provided with a coating, which is designed to crumble and/or erode upon exposure to an aqueous medium with a rate that is substantially slower than the rate with which the matrix composition erodes. Furthermore, the coating covers the matrix composition in such a manner that only a specific surface area of the matrix composition is subject to erosion in an aqueous medium, i.e. the surface area from which the active substance is release is kept substantially constant during the time period.

The design of such a pharmaceutical composition is based on the finding that it is possible to control the release from such a composition by ensuring that the release predominantly takes place by erosion. Furthermore, the design is based on the finding that it is possible to obtain a composition comprising the active substance in a solid dispersion comprising the active substance at least partially in an amorphous or crystalline form.

WO 00/32174 discloses a combination formulation of carvedilol and hydrochlorthiazide US 2002/0054911 A1 discloses oral dosage forms of carvedilol including controlled release formulations by use of tablet formulations comprising hydroxylmethylcellulose and includes pH sensitive coats on immediate release cores. No clinical data are presented.

WO 01/74357 A1 discloses carvedilol compositions comprising molecular dispersions prepared by dissolving and spray solidifying carvedilol solid solutions. No clinical data are presented.

WO 01/74356 A1 discloses solutions of carvedilol by use of lipophilic adjuvant. No clinical data are presented.

EP 0 893 440 discloses thermodynamically stable modifications of carvedilol. No clinical data are presented.

WO 99/24017 discloses oral formulations comprising carvedilol including enteric coated formulations. No clinical studies are disclosed by use of such formulations.

US 2003/0035836 A1 discloses an oral controlled release formulation comprising carvedilol including clinical data from 12.5 mg controlled formulation as well as dissolution ranges for such formulation.

BACKGROUND OF THE INVENTION

Carvedilol is an active substance, which has very low water solubility. At pH values in the pharmaceutically relevant range of 1 to 8 the solubility of carvedilol in aqueous media is from about 0.01 mg/ml to about 1 mg/ml. The solubility depends on the pH value as carvedilol is a weak base, i.e. the solubility is theoretically larger in an acid medium than in a basic medium. More specifically, it is freely soluble in dimethylsulfoxide; soluble in methylene chloride and methanol; sparingly soluble in 95% ethanol and isopropanol; slightly soluble in ethyl ether; and practically insoluble in water, gastric fluid (simulated, TS, pH1.1) and intestinal fluid (simulated, TS without pancreatin, pH 7.5).

Furthermore, carvedilol is subject to degradation under formation of various generally unwanted degradation products. Carvedilol is normally employed in pharmaceutical compositions in the form of a racemic mixture. It is known that both the R(+) carvedilol and the S(−) carvedilol have a therapeutic effect (cf. below).

Carvedilol may exist in at least two different crystalline forms, normally denoted from I and form II. Form II has a melting point of about 114-115° C., whereas form I has a melting point of about 123-124° C. (EP-A-0 893 440). Form I is described to be thermodynamically stable.

Thus, carvedilol is a substance with solubility and stability problems and, furthermore, such problems normally indicate that the bioavailability is low.

Furthermore, many crystalline, therapeutically active substances have a very limited solubility in aqueous medium such as, e.g., body fluids. It is well known that changing a crystalline compound into its amorphous state will substantially increase the aqueous solubility of the compound.

An amorphous state of an active substance may be obtained by melting the active substance, holding it in the molten state for a certain period of time and then cooling it to an amorphous solid. Such a method is limited to particular active substances that can produce stable amorphous solids that are not degraded by the heating step.

Accordingly, there is a need for novel compositions comprising carvedilol or other active substances having a low water solubility in which the solubility, stability and/or bioavailability is improved.

DISCLOSURE OF THE INVENTION

In accordance with the present invention, compositions of a sparingly soluble, crystalline active substance, e.g. carvedilol, may be converted to and stabilized in its amorphous form as a solid dispersion. The amorphous state and/or the solid dispersion may be stabilized by a stabilizing agent contained in the composition, providing a suitable shelf life of the improved composition. The stabilized composition may also provide an increased solubility of the active substance. The stabilizing agent prevents, inhibits or delays recrystallisation of the less soluble, crystalline form of the active substance.

The invention provides a carvedilol containing pharmaceutical composition for oral use, which provides zero order release, and which at least partially contains carvedilol in amorphous form and/or crystalline form.

Carvedilol has emerged as one of the important and promising drug substances for cardiovascular diseases, especially due to the noticeable improvement of survival rates in patients with chronic cardiac insufficiency. To optimize the treatment, the present inventors have developed a new controlled release composition of carvedilol.

Carvedilol is a therapeutically active compound, which is known to be useful in the treatment of mild to moderate hypertension. Carvedilol is a nonselective beta-adrenoreceptor antagonist and an $alpha_1$-adrenoreceptor antagonist and a vasodilator. It has no intrinsic sympathomimetic activity. The vasodilatory actions of carvedilol result primarily from alpha1-adrenoceptor blockade, whereas the alfa/beta-adrenoceptor blocking activity of carvedilol prevents reflex tachycardia when used in the treatment of hypertension. The multiple actions of carvedilol are responsible for the antihypertensive efficacy of the drug. It also has significant antioxidant properties. As a consequence of its antioxidant action in attenuating oxygen free radical initiated lipid peroxidation, it is also suggested useful in organ protection such as in protection of the kidneys and, in particular, cardioprotection. Carvedilol inhibits the generation of oxygen free radicals and prevents low-density lipoprotein (LDL) oxidation, which, in turn, reduces the uptake of LDL into the coronary vasculature. This antioxidant activity may contribute to carvedilol's cardioprotective effects. In fact, compared with captopril, carvedilol has demonstrated similarly favorable effects on the lipid profiles of hypertensive patients with dyslipidemia.

Like many other classes of medications, beta-blockers can be divided into three distinct groups. The first group consists of nonselective beta-blockers without ancillary properties and includes such drugs as propranolol (Inderal) and timolol maleate (Biocadren).

The second group consists of selective blockers of beta receptor subtypes without ancillary properties. This group includes metoprolol (Lopressor) and atenolol (Tenormin). The third group consists of nonselective beta-blockers that have the ancillary property of vasodilation. Included in this group are labetalol (Normodyne), carvedilol and bucindolol. Bucindolol and carvedilol produce less "inverse agonism" than most other beta-blockers. Inverse agonism is the ability of a beta-blocker to inactivate active state receptors. The beta-blockers with the most inverse agonism, like propranolol, produce the greatest negative chronotropic and inotropic effects. Thus, bucindolol and carvedilol produce relatively fewer negative chronotropic and inotropic effects when compared with beta-blockers like propranolol.

The beta-blocking actions of carvedilol are generally evident in humans within one hour of administration, and the alpha-mediated vasodilatory effects, manifested by decreased peripheral resistance and decreased blood pressure, are evident within about 30 minutes of administration of an IR formulation.

Carvedilol is effective in the treatment of congestive heart failure. Carvedilol is registered for the following indications: hypertension, chronic cardiac insufficiency and angina pectoris as well as for decreasing the risk of sudden death in patients with heart disease. Carvedilol is currently marketed as an immediate release formulation only in 3.125 mg, 6.25 mg, 12.5 mg, 25 mg and 50 mg tablets.

There is a clinical rationale for long-term treatment of hypertension with carvedilol and, accordingly, it would be beneficial to provide a controlled release composition, which enables a dosage frequency of at the most 4 times daily such as, e.g., 3 times daily, 2 times daily or 1 time daily. Furthermore, a controlled composition offers a reduced standard deviation of the concentration of carvedilol in the plasma after administration and thus, gives rise to a more predictable concentration in plasma. Furthermore, a dose regimen with a lower frequency of administration will potentially improve patient compliance.

In the compositions marketed today, carvedilol is present as a racemate having the formula (RS)-1-(9H-carbazol-4-yloxy)-3-[2-(2-methoxyphenoxy)-ethylaminopropan-2-ol.

Carvedilol is rapidly and extensively absorbed following oral administration, with absolute bioavailability of approximately 25% to 35% due to a significant degree of first-pass metabolism. Following oral administration of an immediate release formulation, the apparent mean terminal elimination half-life of carvedilol generally ranges from 7 to 10 hours. Plasma concentrations achieved are proportional to the oral dose administered. When administered with food, the rate of absorption is slowed, as evidenced by a delay in the time to reach peak plasma levels, with no significant difference in extent of bioavailability. Accordingly, it is recommended to take carvedilol with food to minimize the risk of orthostatic hypotension. Carvedilol is extensively metabolized primarily by aromatic ring oxidation and glucuronidation. The oxidative metabolites are further metabolized by conjugation via glucuronidation and sulfation. The metabolites of carvedilol are excreted primarily via the bile into the feces. Demethylation and hydroxylation at the phenol ring produce three active metabolites with b-receptor blocking activity. Based on preclinical studies, the 4'-hydroxyphenyl metabolite is approximately 13 times more potent than carvedilol for beta-blockade. Compared to carvedilol, the three active metabolites exhibit weak vasodilating activity. Plasma concentrations of the active metabolites are about one-tenth of those observed for carvedilol and have pharmacokinetics similar to the parent. Carvedilol undergoes stereoselective first-pass metabolism with plasma levels of R(+)-carvedilol approximately 2 to 3 times higher then S(-)-carvedilol following oral administration in healthy subjects. The mean apparent terminal elimination half-lives for R(+)-carvedilol range from 5 to 9 hours compared with 7 to 11 hours for the S(-)-enantiomer. Carvedilol is subject to the effects of genetic polymorphism with poor metabolizers of debrisoquin (a marker for cytochrome P450 2061 exhibiting 2- to 3-fold higher plasma concentrations of R(+)-carvedilol compared to extensive metabolizers). Carvedilol is more then 96% bound to plasma proteins, primarily with albumin. The plasma-protein binding is independent of concentration over the therapeutic range. Carvedilol is a basic, lipophilic compound with a steady-state volume of distribution of approximately 115 L, indicating substantial distribution into extravascular tissues. Plasma clearance ranges from 500 to 700 mL/min.

Accordingly, the biotransformation of carvedilol in vivo is complex four major metabolites have been identified including 4'-hydroxy carvedilol (4OHC), 5'-hydroxy carvedilol (5OHC), 8-hydroxy carvedilol (8OHC), and O-desmethyl carvedilol (ODMC/M2). The enantiomers exhibit similar alpha-1-blocking activity, but only the S(-) isomer possesses beta-blocking activity.

With respect to the effect of carvedilol, the carvedilol reduces the cardiac workload and improves the ventricular function. In contrast to selective alpha-1-blockers, reflex tachycardia is not produced with carvedilol treatment due to is beta-blocking activity. In addition, the vasodilation effect of the drug and resulting afterload reduction may act to attenuate a worsening of hemodynamics, which is expected from the negative inotropic effect of acute beta-blokade.

Carvedilol possess low solubility in the gastrointestinal fluids and the average flow rate in the lower ileum may be calculated to about 1 mL/min based on the volume reaching the colon of about 1500 ml per day and literature mentioning even lower flows of about 0.5 mL/min. In addition, it is contemplated that the absorption preferable shall take place no more distally than the proximal two thirds of the transverse colon being the part of the absorptive distal part of the GI tract derived from the mid-gut.

Accordingly, a formulation which is less dependent on the amount of water available such as a release system incorporating the carvedilol in a substantial amorphous form may be preferred as dissolution of the carvedilol otherwise may be longer than expected or desired resulting in an unpredictable absorption.

For controlled release delivery of carvedilol consisting of a racemic mixture of the enantiomers with different physiological effect as well as metabolism, it is relevant to identify that the enantiomers is present in the plasma in ratios similar to the ratios obtained from immediate release formulations on which the clinical experience of the drug is based.

It is not predictable whether the actual enantiomers are absorbed with the same rate and to the same extend in the different parts of the gastrointestinal tract. And different enantiomers may also be distributed and eliminated at different rates which again may depend on the dosage strength, release period, location of absorption, etc. When this is taken together with that a controlled delivery formulation may release the enantiomers at different rates, it is not certain that a similar clinical pattern may be obtained from a controlled release formulation as from an immediate formulation.

Accordingly, altering the dosage form may result in unforeseen plasma profiles of the enantiomers and metabolites of the drug, inter alia as a result of the active ingredient being absorbed form different locations of the intestines where the pH and other conditions relevant for the absorption rate and ratio of the individual enantiomers may be unpredictable.

A delivery system where the same relative amount of carvedilol from the dosage form is delivered on the same time—or same location—in the gastrointestinal tract will favor a plasma curve having a shape which is the same over a broad dosage range, such as from 12.6 mg to 50 mg for the total carvedilol as well as for the enantiomers.

The present invention addresses this problem and provides controlled release carvedilol compositions which—after administration to a mammal—give suitable plasma profiles of carvedilol as well as of each of the enantiomers. It is envisaged that administration of carvedilol in the form of a mixture comprising any ratio of the R(+) and S(−) form is important from a therapeutic point of view and, accordingly, the present invention provides compositions comprising carvedilol in any enantiomeric mixture as well as in each of the enantiomeric forms alone.

In the present context, the term "carvedilol" encompasses carvedilol as the racemate; (RS)-1-(9H-carbazol-4-yloxy)-3-[2-(2-methoxyphenoxy)-ethylaminopropan-2-ol as well as the two individual enantiomers: (S)-1-(9H-carbazol-4-yloxy)-3-[2-(2-methoxyphenoxy)-ethylaminopropan-2-ol and (R)-1-(9H-carbazol-4-yloxy)-3-[2-(2-methoxyphenoxy)-ethylaminopropan-2-ol, metabolites of carvedilol including desmethylcarvedilol, pharmaceutically acceptable salts, complexes, polymorphs, solvates or anhydrate thereof, and mixtures thereof.

The term "pharmaceutically acceptable salts" of carvedilol includes alkali metal salts such as, e.g., lithium, sodium or potassium salts, alkaline earth metal salts such as, e.g., calcium and magnesium salts, and salts with organic or inorganic acid like e.g. hydrochloric acid, hydrobromic acid, hydroiodic acid, hydrofluoric acid, nitric acid, sulfuric acid, phosphoric acid, citric acid, formic acid, acetic acid, maleic acid, succinic acid, tartaric acid, methansulphonic acid, toluenesulphonic acid etc.

WO01/35958 A1 discloses carvedilol methanesulfonate, which is hereby included by reference. EP 0 893 440 discloses thermodynamically stable modifications of carvedilol which modifications is hereby incorporated by reference.

The term "solvates" includes hydrates or solvates wherein other solvates than water are involved such as, e.g., organic solvents like chloroform and the like.

Furthermore, carvedilol (or other active substances) may be in any of its crystalline, polymorphous or amorphous forms.

As seen from the tables and figures herein a composition according to the invention gives rise to a delay in the peak concentration of carvedilol or any of its enantiomers after administration of carvedilol in racemic mixture (1:1). However, compared with a marketed carvedilol (not-controlled release) composition, Dimitone® or Dilatrend®, the bioavailability with respect to the area under the plasma concentration curve (AUC) is almost identical. In other words, a prolonged release is obtained and the absorption is complete or almost complete. Considering that the minimum effective dosage is in a range corresponding to a plasma concentration of about 5 ng/ml it is seen from FIG. 2 that a concentration above this limit is maintained for at least 18 hours after administration of a composition according to the invention, while the marketed composition only maintain this concentration for about 12 hours after administration. FIG. 2 also shows that the maximum concentration ($C_{max}$) after administration of a composition of the invention is about 40-45% of the $C_{max}$ after administration of the marketed composition. The dosage given is 55 mg carvedilol in a composition of the invention and 50 mg carvedilol is contained in the marketed composition.

FIG. 3 shows plasma profiles of carvedilol after administration of 25 mg Dilatrend® twice daily and after administration of 50 mg carvedilol in a composition according to the invention. (Carvedilol is in the form of a 1:1 racemic mixture). The AUC for the two different treatments is significantly similar, i.e. the same amount of carvedilol is absorbed. The $C_{max}$ of a composition of the invention is lower than from the marketed composition although the dose is 50 mg (compared to 2×25 mg). This implies that dose related side effects might be significantly reduced or eliminated after administration of a controlled release composition of the invention.

Figure 1:
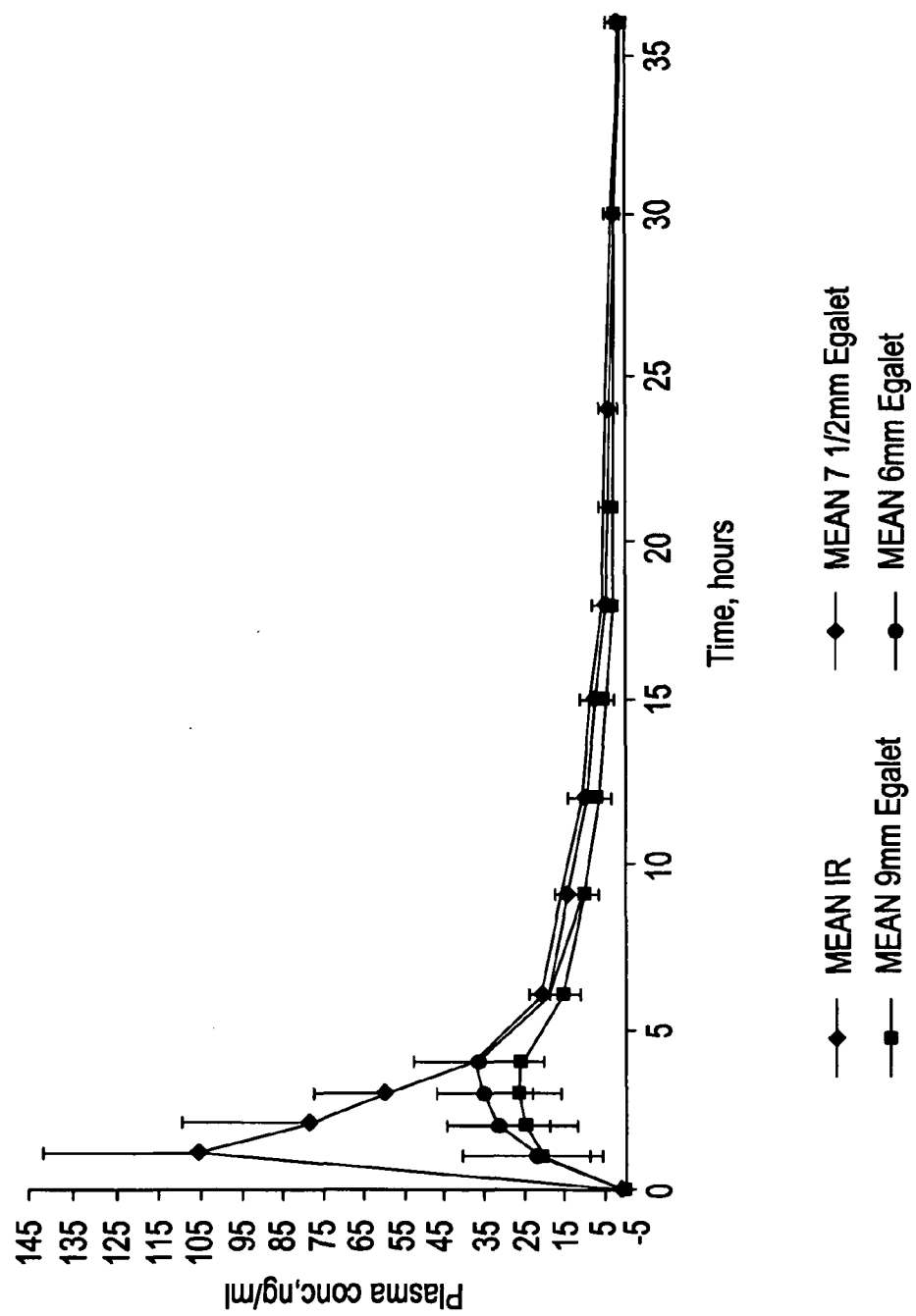

Thus, the present invention relates to:

1. A controlled release pharmaceutical composition for oral use comprising carvedilol at least partly in R(+) form, wherein the release of carvedilol from the composition after administration to a human results in a $t_{max}$ of R(+) carvedilol of from about 1.5 hour to about 8 hours such as, e.g. from about 2 to about 7 hours, from about 2.5 to about 6.5 hours, from about 2.5 to about 6 hours, from about 2.5 to about 5 hours, from about 2.5 to about 4.5 hours from about 2.5 to about 4 hours, from about 2.5 to about 3.5 or from about 2.8 to about 3.5, the $t_{max}$ being determined as described herein as a mean value of results from at least six healthy adults.

2. A controlled release pharmaceutical composition for oral use comprising carvedilol at least partly in R(+) form, wherein the release of carvedilol from the composition after administration to a human results in a ratio of ($t_{max}$ of R(+) carvedilol from the controlled release composition)/($t_{max}$ of R(+) carvedilol from a Dimitone® composition; an immediate release composition) is from about 1.0 to about 5 such as, e.g., from about 1.3 to about 4.5, from about 1.5 to about 4, from about 1.5 to about 3.5, from about 1.5 to about 3.0, from about 1.5 to about 3, the $t_{max}$ being determined as described herein as a mean value of results from at least six healthy adults.

3. A controlled release pharmaceutical composition for oral use comprising carvedilol at least partly in S(−) form, wherein the release of carvedilol from the composition after administration to a human results in a $t_{max}$ of S(−) carvedilol of from about 1.5 hour to about 8 hours such as, e.g. from about 2 to about 7 hours, from about 2.5 to about 6.5 hours, from about 2.8 to about 6 hours, from about 3 to about 5 hours, from about 3 to about 4.5 hours or from about 3 to about 4 hours, the $t_{max}$ being determined as described herein as a mean value of results from at least six healthy adults.

4. A controlled release pharmaceutical composition for oral use comprising carvedilol at least partly in S(−) form, wherein the release of carvedilol from the composition after administration to a human results in a ratio of ($t_{max}$ of S(−) carvedilol from the controlled release composition)/($t_{max}$ of S(−) carvedilol from a Dimitone® composition) is from about 1.5 to about 5 such as, e.g., from about 1.7 to about 4.5, from about 1.8 to about 4, from about 1.9 to about 3.5, from about 2 to about 3.3, from about 2 to about 3, the $t_{max}$ being determined as described herein as a mean value of results from at least six healthy adults.

5. A controlled release pharmaceutical composition for oral use comprising carvedilol at least partly in R(+) form, wherein the release of carvedilol from the composition after administration to a human results in a MRT of R(+) carvedilol which is at least about 6.5 hours such as, e.g. at least about 7 hours or is between from about 6.5 to about 20 hours such as, e.g. from about 7 to about 18 hours, from about 7 to about 17 hours, from about 7 to about 15 hours, from about 7 to about 13 hours, or from about 7 to about 11 hours, the MRT being determined as described herein as a mean value of results from at least six healthy adults.

6. A controlled release pharmaceutical composition for oral use comprising carvedilol at least partly in R(+) form, wherein the release of carvedilol from the composition after administration to a human results in a ratio of (MRT of R(+) carvedilol from the controlled release composition)/(MRT of R(+) carvedilol from a Dimitone® composition) is from about is from about 0.5 to about 5 such as, e.g., from about 0.7 to about 4.5, from about 0.8 to about 4, from about 0.9 to about 3.5, from about 1 to about 3.3, from about 1 to about 3, the MRT being determined as described herein as a mean value of results from at least six healthy adults.

7. A controlled release pharmaceutical composition for oral use comprising carvedilol at least partly in S(−) form, wherein the release of carvedilol from the composition after administration to a human results in a MRT of S(−) carvedilol which is at least about 7 hours such as, e.g. at least about 8 hours or is between from about 7 to about 22 hours such as, e.g. from about 7.5 to about 20 hours, from about 8 to about 19 hours, from about 9 to about 18 hours, from about 9 to about 16 hours from about 9 to about 15 hours, from about 10 to about 16 hours or from about 11 to about 14 hours, the MRT being determined as described herein as a mean value of results from at least six healthy adults.

8. A controlled release pharmaceutical composition for oral use comprising carvedilol at least partly in S(−) form, wherein the release of carvedilol from the composition after administration to a human results in a ratio of (MRT of S(−) carvedilol from the controlled release composition)/(MRT of S(−) carvedilol from a Dimitone® composition) is from about is from about 1.0 to about 5 such as, e.g., from about 1.2 to about 4.5, from about 1.3 to about 4, from about 1.4 to about 3.5, from about 1.5 to about 3.3, from about 1.5 to about 3, the t max being determined as described herein as a mean value of results from at least six healthy adults.

9. A controlled release pharmaceutical composition for oral use comprising carvedilol at least partly in R(+) form, wherein the release of carvedilol from the composition after administration to a human results in a C max which—compared to the results after administration of a Dimitone® composition—is at the most about 90% of the value obtained from a Dimitone® composition such as, e.g. at the most about 85%, at the most about 80%, at the most about 75%, at the most about 70%, at the most about 65%, at the most about 60%, at the most about 55%, at the most about 50% or at the most about 45%, the C max being determined as described herein as a mean value of results from at least six healthy adults.

10. A controlled release pharmaceutical composition for oral use comprising carvedilol at least partly in R(+) form, wherein the release of carvedilol from the composition after administration to a human results in a $C_{max}$ of R(+) carvedilol which—when calculated as a dosage correlated $C_{max}$, $C_{calc}$, (C max in ng/ml)/mg carvedilol in the composition—corresponds to a $C_{calc}$ from about 1.4 to about 0.1 such as, e.g. from about 1.3 to about 0.2, from about 1.3 to about 0.3, from about 1.2 to about 0.35, from about 1.1 to about 0.4, from about 1.0 to about 0.45, from about 0.9 to about 0.4, from about 0.9 to about 0.5, from about 0.8 to about 0.4, or from about 0.8 to about 0.5, the $C_{max}$ being determined as described herein as a mean value of results from at least six healthy adults.

11. A controlled release pharmaceutical composition for oral use comprising carvedilol at least partly in S(−) form, wherein the release of carvedilol from the composition after administration to a human results in a $C_{max}$ which—compared to the results after administration of a Dimitone® composition—is at the most about 90% of the value obtained from a Dimitone® composition such as, e.g. at the most about 85%, at the most about 80%, at the most about 75%, at the most about 70%, at the most about 65%, at the most about 60%, at the most about 55%, at the most about 50%, at the most about 45% or at the most about 40%, the $C_{max}$ being determined as described herein as a mean value of results from at least six healthy adults.

12. A controlled release pharmaceutical composition for oral use comprising carvedilol at least partly in S(−) form, wherein the release of carvedilol from the composition after administration to a human results in a $C_{max}$ of S(−) carvedilol which—when calculated as a dosage correlated $C_{max}$, $C_{calc}$, ($C_{max}$ in ng/ml)/mg carvedilol in the composition—corresponds to a $C_{calc}$ from about 0.6 to about 0.05 such as, e.g. from about 0.55 to about 0.1, from about 0.5 to about 0.15, from about 0.45 to about 0.15, from about 0.4 to about 0.15, or from about 0.35 to about 0.2, the $C_{max}$ being determined as described herein as a mean value of results from at least six healthy adults.

13. A controlled release pharmaceutical composition for oral use comprising carvedilol, wherein the release of carvedilol from the composition after administration to a human results in a $t_{max}$ of carvedilol of from about 1.5 hour to about 8 hours such as, e.g. from about 2 to about 7 hours, from about 2.5 to about 6.5 hours, from about 2.5 to about 6 hours, from about 2.5 to about 5 hours, from about 25 to about 4.5 hours, from about 2.5 to about 4 hours, or from about 2.8 to about 3.5, the $t_{max}$ being determined as described herein as a mean value of results from at least six healthy adults. To avoid a too extended release, $t_{max}$ of a specific embodiment of the invention is not more than 4.75 hours.

14. A controlled release pharmaceutical composition for oral use comprising carvedilol, wherein the release of carvedilol from the composition after administration to a human results in a ratio of ($t_{max}$ of carvedilol from the controlled release composition)/($t_{max}$ of carvedilol from a Dimitone® composition) is from about 1.0 to about 5 such as, e.g., from about 1.2 to about 4.5, from about 1.3 to about 4, from about 1.4 to about 3.5, from about 1.5 to about 3.5, from about 1.5 to about 3.5, or from about 1.5 to about 3.0, the $t_{max}$ being determined as described herein as a mean value of results from at least six healthy adults.

15. A controlled release pharmaceutical composition for oral use comprising carvedilol, wherein the release of carvedilol from the composition after administration to a human results in a MRT which is at least about 5.5 hours such as, e.g. at least about 6 hours or is between from about 5.5 to about 20 hours such as, e.g. from about 6 to about 18 hours, from about 7 to about 17 hours, from about 8 to about 17 hours, from about 8 to about 16 hours, from about 8 to about 15 hours, from about 8 to about 13 hours, or from about 8 to about 12 hours, the MRT being determined as described herein as a mean value of results from at least six healthy adults.

16. A controlled release pharmaceutical composition for oral use comprising carvedilol, wherein the release of carvedilol from the composition after administration to a human results in a ratio of (MRT of carvedilol from the controlled release composition)/(MRT of carvedilol from a Dimitone® composition) is from about 0.7 to about 5 such as, e.g., from about 0.8 to about 4.5, from about 0.9 to about 4, from about 1.0 to about 3.5, from about 1.0 to about 3.3, from about 1.0 to about 3, the MRT being determined as described herein as a mean value of results from at least six healthy adults.

17. A controlled release pharmaceutical composition for oral use comprising carvedilol, wherein the release of carvedilol from the composition after administration to a human results in a $C_{max}$ which—compared to the results after administration of a Dimitone® composition—is at the most about 90% of the value obtained from a Dimitone® composition such as, e.g. at the most about 85%, about 80%, about 75%, about 70%, about 65%, about 60%, about 55%, about 50% or about 45%, the $C_{max}$ being determined as described herein as a mean value of results from at least six healthy adults. To avoid a too extended release, $C_{max}$ of a specific embodiment of the invention is not lower than about 30% of an immediate release carvedilol composition.

18. A controlled release pharmaceutical composition for oral use comprising carvedilol, wherein the release of carvedilol from the composition after administration to a human results in a $C_{max}$ of carvedilol which—when calculated as a dosage correlated $C_{max}$, $C_{calc}$, (C max in ng/ml)/mg carvedilol in the composition—corresponds to a $C_{calc}$ from about 2.0 to about 0.1 such as, e.g. from about 1.9 to about 0.2, from about 1.9 to about 0.3, from about 1.8 to about 0.35, from about 1.7 to about 0.4, from about 1.6 to about 0.45, from about 1.6 to about 0.4, or from about 1.5 to about 0.5, the $C_{max}$ being determined as described herein as a mean value of results from at least six healthy adults.

Furthermore, the $W_{60}$ value, i.e. the time the plasma concentration is at least 50% of the $C_{max}$ value is in a range of from about 3.5 to about 10 hours such as, e.g., from about 4 to about 10 hours from about 4.5 to about 9 hours, from about 5 to about 8.5, from about 5 to about 8 hours, from about 6 to about 8 hours for carvedilol in racemic mixture and/or for the individual enantiomers, respectively, after administration of a composition of the invention.

A controlled release pharmaceutical composition of the invention may contain the carvedilol in the form of a racemic mixture of the R(+) and the S(−) form such as, e.g. a 1:1 mixture of the two enantiomers or wherein the content of the R(+) form is at least about 0.01% mol/mol such as, e.g. at least about 1% mol/mol, at least about 2.5% mol/mol, at least about 5% mol/mol, at least about 10% mol/mol, at least about 15% mol/mol, or from about 0.01% to about 90% mol/mol such as, e.g., from about 0.1 to about 90% mol/mol, from about 1% to about 90% mol/mol, from about 5% to about 90% mol/mol, from about 15% to about 85% mol/mol, from about 20% to about 80% mol/mol, from about 25% to about 75% mol/mol, from about 30% to about 70% mol/mol, from about 40% to about 60% mol/mol based on the molar concentration of total carvedilol.

A controlled release pharmaceutical composition according to the invention may contain the carvedilol in the form of a racemic mixture of the R(+) and the S(−) form such as, e.g. a 1:1 mixture of the two enantiomers or wherein the content of the S(−) form is at least about 10% mol/mol such as, e.g. at least about 15% mol/mol, at least about 20% mol/mol, at least about 25% mol/mol, at least about 30% mol/mol, at least about 35% mol/mol, or from about 10% to about 99.99% mol/mol such as, e.g. from about 10 to about 99% mol/mol, from about 15% to about 97.5% mol/mol, from about 15% to about 95% mol/mol, from about 20% to about 90% mol/mol, from about 25% to about 85% mol/mol, from about 30% to about 80% mol/mol, from about 35% to about 75% mol/mol, from about 40% to about 70% mol/mol, from about 40% to about 60% mol/mol based on the molar concentration of total carvedilol.

The comparisons mentioned above between the controlled release compositions and immediate release formulations are preferable made on the same dosage basis. Thus, the composition may contain the same amount of carvedilol (on a molar basis) or the same total amount of carvedilol on a molar basis (e.g. if the enantiomers are present in different amounts). If the compositions compared contain different amounts of carvedilol, the comparison is made after recalculation of the results taken this difference into account.

A composition according to the Invention may comprise carvedilol in the form of the
R(+) carvedilol e.g. in the pure R(+) form or in the form of the
S(−) carvedilol, i.e. in the pure
S(−) form. In the present context, the term "pure" means a purity of 95% or more.

In general, a pharmaceutical composition according to the present invention is a controlled release pharmaceutical composition for oral use comprising a solid dispersion of
i) carvedilol, which at least partially is in an amorphous or crystalline form,
ii) a polyethylene glycol and/or a polyethylene oxide having a molecular weight of at least about 20,000 in crystalline and/or amorphous form or a mixture such polymers, and
iii) optionally, a stabilizing agent,
and the composition being designed to release the active substance with a substantially zero order release.

In a preferred embodiment, the pharmaceutical composition according to the invention is coated with a coating a coating having at least one opening exposing at the one surface of said matrix. The coating comprises
i) a first cellulose derivative which has thermoplastic properties and which is substantially insoluble in the aqueous medium in which the composition is to be used,
and at least one of
ii) a second cellulose derivative which is soluble or dispersible in water,
iii) a plasticizer, and
iv) a filler.

A pharmaceutical composition according to the invention is designed for controlled release of the active substance into an aqueous medium by erosion of at least one surface of the composition.

As mentioned above, a pharmaceutical composition according to the invention is especially suitable for the delivery of carvedilol, which normally is crystalline and have poor water solubility.

In a preferred embodiment of the invention, carvedilol in the composition is selected from the group consisting of the racemate, (RS)-1-(9H-carbazol-4-yloxy)-3-[2-(2-methoxyphenoxy)-ethylaminopropan-2-ol, the two individual enantiomers; (S)-1-(9H-carbazol-4-yloxy)-3-[2-(2-methoxyphenoxy)-ethylaminopropan-2-ol and (S)-1-(9H-carbazol-4-yloxy)-3-[2-(2-methoxyphenoxy)-ethylaminopropan-2-ol, metabolites of carvedilol including desmethylcarvedilol, pharmaceutically acceptable salts, complexes, solvates and anhydrate thereof, and mixtures thereof.

The active substance is present in any of its crystalline, polymorphous or amorphous forms or mixtures thereof.

The active substance at least partially is present in solid or dissolved form in the dispersion, i.e. some of the active substance may be dissolved in the polymer and/or in the matrix composition.

In the pharmaceutical technology (and in the present context), the term "solid dispersion" also embraces semi-solid dispersions. By the term is understood the finely dispersed distribution of one or more solids, e.g. an active substance like carvedilol, in an inert solid or semi-solid carrier. The active substance may be present in molecular dispersed form, i.e. as a solid solution, in fine crystalline dispersed form, in a glassy amorphous phase or dispersed as a fine amorphous powder. Eutectic mixtures, i.e. crystalline structures of active substances and carriers are also encompassed in the definition of "solid dispersions". Normally, the mean particle size is used to classify dispersed system. A colloidal dispersion is when the dispersed phase has a particle size between about 1 and about 1000 nm and a coarsely dispersion has a mean particle size of at least about 1000 nm and a molecular dispersion has a particle size below about 1 nm. Combinations between the various states are very likely and the most dominating character can be determined by X-ray diffraction spectra or differential thermoanalysis.

In a pharmaceutical composition according to the invention some of the active substance may be present in a molecular dispersion such as, e.g., in the form of a solid or semi-solid solution.

Typically, however, a pharmaceutical composition according to the invention contains the active substance on amorphous form in a colloidal dispersion.

Crystals or crystalline forms of the active substance may at the most partially be present in a composition of the invention. By storage of the composition it is contemplated that some crystallisation may occur—which is acceptable as long as it has no or only minor influence of the pharmaceutical properties of the composition (dissolution data and bioavailability of the composition).

In a preferred aspect of the invention, a composition comprises carvedilol that at least partially is present in amorphous form with a mean particle size of at the most 500 µm such as, e.g., at the most about 300 µm, at the most about 200 µm, at the most about 100 µm. In general, the particle size is in a range of from about 0.01 µm to about 500 µm, from about 0.05 µm to about 500 µm, from about 0.1 µm to about 500 µm, from about 0.5 µm to about 500 µm, about 1 µm to about 500 µm, typically from about 0.5 µm to about 300 µm, more typically from about 1 µm to about 200 µm, especially from about 1 µm to about 100 µm, but particle sizes below 0.01 µm may also be of relevance e.g. in the case of solid solutions or solid colloidal dispersions.

Stabilizing Agent

A pharmaceutical composition according to the invention contains one or more stabilizing agents. The stabilizing agent may serve more than one purpose, it may stabilize the amorphous state of the active substance in the composition in order to avoid, reduce or delay any recrystallization, it may stabilize the active substance or other ingredients towards proteolytic or oxidative degradation or it may have an anti-plasticizing effect. To this end, the inventors have observed that e.g. polyethylene glycol (PEG) 200,000—when heated to about 70° C. tend to form an elongated elastic-like state—and it seem that e.g. addition of certain acidic substances has an anti-plasticizer effect thereon, i.e. a more structured state appears after addition of one or more acid substances.

A stabilizing agent may also contribute to an improved solubility of the active substance. Without being bound to any theory it may be assumed that the stabilizing agent together with the polyethylene glycol and/or the polyethylene oxide and/or any other ingredients contained in the polymer matrix represent the dispersion medium wherein the solubility of the active substance may be higher than in the polyethylene glycol and/or polyethylene oxide. The same may apply with respect to the stability of the amorphous form of the active substance.

Accordingly, a composition according to the inventions may as a stabilizing agent contain a substance, which—together with the polyethylene glycol and/or polyethylene oxide and/or any other ingredients included in the polymer matrix—forms a dispersion medium in which the active substance is contained.

The stabilizing agent for use in a composition of the invention is selected from the group consisting of inorganic acids, inorganic bases, inorganic salts, organic acids or bases and pharmaceutically acceptable salts thereof. The organic acid is a mono-, di-, oligo or polycarboxylic acid such as, e.g. acetic acid, succinic acid, citric acid, tartaric acid, acrylic acid, benzoic acid, malic acid, maleic acid, sorbic acid etc.

The pharmaceutically acceptable salt of an organic acid is e.g. an alkali metal salt or an alkaline earth metal salt such as, e.g. sodium phosphate, sodium dihydrogen phosphate, disodium hydrogen phosphate etc., potassium phosphate, potassium dihydrogen phosphate, potassium hydrogen phosphate etc., calcium phosphate, dicalcium phosphate etc., sodium sulfate, potassium sulfate, calcium sulfate, sodium carbonate, sodium hydrogen carbonate, potassium carbonate, potassium hydrogen carbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate, calcium tartrate, zinc gluconate, zinc sulphate etc.

The inorganic salt may be sodium chloride, potassium chloride, calcium chloride, magnesium chloride etc.

In a preferred embodiment, the stabilizing agent is phosphoric acid such as, e.g., ortho-phosphoric acid.

Citric acid has also a certain stabilizing effect and it may be present in the form of a molecular dispersion and/or in the form of a colloidal dispersion.

Controlled Release

During the last decades many different systems for modifying the release of an active drug substance from a pharmaceutical composition have been developed. Most of them aim at obtaining a zero or a first order release rate of the active substance from the composition. Zero order release rate (i.e. constant release of the active substance with time) seems to be very difficult to obtain from a pharmaceutical composition. The present invention is based on a polymeric matrix composition, which is construed to deliver the active substance in a zero order release manner. The present invention is a further development based on the Applicant's previously described drug delivery systems, see e.g. EP-B-0 406 315, EP-B-0 493 513, EP-B-0 740 310 and WO 99/51208 the disclosure of which is hereby incorporated by reference.

In particular, it has surprisingly been found that it is possible to obtain zero order release from a polymeric matrix composition without any content of a water dispersible or water soluble surface active agent or a mixture of such surface active agents which has at least one domain which is compatible with the polymer in the polymer matrix composition and at least one other domain which is substantially lipophilic and which has a melting point that is lower than the polymer used in the polymeric matrix composition. The presence of such a substance (e.g. like PEG 400 monostearate of PEG 2000 monostearate) has been contemplated to function as a so-called repair medium cf. EP-B-0 406 315. Such a repair medium has a substantially hydrophilic domain, which gives it affinity to the (crystalline) polymeric phase, thereby filling in domains between grains and cracks in the polymer matrix and reducing the water affinity of these domains and in the polymer matrix itself. Water diffusion in the interface between the polymer crystals is thereby substantially eliminated, thus substantially limiting diffusion of water into the composition to the surface layer of the matrix, so that erosion of the composition is predominantly effected by the dissolving action of the aqueous phase on a surface or surfaces of the composition exposed to the aqueous medium. In other words a repair medium seems to prevent the diffusion of water in the polymer matrix composition.

However, the present inventors have found that it is possible to obtain a zero order release from a polymer matrix composition although water may be able to diffuse into the matrix. When water diffuse into the polymer matrix composition a resulting boundary layer (or swelling layer) can be formed at the surface of the matrix composition, which is exposed to the aqueous medium. In general the diffusion of an active substance through such a boundary layer is important for the release of an active substance and, accordingly the thickness of the boundary layer is important for the release rate. However, the present inventors have found that it is possible to eliminate or substantially eliminate the impact of the boundary layer on the release rate of the active substance from a polymer matrix composition buy ensuring that the thickness of the boundary layer is relatively small and/or that the release of the active substance from a polymer matrix composition is governed by erosion of the composition and the diffusion of the active substance through the boundary layer, if any, has no or only a small impact on the overall release rate.

The present inventors have found that when water is allowed to diffuse into a polymer matrix composition zero order release is obtained when the release rate is governed or controlled by erosion of a constant surface area per time unit. In order to ensure that the erosion of the polymer matrix composition is the predominant release mechanism, the inventors have found that it is necessary to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents contained in the polymer matrix composition along this line the present inventors have obtained polymer matrix compositions, which release the active substance by a zero order release mechanism. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

A method for controlling the release of at least one therapeutically, prophylactically and/or diagnostically active substance into an aqueous medium by erosion of at least one surface of a pharmaceutical composition comprising i) a matrix composition comprising a) a substantially water soluble or crystalline polymer or a mixture of substantially water soluble and/or crystalline polymers, b) carvedilol and, optionally, c) one or more pharmaceutically acceptable excipients, and ii) a coating having at least one opening exposing at the one surface of said matrix, the coating comprising a) a first cellulose derivative which has thermoplastic properties and which is substantially insoluble in the aqueous medium in which the composition is to be used, and at least one of b) a second cellulose derivative which is soluble or dispersible in water, c) a plasticizer, and d) a filler, the method comprising adjusting the concentration and/or the nature of the ingredients making up the matrix composition in such a manner that the diffusion rate of the aqueous medium into the matrix composition corresponds to about ±30% such as, e.g. about ±25%, about ±20%, about ±15% or about ±10% of the dissolution rate of the matrix composition so as to obtain a zero order release of at least about 60% w/w such as, e.g. at least about 65% w/w at least about 70% w/w, at least about 75% w/w, at least about 80% w/w, at least about 86% w/w, at least about 90% w/w, at least about 95% w/w or at least about 97 or 98% w/w of the active substance from the pharmaceutical composition when subject to an in vitro dissolution test as described herein.

By use of such a method it is possible already during the developmental work to test various polymer matrix compositions with respect to diffusion rate of water into the composition and to dissolution rate of the polymer matrix composition in an aqueous medium. Based on such results adjustment of e.g. the concentration and/or nature of the individual constituents in the composition may be performed until the diffusion rate balance the dissolution rate. In such a manner, a relatively simple instrument has been provided in order to ensure a zero order release rate from the final composition.

Controlled Release Compositions

As mentioned above, any type of controlled release technology may be employed in order to obtain a composition of the invention. Thus, a composition of the invention may be in the form of a single unit or in the form of multiple units. The unit(s) may be coated with a controlled release coating or they may contain controlled release materials e.g. in the form of matrix materials. A person skilled in the art knows relevant technologies and may find guidance in Remington's Pharmaceutical Science. In the following is a composition according to the invention exemplified as specific kinds of matrix compositions. The invention is, however, not limited thereto.

A number of techniques may be used to obtain controlled release of carvedilol according to the present invention including osmotic systems using osmotic pressure as the driving force for the delivery by comprising a core which is coated with a semipermeable membrane, and a delivery orifice is provide mechanically or by a laser drill. In contact with water, water is imbibed because of the resultant osmotic pressure of the core and the drug is released from the orifice at a controlled rate. Modifications of this technology such as the push-pull osmotic pump may be preferred comprising a bilayer tablet where the upper layer consist osmotic agents and the drug, and the lower layer a polymeric push compartment. The tablet is coated with a semipermeable membrane and a delivery orifice is created. These osmotic systems are known as OROS® from Alza Corporation and, Zer-Os from SDD Drug Delivery Technologies comprising a core containing the drug and gel-forming agents.

Other osmotic system is SCOT® from Andrix Pharmaceuticals

A further aspect of the invention is to provide a system with a more extended absorption time such as the micropump dosage form from Flamel Technologies composed of a high number (thousands) microparticles ranging in size between 50 and 1000 microns and claiming a bioadhesive surface. Each microparticle contains a drug crystal or granule enclosed in a polymer coating that provides release of the drug in a rate controlled by the individual thickness of the coat. Other multiple pellets systems may be utilized for an extended time of absorption due to an observed tendency for such micro particles to be concentrated in the small intestines the before entering the colon and by applying enteric coats to the individual pellets or microsperes. These systems include PPDS® or Pelletized Pulsatile Delivery System, SPDS® a stabilized system for unstable drugs, and Peltab® System from Andrx Pharmaceuticals; Prodas® and IPDAS® from Elan Corporation.

A further system for use according to the invention is the system MacroCap from Biavail Corporations International which utilizes a controlled release pellet system which is based on the coating of pellets containing the drug with specialized polymers and plasticizers to control rate and location of drug release by a pH-activated diffusion adapted to the pH environment of the GI tract. A different system which may be used according to the present invention is the constant surface Consurf® where release is obtained from a swelling matrix tablet allowing a fixed surface to be exposed during the passage through the GI tract.

Additionally, Multiporous Oral Drug Absorption System from Elan Corporation may be utilized where a non-disintegrating, timed-release coating by contact with gastrointestinal fluid is transformed into a semipermeable membrane through with the drug diffuses in a rate-limiting manner. The formulation comprises a core of active drug and excipients and the insoluble polymer coat comprises soluble excipients dissolving during contact with the gastrointestinal fluid leaving channels in the coat for delivery of the drug.

The multilayer tablet system Geomatrix® form Skye Pharma Plc. using modulating layers or barriers to delay interaction of the core with the gastrointestinal fluids is an additional system controlled release system which can be used according to the invention and a zero order release may also be obtained by this system. Other matrix systems include TIMERx® from Penwest Pharmaceuticals Co. Here a slowly eroding core is obtained by interaction of the xantan gum and other gel forming excipients of the formulation with the intestinal fluids Matrix Composition The pharmaceutical composition according to the invention comprises a matrix composition in the form of a solid dispersion comprising
 a) a substantially water soluble or crystalline polymer or a mixture of substantially water soluble and/or crystalline polymers,
 b) carvedilol,
 c) optionally, a stabilizing agent and,
 d) optionally, one or more pharmaceutically acceptable excipients.

Polymers

The substantially water soluble or crystalline polymer or a mixture of substantially water soluble and/or crystalline polymers (in the following denoted: "the polymer") typically comprises a polyglycol, e.g. in the form of a homopolymer and/or a copolymer. Suitable polymers for use in a composition according to the invention are polyethylene glycols and/or block copolymers of ethylene oxide and propylene oxide. Polyethylene glycols or polyethylene oxides which are suitable for use in the matrix composition are those having a molecular weight of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

A particular suitable polyethylene glycol is one, which in itself has a suitable balance between the diffusion rate of water into the polymer and a dissolution rate of the polymer. Suitable examples are polyethylene glycols or polyethylene oxides having a molecular weight of about 35,000 daltons, about 50,000 daltons, about 100,000 daltons, about 200,000 daltons and about 300 daltons.

Typical block copolymers of ethylene oxide and propylene oxide may comprise up to about 30% w/w of the propylene oxide based block, and has a molecular weight of about 5,000 daltons, typically about 5,000 to about 30,000 daltons such as, e.g. from about 8,000 to about 15,000 daltons.

Poloxamers are copolymers or block copolymers and are a range of non-ionic surfactants of ethylene oxide (EO) and propylene oxide (PO). The composition can be an PO block flanked by polyethylene oxide chain, generating two primary functional hydroxyls or a reversed structure, where a central EO block is sandwiched between a polypropylene glycol group, resulting in an overtone of secondary hydroxyl end groups.

In chemical abstracts Diol EO/PO block copolymers are described under the scientific name-hydroxy-hydroxypoly(oxyethylene)poly(oxypropylene)-poly(oxyethylene)-block copolymer in combination with the CAS register number.

Examples of specific block-copolymers suitable for use in a composition of the invention are:

Poloxamer 101, Poloxamer 105, Poloxamer 108, Poloxamer 123, Poloxamer 124, Poloxamer 181, Poloxamer 182, Poloxamer 184, Poloxamer 185, Poloxamer 188, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407.

Poloxamers are sold under the trademark Pluronic® or Lutrol®.

In embodiments where the matrix composition comprises a PEO and a poloxamer the weight ratio (PEO/poloxamer) is in a range from about 10:0.1 to about 0.1:10 such as, e.g., from about 10:1 to about 1:10, from about 5:1 to about 1:5 or from about 3:1 to about 1:3.

Polyethylene glycols (which when the molecular weight is above about 100,000 is denoted polyethylene oxides) are mixtures of condensation polymers of ethylene glycol. The polymers have the general formula $H(OCH_2CH_2)_nOH$ where n is an integer higher than or equal to 4. In general, each PEG is followed by a number, which corresponds to its average molecular weight.

Mixtures of PEG with different average molecular weights can be used in order to obtain a PEG with a desirable average molecular weight. It is important to note that in such cases it is necessary to use the PEG, which have MW closest to the desired molecular weight. The individual amount of the two PEG necessary to obtain a PEG with a desired MW can be calculated from the hydroxyl number and the equation given above.

The polymer may have a melting point, which is above the body temperature of the human or animal in which the composition is to be uses. Thus, the polymer(s) employed in the matrix composition will suitably have a melting point of about 20-120° C. such as, e.g. from about 30 to about 100° C. or from about 40 to about 80° C.

Alternatively to a polymer of a polyglycol type as described above other polymers may be suitable for use in the matrix composition a). Thus, in other embodiments of the invention, the polymer is selected from one or more of the following polymers: water soluble natural polymers such as glucomannan, galactan, glucan, polygalacturonic acid, polyxylane, polygalactomannans, rhanogalacturonan, polyxyloglycan, arabinogalactan, and starch; water soluble polymers such as PVA, PVB, methocel, Eudragit L methyl ester and PHPV; biodegradable polymers such as PHA, and PLA; hydrogels, such as olyacrylic amid, and dextran; copolymers such as polylactic acid with polyglycolic acid; and others such as alginate and pectins including low methylated or methoxylated pectins.

Active Substances

A pharmaceutical composition according to the invention comprises carvedilol. In specific embodiments it may further contain one or more active substances, i.e. substances, which are therapeutically, prophylactically, diagnostically and/or biologically active substance. The term "active substance" as used herein broadly includes any compound, or mixture thereof, that can be delivered from the composition to produce a beneficial result.

In a further aspect, the compositions according to the invention may be combination compositions with the carvedilol together with other active substances such as hydrochlorthiazide, other diuretics, digitalis, ACE inhibitors or other active substances known in the art and in dosages ordinarily used in the combination therapy with carvedilol.

As discussed above, a composition of the present invention is especially suitable for incorporation of crystalline active substances that are convertible into an amorphous form by gentle heating and at the same time have limited water solubility. However, there may be situations where it is desirable to employ other active substance such as, e.g. more water soluble active substance.

Carvedilol and any further active substance present in a composition of the invention can be in various forms, such as uncharged molecules, molecular complexes, crystalline forms, amorphous forms, polymorphous form, solvates, anhydrates, pharmaceutically acceptable salts such as a hydrochloride, hydrobromide, sulfate, laurylate, palmitate, phosphate, nitrite, nitrate, borate, acetate, maleate, tartrate, oleate, and salicylate. For acidic active substance, salts of metals, amines amino acids or organic cations, quaternary ammoniums, can be used. Derivatives of active substances such as esters, ethers and amides which have solubility characteristics suitable for use herein can be used alone or mixed with other drugs. After release of the derivative from the composition it may be converted by enzymes, hydrolysed by body pH or other metabolic processes to the parent drug or to another biologically active form.

A pharmaceutical composition of the invention is designed to release the active substance in a controlled manner such as by a zero order release mechanism. Accordingly, the composition is especially suitable for a controlled release of an active substance. In the present context the term "controlled release" is used to designate a release a desired rate during a predetermined release period. Terms like "modified", "delayed", "sustained", "prolonged", "extended" etc. release are in the present context synonyms to the term "controlled release".

A pharmaceutical composition according to the invention is—due to the possibility of designing the composition in such a manner that i) a zero order release is obtained and ii) a controlled release during a predetermined time period is obtained—suitable for use for water soluble as well as slightly soluble or insoluble active substances i.e. those having a solubility of at the most about 3 mg/ml such as, e.g. at the most about 1 mg/ml, at the most about 0.1 mg/ml, at the most about 0.05 mg/ml such as, e.g. at the most about 0.001 mg/ml in water at ambient temperature. A pharmaceutical composition is also suitable for use when a prolonged release of an active substance (i.e. carvedilol and any further active substance present in the composition) is desired in order to obtain i) a prolonged residence time within the body after administration, ii) a reduced peak plasma concentration in order to avoid peak related side effects, iii) reduced frequency of administration in order e.g. to obtain a better patient compliance, iv) a reduced or substantially eliminated food effect etc.

Carvedilol is suitably present in an amount of up to about 60%, typically up to about 50%, by weight of the matrix composition. An active substance content of about 60% is contemplated to be the maximum content, which still allows for a sufficient content of the polymer and, when relevant, the pharmaceutically acceptable excipient in the composition. The active substance may, on the other hand, be present in the composition in much smaller amounts, depending on the nature and potency of the active substance in question.

Pharmaceutically Acceptable Excipients

The matrix composition may also comprise one or more pharmaceutically acceptable excipients. Apart from the normal function of a pharmaceutically acceptable excipient, the function of the a pharmaceutically acceptable excipient may be to establish a desired balance between on the one hand the diffusion rate of water into the matrix composition and on the other hand the dissolution rate of the matrix composition in an aqueous medium such as, e.g., water. As explained above, a zero order release rate may be obtained if that the diffusion rate of the aqueous medium into the matrix composition corresponds to about ±30% such as, e.g. about ±25%, about ±20%, about ±15% or about ±10% of the dissolution rate of the matrix composition. By the term "zero order release" is meant that the release takes place so as to obtain a zero order release of at least about 60% w/w such as, e.g. at least about 65% w/w, at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

In general a test for diffusion of water into the matrix composition and a test for the dissolution of the matrix composition in an aqueous medium are performed using a matrix composition having the desired shape and being prepared analogous to the matrix composition in the final composition. This means that when the final composition is prepared by e.g. injection moulding then the matrix composition to be tested with respect to diffusion and dissolution behavior is also prepared by injection moulding.

There may be cases where it is not necessary to adjust the matrix composition by adding a pharmaceutically acceptable excipient. Such cases are e.g. when the polymer employed in itself has the desired properties with respect to diffusion of water and dissolution of polymer.

In the experimental section herein examples are given showing that it has been possible to obtain the desired zero order release when a pharmaceutically acceptable excipients has been incorporated into the matrix composition.

Suitable pharmaceutically acceptable excipients may be selected from the group consisting of inorganic acids, inorganic bases, inorganic salts, organic acids or bases and pharmaceutically acceptable salts thereof, saccharides, oligosaccharides, polysaccharides, and cellulose and cellulose derivatives.

Alternatively or additionally, a suitable pharmaceutically acceptable excipient is a mono-, di-, oligo or polycarboxylic acid such as, e.g. acetic acid, succinic acid, citric acid, tartaric acid, acrylic acid, benzoic acid, malic acid, maleic acid, sorbic acid etc.

Suitable pharmaceutically acceptable salts of an organic acid is e.g. an alkali metal salt or an alkaline earth metal salt such as, e.g. sodium phosphate, sodium dihydrogen phosphate, disodium hydrogen phosphate etc., potassium phosphate, potassium dihydrogen phosphate, potassium hydrogen phosphate etc., calcium phosphate, dicalcium phosphate etc., sodium sulfate, potassium sulfate, calcium sulfate, sodium carbonate, sodium hydrogen carbonate, potassium carbonate, potassium hydrogen carbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate, calcium tartrate, zinc gluconate, zinc sulphate etc.

A suitable inorganic salt for use in a matrix composition of the invention is sodium chloride, potassium chloride, calcium chloride, magnesium chloride etc.

Furthermore, a suitable pharmaceutically acceptable excipient for use in a matrix composition of the invention may be selected from the group consisting of fillers, diluents, disintegrants, glidants, pH-adjusting agents, viscosity adjusting agents, solubility increasing or decreasing agents, osmotically active agents and solvents.

Examples of such excipients are glucose and other monosaccharides, lactose, sucrose, fructose and other disaccharides, dextrin, dextran or other polysaccharides, amylose, xylan, galactose, cellulose and cellulose derivatives such as, e.g. microcrystalline cellulose, methyl cellulose, ethyl cellulose, ethylhydroxyethyl cellulose, ethylmethylcellulose, hydroxyethylcellulose, hydroxyethylmethyl cellulose, carboxymethyl cellulose, hydroxypropyl cellulose, hydroxymethylpropyl cellulose, hydroxypropylmethyl cellulose etc., kaolin, bentonit, mannitol, sorbitol, inositol, starch, acacia, alginic acid, sodium alginate, calcium alginate, gelatine, dextrose, molasses, extract of Irish moss, panwar gum, ghatti gum, mucilage of isapol husk, veegum, sodium starch glycollate, magnesium stearate, calcium stearate, stearic acid, talc, titanium dioxide, silicium dioxide, clays, croscarmellose, gums, agar etc.

Other Ingredients in the Matrix Composition

The matrix composition may also contain other excipients as well, e.g. in order to improve the technical properties of the matrix composition so that it may be easier to produce to reduce stickiness etc.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate, starch, gelatine, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone or mixtures thereof; lubricants such as talc, magnesium stearate, calcium stearate, stearic acid, hydrogenated vegetable oils, sodium benzoate, sodium chloride, leucine, carbowax 4000, magnesium lauryl sulfate, colloidal silicon dioxide and mixtures thereof; disintegrants such as starches, clays, cellulose derivatives including crosscarmellose, gums, aligns, various combinations of hydrogen carbonates with weak acids (e.g. sodium hydrogen carbonate/tartaric acid or citric acid) crosprovidone, sodium starch glycolate, agar, cation exchange resins, citrus pulp, veegum HV, natural sponge, bentonite or mixtures thereof; volatile solvents such as alcohols, including aqueous alcohols, petroleum benzine, acetone, ether or mixtures thereof; plasticizers such as sorbitol and glycerine; and others such as cocoa butter, polyethylene glycols, e.g. with a molecular weight of about 1,000-500,000 daltons, typically about 1,000-100,000 daltons, more typically 1,000-50,000 daltons, especially about 1,000-10,000 daltons, in particular about 1,500-5,000 daltons, and mixtures thereof, hydrogenated vegetable oils, glycerinated gelatine or mixtures thereof.

The matrix composition may in addition include a cellulose derivative, e.g. a cellulose derivative selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose. Of these cellulose derivatives, hydroxypropylmethylcellulose and methylcellulose are preferred for incorporation in the matrix composition.

Furthermore, the matrix composition may comprise one or more agents selected from the group consisting of sweetening agents, flavouring agents and colouring agents, in order to provide an elegant and palatable preparation. Examples of colouring agents are water soluble FD&C dyes and mixtures thereof with corresponding lakes and direct compression sugars such as Di-Pac from Amstar. In addition, coloured dye migration inhibitors such as tragacanth, acacia or attapulgite talc may be added.

Examples of suitable fillers are also dextrin, sucralfate, calcium hydroxyl-apatite, calcium phosphates and fatty acid salts such as magnesium stearate.

The filler may be added in an amount so that the combination of the filler and the active substance comprises up to about 60%, typically up to about 50%, by weight of the first composition.

In order to soften the carrier system, plasticzisers such as beta-naptyl salicylat, nitrobenzene, and carbondisulphide may be used. Other plasticzisers known in the art are also suitable, and for hydrophobic polymers dioctyl phthalate is suitable due to compatibility with hydrophilic medicaments. Phthalyl glycolate is also very suitable in connection with hydrophilic medicaments.

Preferred anti-oxidative agents include TPGS due to surfactant properties, citric acid, tartaric acid, and ascorbic acid. However, other anti-oxidative agents known in the art may be used according to the present invention. Suitable antioxidants for use includes beta-caroten (a vitamin A precursor), ascorbic acid, ascorbyl palmitate, butylated hydroxyanisole, butylated hydroxytoluene, hypophosphorous acid, monothioglycerol, potassium metabisulfite, sodium metabisulfite, propyl gallate, sodium formaldehyde sulfoxylate, sodium thiosulfate, sulfur dioxide, tocopherol, tocopherol acetate, tocopherol hemisuccinate, TPGS or other tocopherol derivatives, sulfides, phosphine etc. Other suitable antioxidants are described herein.

A pharmaceutical composition according to the invention may further comprise one or more pharmaceutically acceptable excipients that may impart the release of the active substance e.g. in order to ensure that the release is substantially pH dependent or pH independent. In some situations it is advantageous to avoid release of the active substance e.g. in the stomach after oral administration or it may be desired to target the release to a specific part of the gastrointestinal tract. In these cases, a pH dependent release (due to the pH differences in the gastrointestinal tract) may be desired. In WO 99/51208, the Applicant describes suitable materials that can be used in order to obtain a pH dependent release. Such materials may be included in a composition according to the invention (normally in the polymer matrix) and are preferably selected from materials conventionally used in the pharmaceutical industry to produce enteric coatings. A number of different types of compounds suitable for use as enteric coatings are known in the art; see e.g. *Remington's Pharmaceutical Sciences*, 18$^{th}$ Edition, 1990. Release modifiers may in particular be selected from one of three general classes, namely cellulose derivatives, methacrylic acid polymers and modified gelatine compounds. Preferred release modifiers include cellulose acetate phthalate, polyvinyl acetate phthalate, hydroxypropyl methylcellulose phthalate and hydroxypropyl methylcellulose acetate succinate, as well as methacrylic acid copolymers. Modified gelatine compounds include gelatine treated with e.g. formaldehyde or glutaraldehyde.

Examples of commercially available polymers suitable for use in order to obtain a pH dependent release are EUDRAGIT® L and EUDRAGIT® S, available from Röhm GmbH, Germany, and enteric coating agents available from Shin-Etsu Chemical Co., Japan. Such a material will typically be present in the composition (especially in the polymer matrix) in an amount of about 0.1-10%, based on the weight of the matrix, preferably about 0.5-4%, e.g. about 1-3%, such as about 1.5-2.0%. If desired, a suitable mixture of such material may be used in order to obtain a desired release profile in any given composition The material for pH dependent release may function to regulate or contribute to control the erosion of the matrix within a pH range of from about 2 to about 7, this means that the material is one which, due to its pH-dependent solubility, provides the matrix with different degrees of erosion at different pH values within this range. Typically, the material is typically soluble above a given pH in the range of from about 5 to about 7, e.g. a pH of about 5.0, 5.5, 6.0, 6.5 or 7.0, but substantially insoluble at lower pH values.

In an interesting embodiment, the composition is one wherein release of the active substance is adapted so that the release rate in an in vitro dissolution method corresponding to the environment of the human stomach with respect to peristaltic movements and pH as described below is not substantially greater than the release rate of the active substance in an in vitro dissolution method corresponding to the environment of the human intestines with respect to peristaltic movements and pH as described below.

In another embodiment, the composition of the invention will be adapted to compensate for differential absorption in the gastrointestinal tract or to provide different rates of release of the active substance in the small intestine and in the large intestine, e.g. by varying the concentration of the release modifier or the active ingredient in different zones of the matrix. The exact release profile provided by any given matrix in a delivery device of the invention will be dependent on the nature of the matrix, including the type and amount of crystalline polymer, surface active agent and release modifier, as well as the nature and amount of the active ingredient in the matrix and the characteristics of a possible coating. However, by adjusting in particular the concentration of the release modifier and the active ingredient, and using routine testing of appropriate variations in vitro and in vivo, a person skilled in the art will readily be able to arrive at delivery systems that provide a desired release profile for a given active substance under a given set of circumstances.

For example, for obtaining a pharmaceutical composition with a first release rate in the small intestine and a second release rate in the large intestine (the small intestine typically having a slightly higher pH value than the large intestine, i.e. normally about 7.2 and 6.9, respectively), a release modifier which is soluble at a pH of from about 7.0 or 7.1, but which is substantially insoluble or at least substantially less soluble at pH values below 7.0, may be chosen. In this case, the delivery system will comprise at least one first zone with a first concentration of the release modifier and optionally at least one second zone with a second concentration of the release modifier. An example of a suitable release modifier for this purpose is EUDRAGIT® S, available from Röhm GmbH, Germany.

The geometric form of the composition is important for the obtainment of the above-mentioned controlled zero order. Thus, in a preferred version of the invention, the pharmaceutical composition of the invention has a geometric shape, which enables a substantially constant surface area to become exposed during erosion of the matrix.

The specific shape (length of formulation) and exposed area (open ends of the formulation) may be adapted according to the release rate from the specific matrix formulation in order to get the most optimal release period in vitro and in vivo. If the absorption time is without desired limits by a give formulation, the specific shape may change. On the other side when a given release time is obtained resulting in a desired absorption rate, other strength can be obtained by decreasing or increasing the diameter of the formulation by use of the same matrix formulation and thereby keep the overall release time. Due to the zero order release pattern, the same fraction will be released on the same time points. This will result in very accurate dose linearity between the different dosage strengths.

It is also possible to obtain a substantial identical release pattern and thereby absorption pattern even with different matrix formulations as long as the shape of the formulation is correlated to obtain similar total release times with the formulations according to the present invention. In the present context a release pattern by use of a 6 mm citric acid formulation is similar to release pattern of a 6.8 mm long formulation comprising the same volume of matrix.

Coating

The pharmaceutical composition may thus have the shape of a cylindrical rod, which is provided with a coating, which is substantially insoluble in and impermeable to fluids such as body fluids during the intended release period, the coating having an opening at one or both ends. Polymers useful as coatings are preferably those, which are possible to process by extrusion, solution or in the form of a dispersion. Most preferred are those, which are available in a food grade or a pharmaceutical grade quality. Examples of such polymers are cellulose acetate, polyamide, polyethylene, polyethylene terephthalate, polypropylene polyurethane, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA), styrene-butadienestyrene (SBS) and styrene-isoprenestyrene (SIS).

The coating may further comprise any of the above-mentioned matrix materials in a form, which erodes at a substantially slower rate than the rest of the matrix. The coating may thus comprise a matrix of one or more substantially water soluble crystalline polymers and, optionally, a non-ionic emulsifier, the coating being one which is eroded in the aqueous phase at a substantially slower rate than the matrix composition comprising the active substance, whereby a substantially constant area of the matrix composition comprising the active substance is exposed during erosion of the matrix composition, and whereby the coating is substantially eroded upon erosion of the matrix composition comprising the active substance. Such a coating will be designed so that its longitudinal erosion rate is substantially the same as the longitudinal erosion rate of the matrix, whereby the matrix and the coating will erode longitudinally towards the centre of the composition at substantially the same rate. Thus, when the matrix composition has been completely eroded by the aqueous medium, the coating will also be substantially completely eroded. A matrix composition having such a coating has the obvious advantage of being completely biodegraded upon release of the active substance. Such a coating will typically be a combination of a polyethylene glycol and a mixture of, for example, polyethylene glycol 400 monostearate or another non-ionic emulsifier, and may also include a filler. The content of the mixture of non-ionic emulsifiers and the filler in the coating will be determined in each particular case according to the characteristics, e.g. erosion rate and size, of the matrix comprising the active substance.

In an embodiment of the invention, the coating is one, which disintegrates or crumbles after erosion of the matrix. A coating of this type would remain intact as long as it was supported by the matrix containing the active substance, but it would lack the ability to remain intact after erosion of the matrix, whereby it would then disintegrate or crumble, so that it would not remain in e.g. a human or animal for any significant amount of time after the complete erosion of the matrix and the release of the active substance.

The coating may also be an enteric coating employing methacrylates, a co-polymer of methacrylate-galactomannan etc.

In an interesting embodiment, the controlled release composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled. Coatings of this type are described in WO 95/22962, to which reference is made and which is incorporated herein by reference. These coatings comprise:

(a) a first cellulose derivative which has thermoplastic properties and which is substantially insoluble in the aqueous medium in which the composition is to be used, e.g. an ethylcellulose such as ethylcellulose having an ethoxyl content in the range of 44.5-52.5%, or cellulose acetate, cellulose propionate or cellulose nitrate;

and at least one of:

(b) a second cellulose derivative which is soluble or dispersible in water, e.g. a cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;

(c) a plasticizer, e.g. selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils; or a non-ionic surfactant; and (d) a filler, e.g. selected from conventional tablet or capsule excipients such as diluents, binders, lubricants and disintegrants.

The use of a plasticizer will often be desirable in order to improve the processability of the ethylcellulose or the first cellulose derivative. The plasticizer may also be a non-ionic surfactant, e.g. a non-ionic surfactant selected from the group consisting of diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters; nitrobenzene, carbon disulfide, β-naphtyl salicylate, phthalyl glycolate, dioctyl phthalate.

Other suitable plasticizers appear from EP-B-0 746 310 to which reference is made and which is hereby incorporated by reference.

A coating of this type may in addition further comprise a release modifier of the type described above, so that the coating is provided with an erosion profile similar to that of the matrix composition in terms of the relative rate of erosion in the stomach and the intestines, respectively. In this case, it may be advantageous to incorporate a somewhat higher concentration of the release modifier in the coating than the concentration of release modifier in the matrix, so as to ensure that the coating does not erode in the stomach at a faster rate than the matrix.

The first cellulose derivative is typically present in a concentration of at the most 99.9% w/w. Normally, the concentration is at least 25% w/w such as, e.g., from about 25% to about 99.9% w/w, from about 30% to about 90% w/w, from about 40% to about 85% w/w, from about 50% to about 85% w/w or from about 55 to about 85% w/w.

The second cellulose derivative, if present, is normally present in a concentration of at the most 50% w/w such as, e.g., at the most about 40% w/w, at the most about 30% w/w, at the most about 20% w/w or at the most about 10% w/w.

A plasticizer, if present, is normally present in a concentration of at least about 0.1% w/w such as, e.g., from about 0.1% to about 50% w/w, from about 1% to about 40% w/w, from about 2% to about 30% w/w or from about 5% to about 25% w/w.

If a filler is present it is normally present in a concentration of at the most 50% w/w such as, e.g., at the most about 40% w/w, at the most about 30% w/w, at the most about 20% w/w or at the most about 10% w/w.

Pharmaceutical Composition

As mentioned above a pharmaceutical composition according to the invention is a coated matrix composition from which the active substance is released in by a zero order release mechanism.

A composition according to the invention containing a drug substance is typically for oral administration and may be in the form of a tablet or a capsule or in the form of a multiple unit dosage form. Due to the possibility of controlling the release rate of the active substance the composition may be adapted to decrease the daily oral administration of 2 or 3 times daily to 1 and 2 respectively, and for the substitution of carvedilol given once daily, the controlled release formulation may have advantages in the form of decreased side effects such as dizziness and a prolonged effect during the day. Especially for the patients treated for heart failure, high peak concentrations should be avoided. In the treatment of hypertension, the controlled release may reduce fluctuations during the day, which is known to be an important feature in the development of organ damage even though the mean blood pressure is reduced. Accordingly, the technology provide compositions for administration only once or twice daily being more convenient for the patients as well as reducing side effects and possible increasing therapeutic effect. In the present context the term "once daily" is intended to mean that it is only necessary to administer the pharmaceutical composition once a day in order to obtain a suitable therapeutic and/or prophylactic response; however, any administration may comprise co-administration of more than one dosage unit, such as, e.g. 2-4 dosage units if the amount of active substance required may not be formulated in only one composition or if a composition of a smaller size is preferred.

A composition of the invention is especially suitable for administration at bed time so that it is effective during night and at early morning hours.

The dosage of the active substance depends on the particular substance, the age, weight condition etc. of the human or animal that will be treated with the composition etc. All such factors are well known to a person skilled in the art.

The controlled release of the active substance is caused substantially by erosion at a constant rate of a surface or surfaces of the first composition The rate at which the active substance is released from the matrix is a predetermined rate, i.e. a rate, which is controllable over a certain period of time. The release rate required in each particular instance may inter all depend on the amount of active substance to be released for it to exert the desired effect, as well as on the overall dosage of the active substance contained in the matrix. The substance of which the matrix is composed and the distribution of the active substance in the matrix may therefore be selected according to one or more of these criteria to ensure the desired level of release of the active substance.

Due to the controlled release of the active substance obtainable from the pharmaceutical composition of the invention, it is possible to obtain a substantially constant rate of release of the active substance over a specific period of time, corresponding to the dosage necessary for the treatment in question, so that adherence to a strict dosage regimen, e.g. requiring administration of a drug at set intervals up to several times a day, may be dispensed with.

Furthermore, it is possible to include two or more different active substances in the pharmaceutical composition of the invention, and the two or more different active substances may be adapted to be released at different concentrations and/or intervals, thus making it easier for patients to follow a prescribed regimen.

An additional advantage of a pharmaceutical composition of the invention, compared to other known controlled release compositions, is that it may be produced by relatively simple and inexpensive methods.

Furthermore, a pharmaceutical composition according to the invention allows for the incorporation of high concentrations of the active substance relative to the size of the delivery system. This is obviously a great advantage, notably when the composition is to be used for the delivery of a therapeutically, prophylactically and/or diagnostically active substance, since it allows for the delivery of the required amount of the active substance without the size of the composition being unnecessarily large. In addition, sparingly soluble or non-soluble active substances may be readily incorporated into a composition of the invention. A composition of the invention may thus be used for the delivery of, for example, sparingly soluble or non-soluble pharmaceutical powders which can otherwise be difficult to administer.

As mentioned above, the release of the active substance from the pharmaceutical composition corresponds to a substantially zero order release determined by in vitro dissolution test according to USP. The substantially zero order release is obtained in a time period of at least 1 hours such as, e.g. at least 2 hours, at least 3 hours, at least 4 hours or at least 5 hours, or in a time period of at least 5 hours such as, e.g. at least 6 hours, at least 7 hours, at least 8 hours, at least 9 hours or at least 10 hours.

In the experimental section herein examples are given on suitable carvedilol containing compositions according to the invention.

Multiple Units Composition

The pharmaceutical composition according to the invention may furthermore be used in the preparation of a multiple units pharmaceutical composition, e.g. in the form of a capsule or tablet. A multiple units pharmaceutical composition is a composition, which comprises a multiplicity of individual units in such a form that the individual units will be made available upon disintegration of the composition, typically a capsule or tablet, in the stomach of humans or animals ingesting said composition. Thus, in this case, at least some of the individual units in said multiple units pharmaceutical composition will consist of the composition of the invention, the individual units being of a size, which allows them to be incorporated into such a composition.

Preparation

A composition of the invention may be produced by various methods which are either known per se in the pharmaceutical industry or which, for example, are used in the production of polymer-based materials, depending upon the desired embodiment and the materials employed in the composition in question. As mentioned above, one advantage of the composition according to the invention is that it may be produced by methods, which are relatively simple and inexpensive.

A pharmaceutical composition may be produced by, for example, co-extrusion of the coating with the matrix composition and the active substance, extrusion and dip coating, injection moulding and dip coating, or by extrusion or injection moulding and solvent coating by spraying or dipping.

For further details reference is made to the experimental section herein.

OTHER ASPECTS OF THE INVENTION

As it appears from the appended claims herein, the invention also relates to a method for treatment of a subject with a composition according to the invention etc. To this end all details and particulars described above under the composition aspect applies mutatis mutandi to the method and other aspects.

The invention is further illustrated in the following non-limiting examples and in the accompanying drawing in which FIG. 1 shows a graphic representation of the data from Pilot study IV. The first two arms were randomized, testing carvedilol immediate release 50 mg and carvedilol Egalet® 50 mg, round shape. The last two arms were randomized comparing round 7½ mm and round 6 mm Egalet®, n=10.

Figure 2:
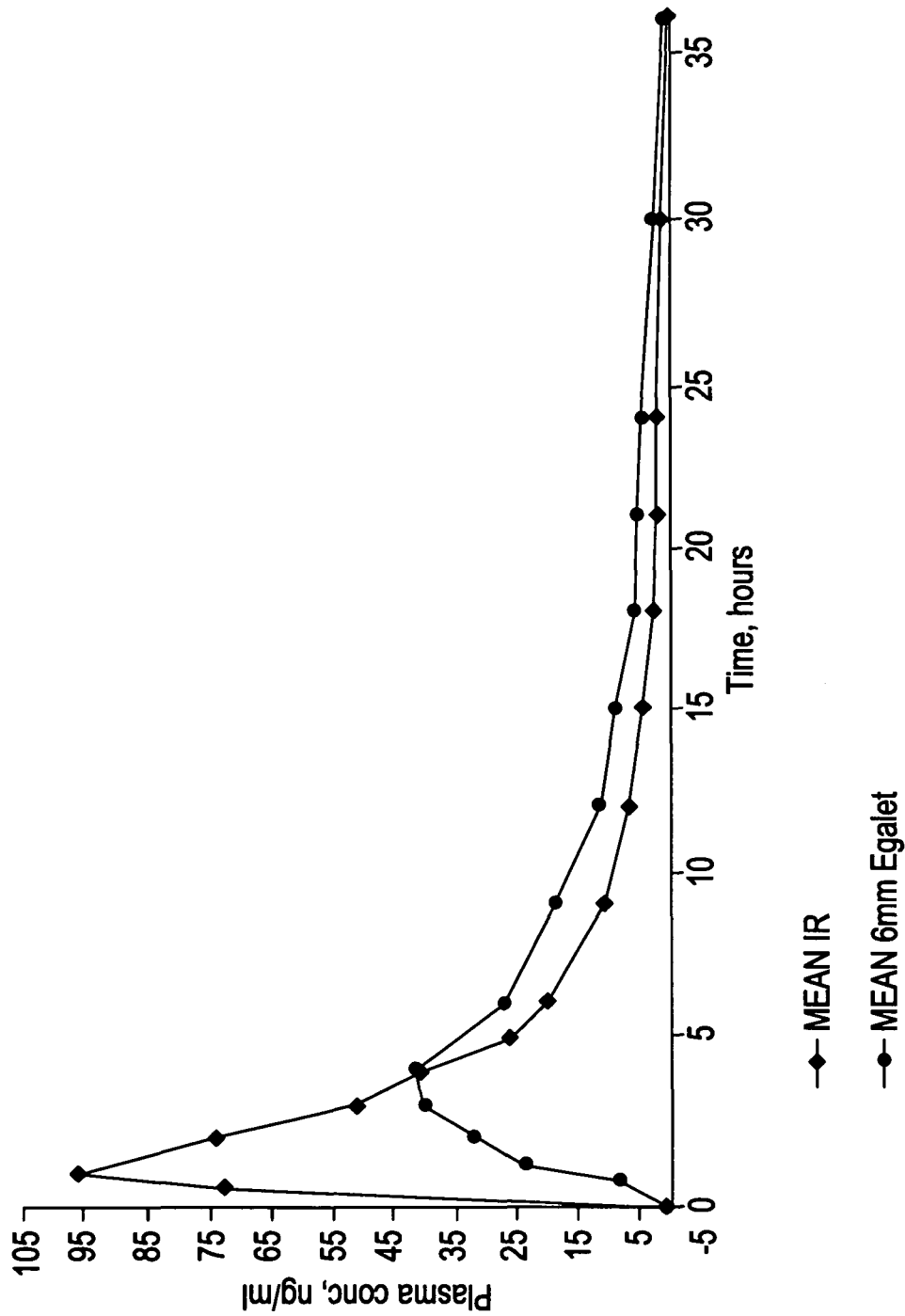

FIG. 2 shows the plasma concentration vs. time for pilot study II in which carvedilol 50 mg immediate release and Egalet® 6 mm, oval shape, 50 mg was tested in 10 subjects.

Figure 3:
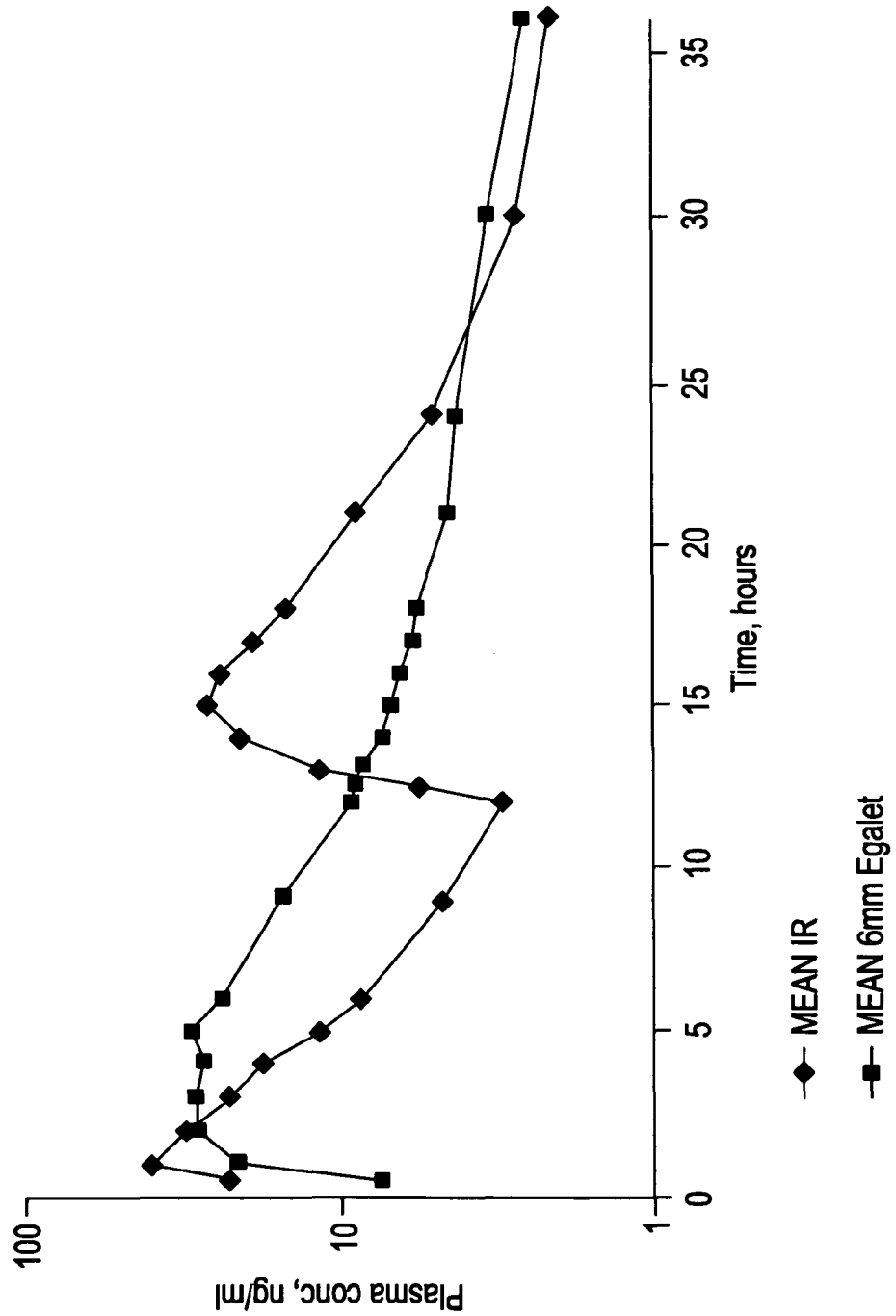

FIG. 3 shows the plasma concentration vs. time for pilot study III in which carvedilol 25 mg immediate release b.i.d. and Egalet® 6 mm, oval shape, 50 mg was tested in 10 subjects.

Figure 4:
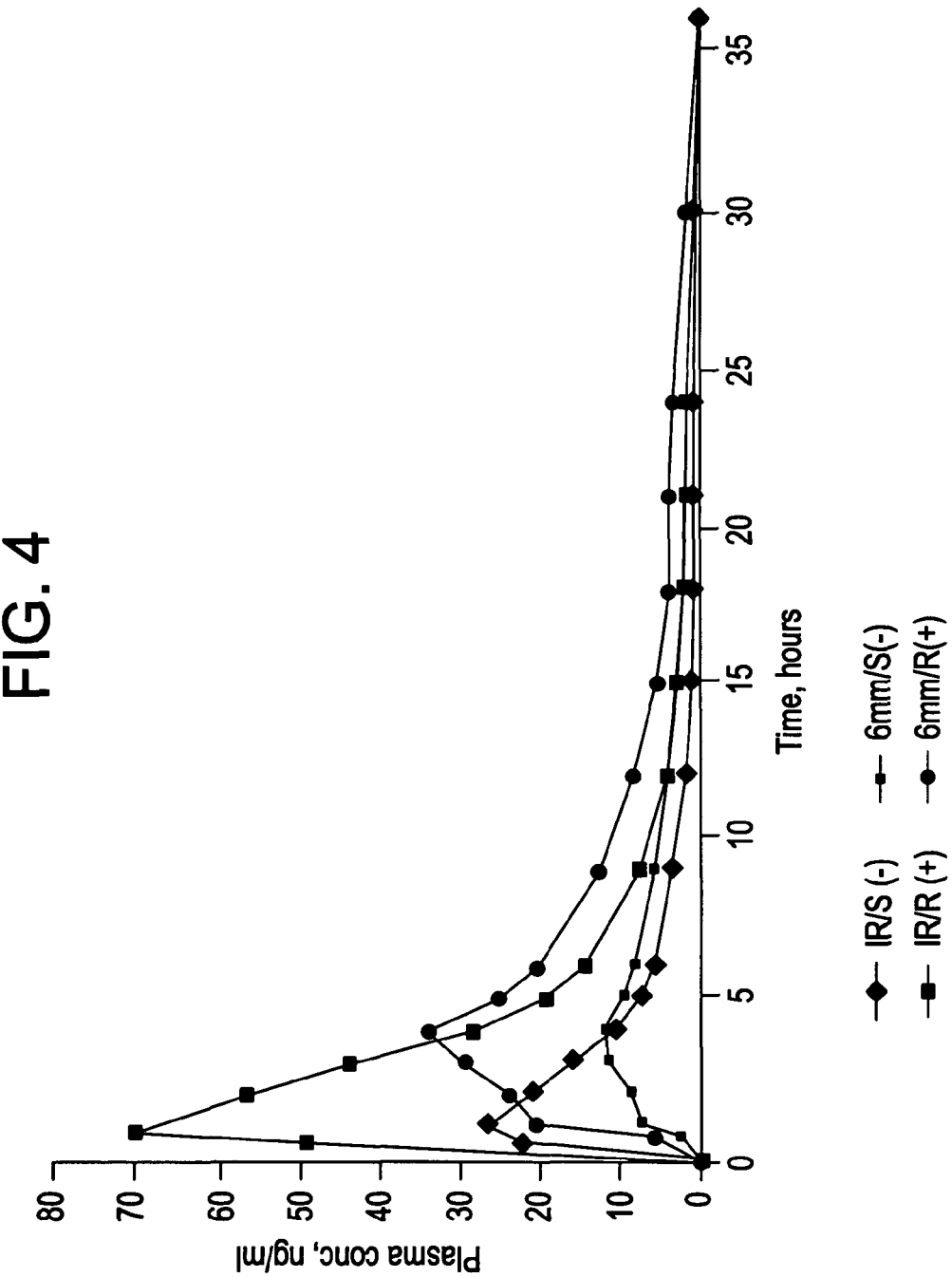
FIG. 4 shows the plasma profiles of the individual enantiomers. The same pattern as in FIG. 2 is seen, i.e. a prolonged effect of the individual enantiomers and a reduced maximum plasma concentration.

FIG. 4 shows the plasma concentration for the individual enantiomers vs. time for pilot study II in which Egalet® 6 mm, oval shape, was tested in 7 subjects.

Figure 5:
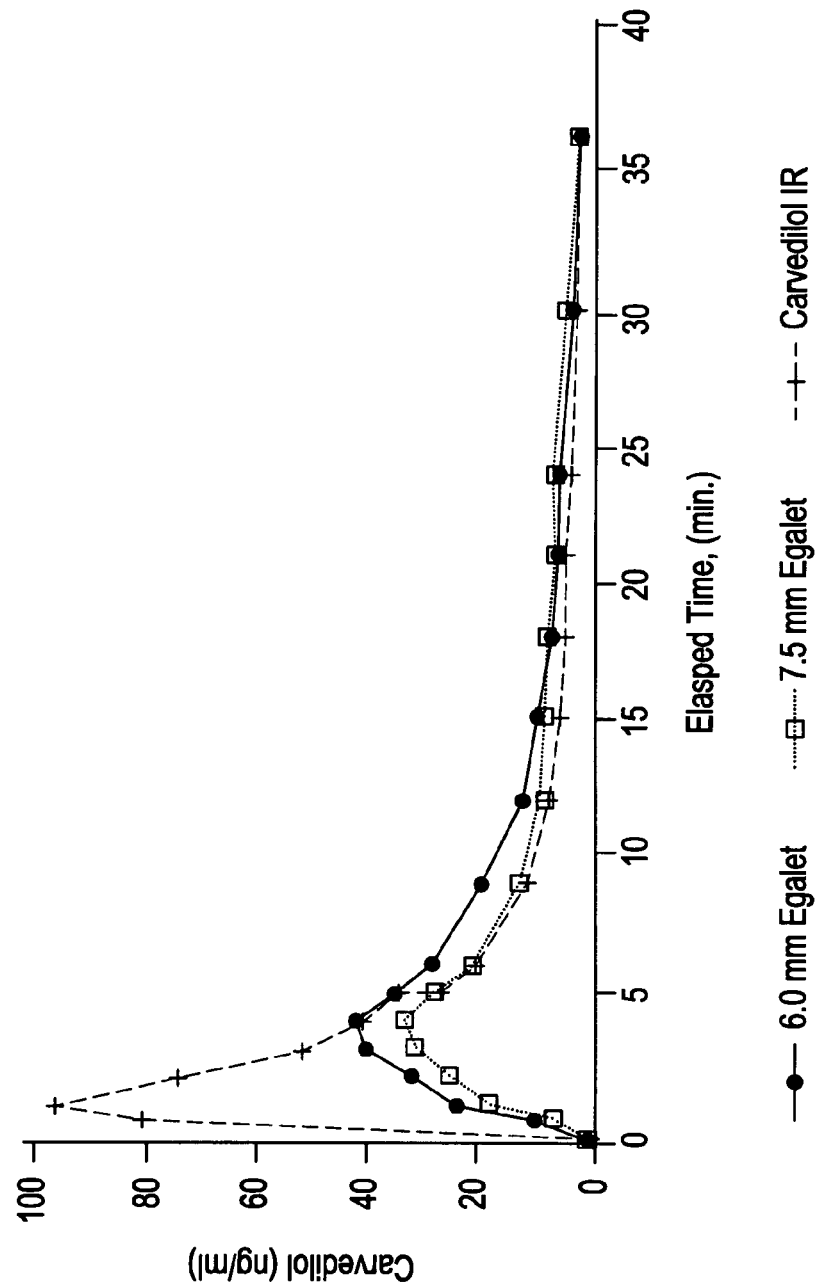
FIGS. 5-7 show the plasma profiles of carvedilol (sum of the individual enantiomers), R(+) carvedilol and S(−) carvedilol, respectively after administration of Dimitone® (50 mg carvedilol) and a 50 mg carvedilol composition according to the invention.
Figure 6:
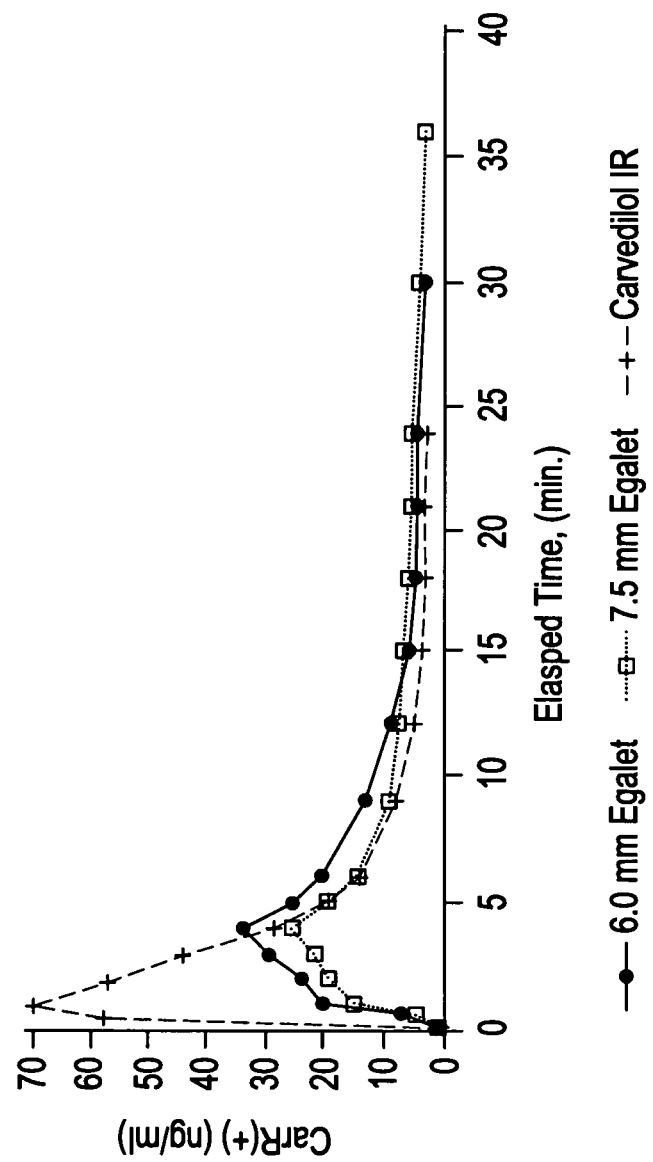
Figure 7:
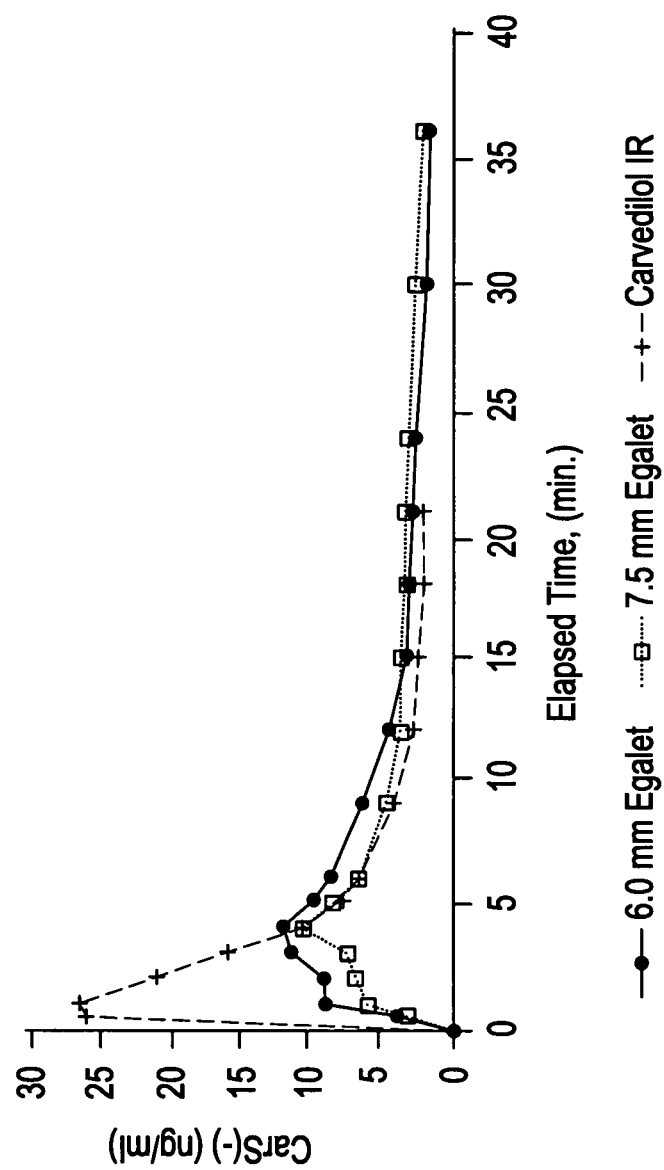

FIGS. 5-7 show the plasma profiles of carvedilol (sum of the individual enantiomers), R(+) carvedilol and S(−) carvedilol, respectively after administration of Dimitone® (50 mg carvedilol) and a 50 mg carvedilol composition according to the invention.

Figure 8:
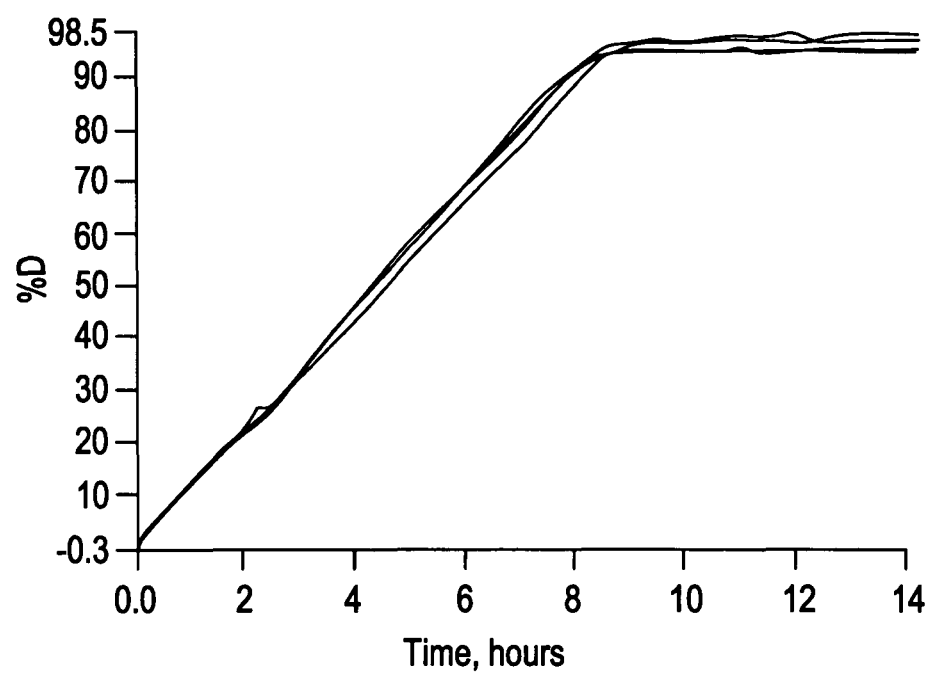
Figure 9:
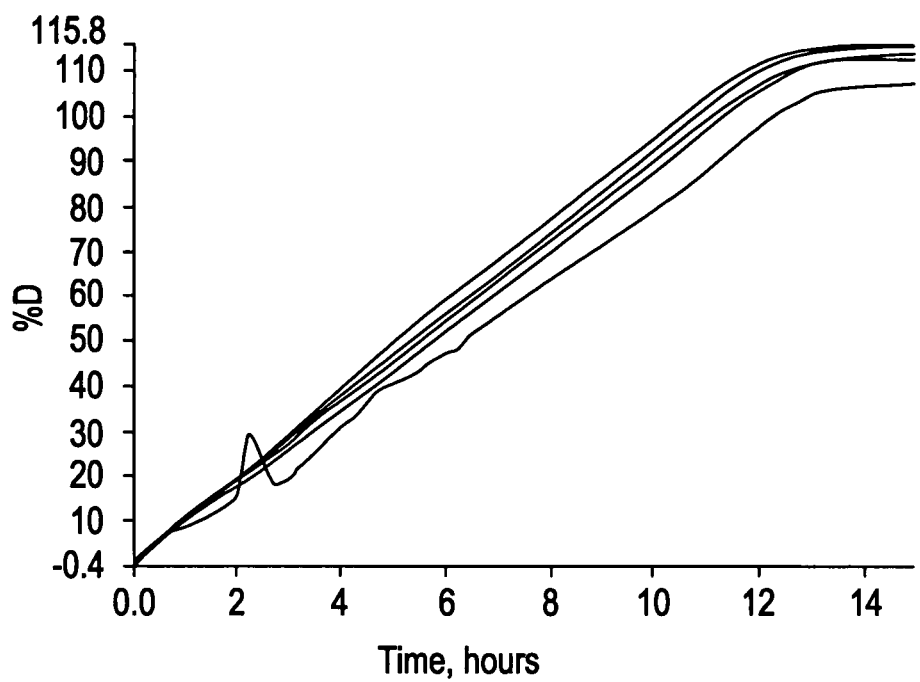

FIGS. 8-9 show the dissolution profiles of compositions used in pilot study III. The dissolution profile was run in 1000 ml 0.1 M HCl for 1 hour (120 rpm) followed by 1000 ml buffer, pH 6.8, 150 rpm and at 37° C.

Figure 10:
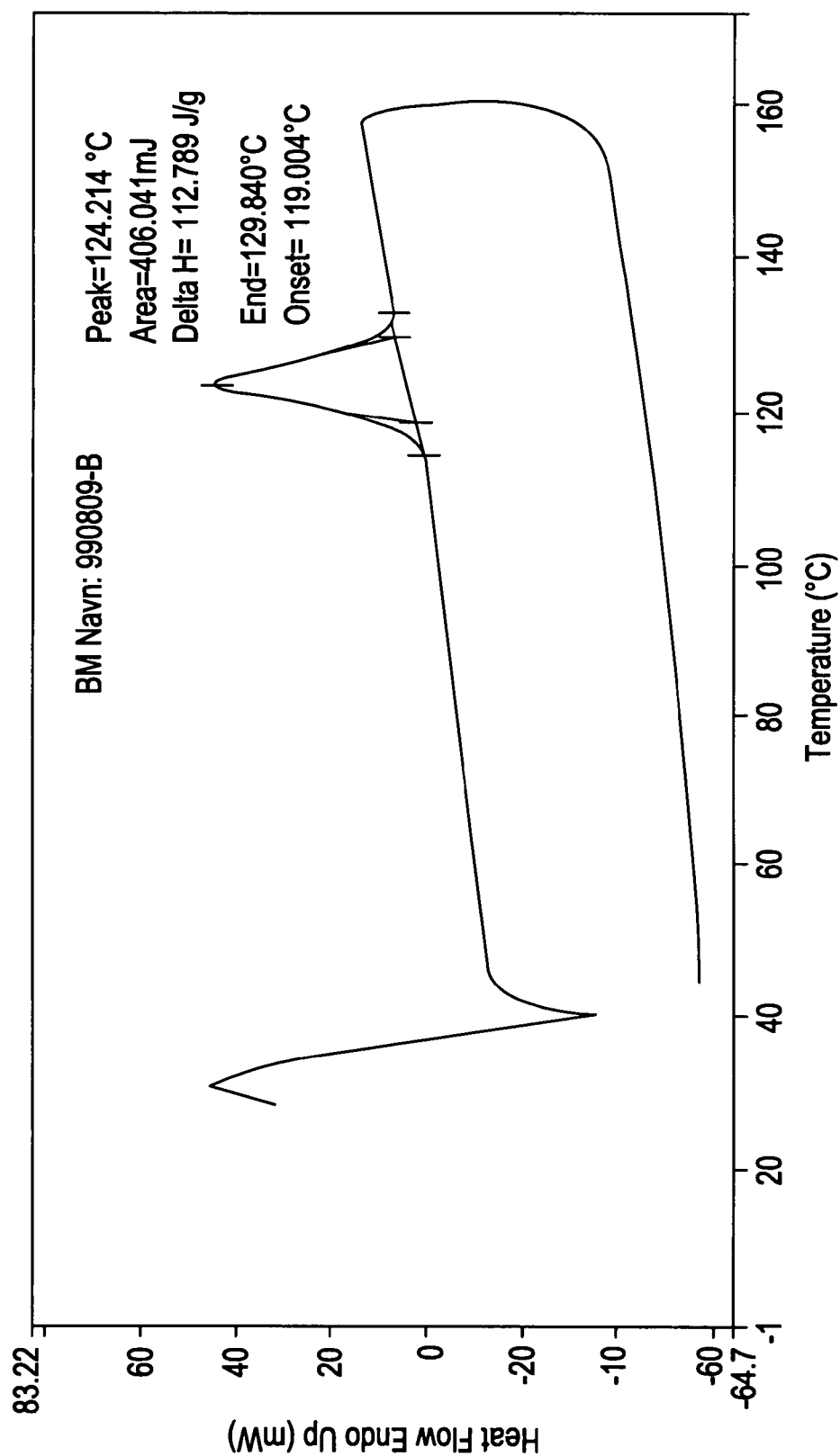

FIG. 10 shows the DSC of carvedilol as starting material and a peak is observed corresponding to that carvedilol is employed in crystalline form.

Figure 11:
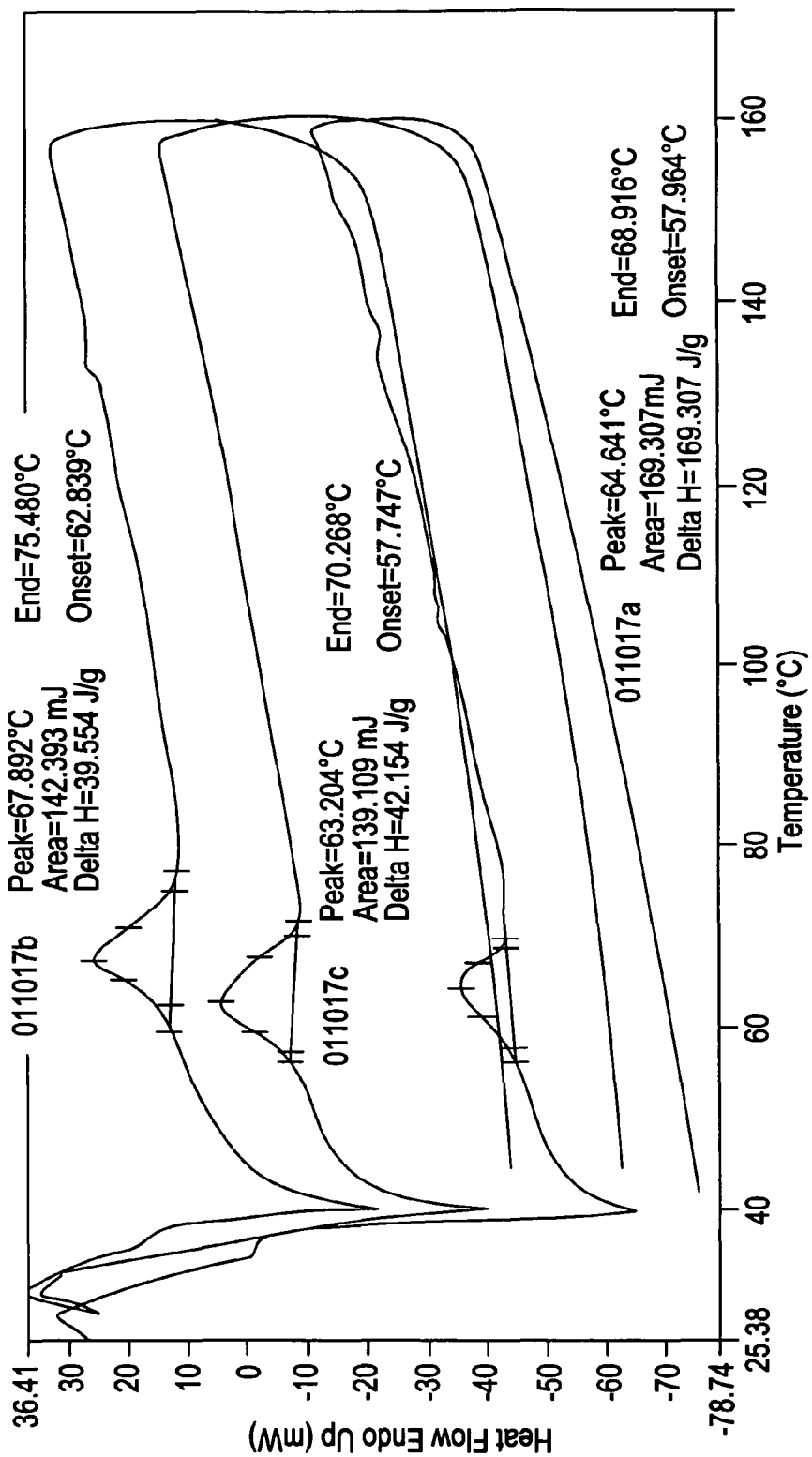

FIG. 11 shows DSC's of compositions according to the invention. No peak is present for carvedilol indicating the carvedilol is present in amorphous form.

Figure 12:
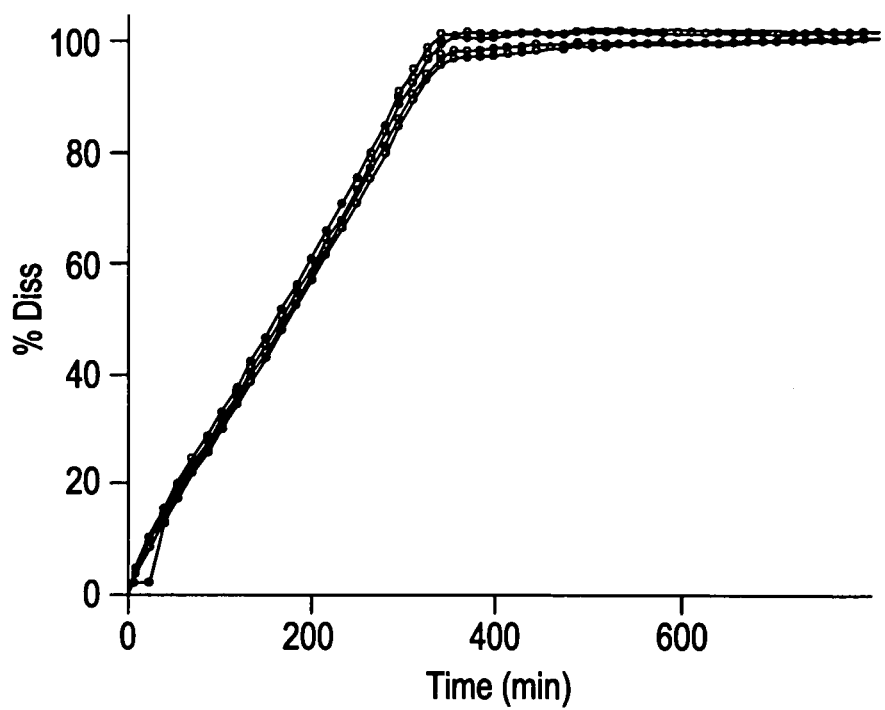

FIG. 12 show the dissolution profile of a 6.8 mm long 25 mg composition used in phase 1 study 2003. The dissolution profile was run in 900 ml buffer, pH 6.8, 50 rpm and at 37° C.

FIG. 13 shows the plasma concentration of R(+)-carvedilol and S(−)-carvedilol, respectively, from the clinical study described in Example 8.

Figure 14:
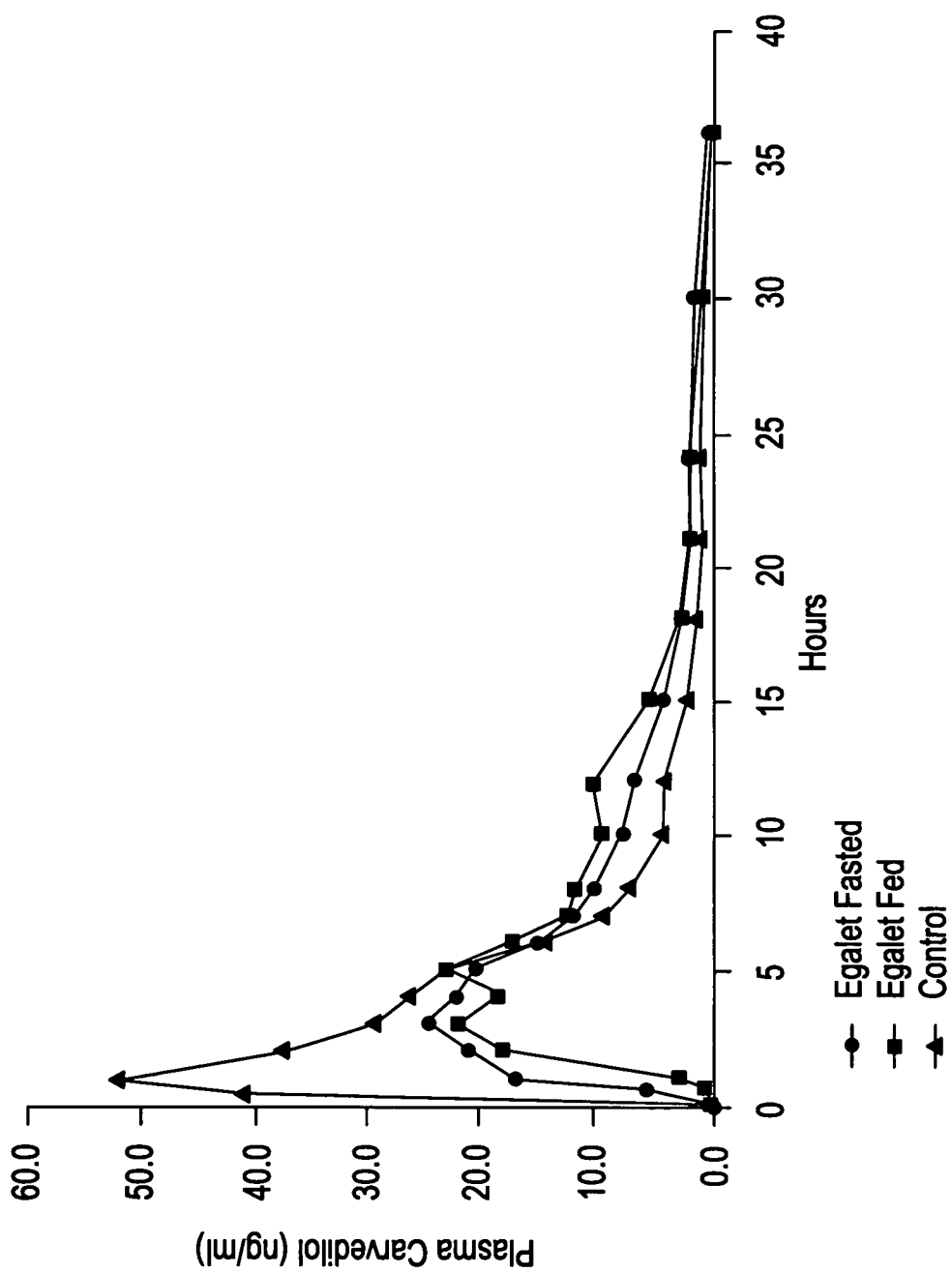

FIG. 14 shows the plasma concentration of total carvedilol from the clinical study described in Example 8.

Figure 15:
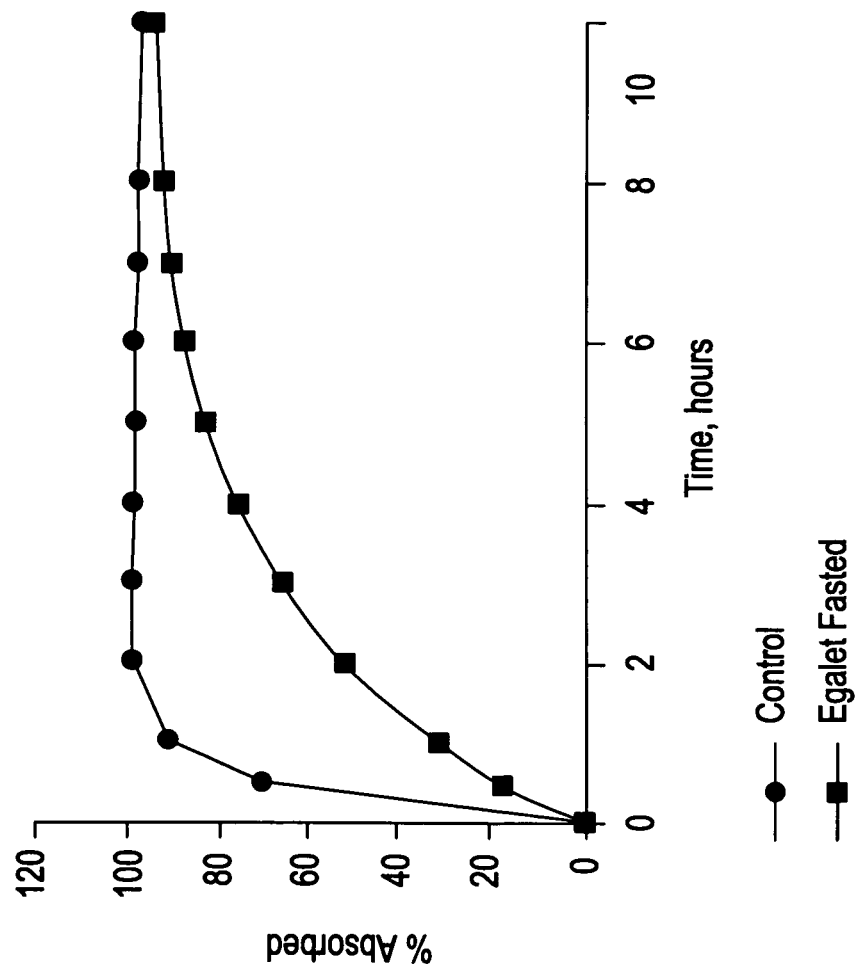
Figure 16:
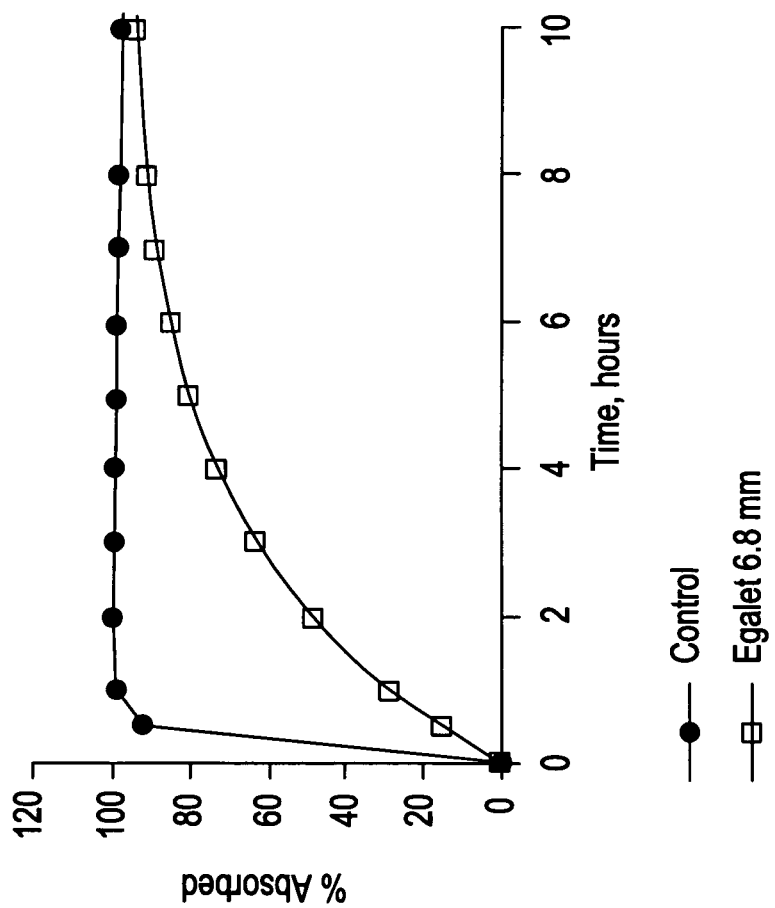
Figure 17:
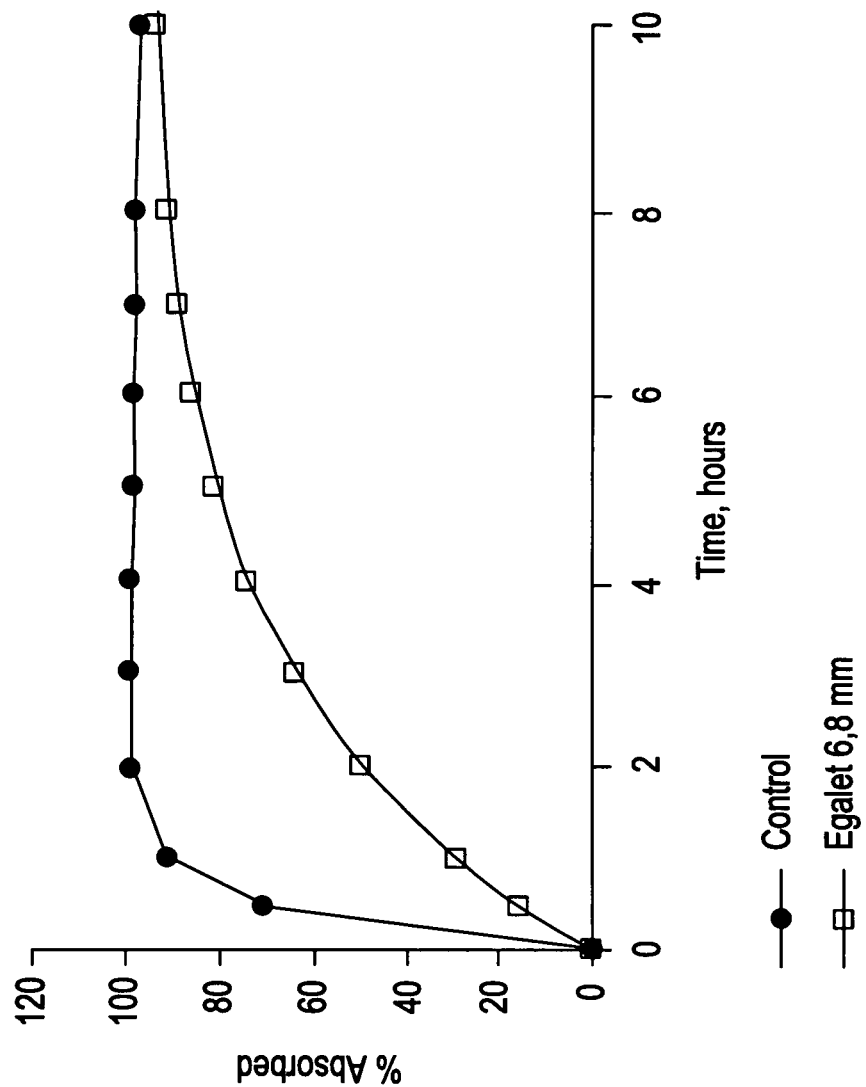

FIGS. 15-17 shows absorption rate of a composition similar to the composition disclosed in FIG. 12 compared with an IR formulation (for total carvedilol, S-carvedilol and R-carvedilol, respectively).

METHODS

Diffusion/Dissolution Studies

Method for Determination of Dissolution Rate of the Matrix

Thermoplastic substantially water soluble polymers are hydrophilic and in contact with water some degree of water absorption will take place. A sharp advancing water front divides the intact and not penetrated core from a swollen front. Under stationary conditions, a constant thickness surface layer is formed by the swollen polymer and by a high concentration polymer solution. In fact, once the hydrodynamic external conditions are defined, a stationary state is reached where the rate of penetration of the moving boundary equals the rate of removal of the polymer at the external surface (erosion or bulk erosion). The time lapse until the quasi-stationary state is reached is swelling time. At steady state, the dissolution rate is constant and can be defined equally by either the velocity of the retracting front of the polymer or the velocity of the front separating the pure penetrate and the liquid dissolving sub layer. Thus, both fronts are synchronized.

In order to measure the diffusion rates of water samples may be prepared in the form of plugs fitting to the sample holder (e.g. 2 mm, 4 mm, 6 mm, 7.5 mm and 12 mm long and preferable with the same shape and volume as the desired dosage unit). The sample holder is prepared by translucent glass in a tubular shape and with noticeable marks indicated with a specific distance.

Place 1 plug incorporated into the glass tube in a vessel—optionally with a water soluble dye (e.g. $Cu^{2+}$)—and the plug/glass tube is placed in a dissolution apparatus e.g. according to monograph: USP 24, page 1941-1950, or as described herein.

Agitation is provided, and the length of the front of matrix is measured at desired time intervals as a function of time. The measurement may be a simple visual identification of the marks on the glass tube.

Any active ingredient released from the matrix may be measured from the dissolution medium simultaneously using standard methods.

When the dissolution rate equals the penetration rate a constant thickness surface layer is observed. The different dissolving layers in different matrices obtained during the water contact, reflect the different dissolution characteristics of the matrix. The thickness of the surface layer as a function of time is then compared. The specific aqueous medium may be selected individually.

Dissolution Test

Dissolution tests were performed in accordance with the USP 24, NF 19, (711) Dissolution, Apparatus 2 equipped with a paddle. The dissolution medium was 0.1 N hydrochloric acid during the first 120 min, which was then substituted with a buffer solution pH 6.8. The volume of the dissolution medium was 1000 ml and the rotation speed of the paddle was 120 rpm during the first 120 min and then 50 rpm. Samples were withdrawn at suitable time intervals and analyzed for content of carvedilol by means of UV spectrometry at a wavelength of 284 nm.

Alternatively, the dissolution is performed in 900 buffer pH 6.8, 50 rpm during the full dissolution test and is used for the dissolution tests as disclosed in Table 20 and FIG. 12.

EXAMPLES

A general method for the preparation of a controlled release composition is described below.

Preparation of a Matrix Composition According to the Invention

An accurate amount of the polymer (i.e. in the examples below: the polyethylene oxide) is loaded into a MTI mixer followed by an accurate amount of the active substance and of the pharmaceutically acceptable excipients(s), if any. The mixing is performed at 2050/1450 rpm and at a time period of 10 min+4 min+short final spinning. At the start of the mixing the temperature is about 19° C. (the first time period) and the final temperature of the mixture is about 52° C. (the second and third time period). The mixture is then allowed to cool to room temperature and is ready to be fed into an injection moulding machine.

Preparation of the Coating Composition

A coating composition was prepared by first adding the hydroxymethylcellulose then cetostearyl alcohol, and finally the titanium dioxide to an MTI-Mixer at a temperature about 21° C. After mixing for nearly 9 min at 1000 rpm (I: 0.9 A) the mixer was stopped (temperature about 46° C.) and the adhered material manually incorporated into the mixture. The mixture was left to cool for about 10 minutes. The mixing is then finalized with a short high-speed mix in order to minimize lumps formation. The mixture was then allowed to cool to room temperature, after which it had a suitable consistency for being fed into an injection moulding machine.

Example of Coat Composition

Batch: 58-014-01-013

| % | Batch | Material | amount (g) | Weight (g) | step |
|---|---|---|---|---|---|
| 79 | 991207-A | Ethocel | 632 | 632 | 1 |
| 20 | 990426-B | Cetylstearyl Alkohol | 160 | 160.1 | 2 |
| 1 | 97051301 | TiO$_2$ | 8 | 8.0 | 3 |
| 100 | | total | 800 | 800.1 | |

The final dosage units may be prepared according to two different methods. In one method, the coat and the matrix moulded individually followed by a manually incorporation of the moulded matrix plug into the moulded coat. The moulding machine used is an Arburg Allrounder 220 S 250/60.

In a second method, the coat and matrix are moulded in one process where the coat is moulded in a first step and the matrix is moulded directly into the coat in a second step. The moulding machine used is Arburg Allrounder 420 V 800-60/35.

The following table describes formulations having a cylindrical form and circular openings in both ends.

| Batch | Length [mm] | Diameter [mm] | Vol [mm$^3$] |
|---|---|---|---|
| 01-0034-042 | 7.5 | 5.05 | 150 |
| 01-0035-042 | 6.0 | 5.64 | 150 |
| 01-0043-042 | 9.0 | 4.6 | 150 |

The following table describes formulations having a cylindrical form and oval openings in both ends

| Batch | Length [mm] | Vol [mm$^3$] | Longest/shortest diameter [mm] | |
|---|---|---|---|---|
| 01-0075-042 | 6.0 | 150 | 8.74 | 3.64 |
| 01-0076-042 | 7.5 | 150 | 7.82 | 3.21 |
| 01-0121-042 | 6.0 | 150 | 8.74 | 3.64 |

The coated compositions obtained were open at two opposite ends. The area for an open end is calculates as the volume/length of the cylindrical formulations.

Example 1

Preparation of a Pharmaceutical Composition Comprising Carvedilol as an Active Substance A composition (plug batch No. 01-0045-042), formulation batch No. 01-0034 042 according to the invention was prepared from the following ingredients:

| No | Raw materials | Reference: |
|---|---|---|
| 1 | PEO 200,000 | S-Ega40200; USP24-NF19 2000 p. 2497 |
| 2 | Carvedilol | Ph. Eur. 3rd Ed. 2000 p.359 |
| 3 | Citric Acid | Ph. Eur. 3rd Ed. 1997 p.645 |

| Matrix | |
|---|---|
| Polyethylene oxide | 64.6 |
| Carvedilol (Cipla) | 30 |
| Citric acid | 5.4 |

The coating and the matrix were prepared as described above. One dosage form contains 50 mg carvedilol. The composition was 7.5 mm long.

The composition was subjected to the dissolution test described above. The following results were obtained:

| Time (h) | dissolved carvedilol (% w/w of the coated composition) |
|---|---|
| 0 | 0 |
| 1 | 14.1 |
| 2 | 27.1 |
| 3 | 39.3 |
| 4 | 49.9 |
| 5 | 60.7 |
| 6 | 72.5 |
| 7 | 85.0 |
| 8 | 99.7 |

The dissolution profile corresponds to a zero order release of carvedilol from the composition.

Example 2

Preparation of an Oval Shaped Pharmaceutical Composition Comprising Carvedilol as an Active Substance A composition (batch No. 01-0076-042) according to the invention was prepared from the following ingredients:

| Matrix | |
|---|---|
| Polyethylene oxide | 64.6 |
| Carvedilol (Cipla) | 30 |
| Citric acid | 5.4 |

The coating and the matrix were prepared as described above. One dosis form contains 50 mg carvedilol. The composition was 7.5 mm long and had an oval cross sectional shape.

The composition was subjected to the dissolution test described above. The following results were obtained:

| Time (h) | dissolved carvedilol (% w/w of the coated composition) |
|---|---|
| 0 | 0 |
| 1 | 15.9 |
| 2 | 30.1 |
| 3 | 46.2 |
| 4 | 62.2 |
| 5 | 77.61 |
| 6 | 92.4 |

The dissolution profile corresponds to a zero order release of carvedilol from the composition.

Example 3

Preparation of a Pharmaceutical Composition Comprising Carvedilol as an Active Substance A composition (plug batch No. 01-0044-042, dosage unit batch No. 01-0043 042) according to the invention was prepared from the following ingredients:

| Matrix | |
|---|---|
| Polyethylene oxide | 64.6 |
| Carvedilol (Cipla) | 30 |
| Citric acid | 5.4 |

The coating and the matrix were prepared as described above. One dosage form contains 50 mg carvedilol. The composition was 9 mm long.

The composition was subjected to the dissolution test described above. The following results were obtained:

| Time (h) | dissolved carvedilol (% w/w of the coated composition) |
|---|---|
| 0 | 0 |
| 1 | 13.2 |
| 2 | 22.5 |
| 3 | 33.2 |
| 4 | 44.7 |
| 5 | 56.2 |
| 6 | 67.0 |
| 7 | 77.2 |
| 8 | 88.1 |
| 9 | 98.6 |

The dissolution profile corresponds to a zero order release of carvedilol from the composition.

Example 4

Preparation of a Pharmaceutical Composition Comprising Carvedilol as an Active Substance A composition (batch No. 01-0075-042) according to the invention was prepared from the following ingredients:

| Matrix | |
|---|---|
| Polyethylene oxide | 64.6 |
| Carvedilol (Cipla) | 30 |
| Citric acid | 5.4 |

The coating and the matrix were prepared as described above. One dosage unit form contains 50 mg carvedilol. The composition was 6 mm long and had an oval shape.

The composition was subjected to the dissolution test described above. The following results were obtained:

| Time (h) | dissolved carvedilol (% w/w of the coated composition) |
|---|---|
| 0 | 0 |
| 1 | 17.0 |
| 2 | 35.1 |
| 3 | 55.1 |
| 4 | 74.7 |
| 5 | 93.8 |

The dissolution profile corresponds to a zero order release of carvedilol from the composition.

Example 5

Preparation of a Pharmaceutical Composition Comprising Carvedilol as an Active Substance A composition (batch No. EC-042-211) according to the invention was prepared from the following ingredients:

| Matrix | |
|---|---|
| Polyethylene oxide | 86 |
| Carvedilol (Cipla) | 14 |

The coating and the matrix were prepared as described above. One dosage unit form contains 25 mg carvedilol. The composition was 12 mm long and had circular end surfaces.

The composition was subjected to the dissolution test described above. The following results were obtained:
Dissolved carvedilol (% w/w of the coated composition) from hour 1 to 15 hours

| Time (h) | dissolved carvedilol (% w/w of the coated composition) |
|---|---|
| 1 | 12.4 |
| 2 | 21.6 |
| 3 | 29.2 |
| 4 | 35.4 |
| 5 | 40.0 |
| 6 | 44.5 |

-continued

| Time (h) | dissolved carvedilol (% w/w of the coated composition) |
|---|---|
| 7 | 49.4 |
| 8 | 54.3 |
| 9 | 59.4 |
| 10 | 64.6 |
| 11 | 70.6 |
| 12 | 75.5 |
| 13 | 79.8 |
| 14 | 84.1 |
| 15 | 88.7 |
| 16 | 92.6 |
| 17 | 94.6 |

The dissolution profile corresponds to a zero order release of carvedilol from the composition.

Example 6

Pilot Phase I Studies in Health Volunteers Employing Carvedilol Compositions According to the Invention Carvedilol has emerged as one of the important and promising drugs for cardiovascular diseases including hypertension and congestive heart failure, and results in a noticeable improvement of survival rates in patients with chronic cardiac insufficiency. To further optimize the treatment, Carvedilol Egalet® has been developed as a once daily composition. Carvedilol is currently marketed as an immediate release formulation only in 3.125 mg, 6.25 mg, 12.5 mg, 25 mg and 50 mg tablets. Only the 6.25 mg and 25 mg application form is available throughout the EU whilst of the other strengths some are missing in certain member states. A 25 mg immediate release application form may be used as a reference.

Carvedilol Egalet® is developed for long-term treatment of hypertension and is therefore developed for a maintenance dosage. However, the present invention encompasses other dosages where a controlled delivery is desired.

The expected advantages offered by the Carvedilol Egalet® compared to the immediate release formulation include:

i) Reduced standard deviation and thus, a more predictable concentration in plasma.

ii) A dose regimen with lower frequency of administration and thereby potentially improvement of patient compliance.

For patients with cardiac insufficiency, it is recommended to take Carvedilol with a meal to delay absorption and thereby avoid adverse reactions. Carvedilol Egalet® offers the advantage of reduced $C_{max}$, even if taken fasting. (Latest studies CL-EG-pilot-1 and CL-EG-pilot-02 shows that $C_{max}$ is only slightly as high as for 25 mg Carvedilol IR).

Patients with hypertension have a well-described low compliance, presumably because there are no recognizable symptoms connected with the condition. Compliance with a once-daily regimen is higher and therefore offers a therapeutic advantage. Recommendations for the use of Carvedilol vary between countries.

An evaluation of Carvedilol in "Drugs" from 1997 lists in the summary under Dosage and Administration "A dosage of Carvedilol 12.5 mg once daily for 2 days, increased to 25 mg daily thereafter and increased to 50 mg once daily after 2 weeks if necessary, is recommended for patients with mild to moderate hypertension". According to the American Physician's Desk Reference (PDR) 2000, Carvedilol should be prescribed twice daily for all indications. According to the German Drug Listing (Rote Liste 2001 for Dilatrend®), Carvedilol should be prescribed twice daily for cardiac insufficiency and angina pectoris, and once to twice daily for hypertension with a maximum dose of 2×25 mg. According to "Drugs, Fact and Comparison", Carvedilol is prescribed twice daily for hypertension. In all countries, the maximum daily dose is 25 mg b.i.d., and it is against this dose and frequency that Carvedilol Egalet® is tested herein.

Composition of Carvedilol Egalet®

In the development work on Carvedilol Egalet®, different compositions of matrix have been tested, i.e. the load of drug has been varied.

In Table 1 below is given the final composition of the coated composition used in the pilot studies. The individual composition employed in Pilot tests III, IV and V corresponds to the compositions of Examples 1-4.

TABLE 1

Composition of Carvedilol Egalet ®

| Ingredients | Percentage | Function | Reference to standards |
|---|---|---|---|
| Active substance | | | |
| Carvedilol | 32% | Active compound | Cipla |
| Excipients | | | |
| Citric Acid | 5% | Matrix | Ph. Eur. |
| Polyethylene Oxide (PEO 200000) | 63% | Matrix | USP |
| Ethylcellulose | 79% | Shell | Ph. Eur |
| Ceto-stearyl alcohol | 19.8% | Shell | Ph. Eur |
| Titanium dioxide | 1% | Shell | Ph. Eur |
| Ferro Oxide | 0.2% | Colouring | USP |

Pharmacodynamics

There are several pharmacodynamics issues to be described for the Carvedilol Egalet®. The following is a list of issues and the considerations regarding their testing.

1. Bioavailability (rate and extent of absorption, fluctuations in drug concentration, variability arising from the formulation, dose proportionality, risk of unexpected release characteristics)

2. Factors influencing the performance of a modified drug formulation (GI function, diurnal rhythm)

3. Stereoisomers

Absorption: There is no literature on slow release formulations of Carvedilol. One study has been identified on in-vivo absorption of Carvedilol formulated in timed-release capsules. This study by Nolte et al found absorption throughout the GI tract, correlating with the absolute absorption areas of the different parts of the intestinal tract. They found a relatively high absorption of Carvedilol in the large intestine, amounting to approximately 10% of the total absorption. This supports the findings from the pilot studies performed on the Carvedilol Egalet®, where the plasma curves show that Carvedilol is being absorbed throughout the GI tract, including the colon, and that the absorption in the colon is present, but considerably reduced compared to earlier in the GI tract.

Fluctuations: To evaluate fluctuations in plasma concentration, comparison should be made between plasma profiles from the same concentration given. Data from pilot study IV and V on Carvedilol IR 50 mg compared to Carvedilol Egalet® 50 mg shows that Cmax for the Carvedilol Egalet® is reduced approximately 50%, whereas the C24h, which will correspond to $C_{min}$ in a once daily dosing, is 2.5 times as high. In the studies, the Carvedilol IR has been given in a single dose. Patients will be taking Carvedilol IR b.i.d., wherefore peak/trough ratio should be measured for this dose regimen. This will be done in the steady state studies.

Variability: In published literature the variability of Carvedilol is very high, with standard deviations of >50%. The study with the highest number of subjects, i.e. 44 shows a SD of 70%. There are no indications that the variability will be higher than for the immediate release formulation.

Dose proportionality: Literature describes dose linearity for Carvedilol in the range of 6.25-50 mg.

Dose dumping: Carvedilol is being released from the Egalet® tablet by the erosion of the matrix from the exposed surfaces only as the coat prevents contact to the aqueous medium of the intestines. Accordingly, release of all of the Carvedilol at one time is not possible. A further advantage of the injection moulding of shell and matrix in one process step is that the shell and the matrix reach a high degree of adherence. An uncoated and thus unprotected matrix has been investigated through dissolution tests, which show that release time in-vitro for a freely exposed Carvedilol matrix from a 9 mm Egalet® is about two hours. Accordingly, the coating actively prevents release due to the limited exposed area. In addition, the in-vivo-in-vitro correlation of the Egalet® has been described to some extend through scintigraphy. 2 hours in vitro release in the stomach will correspond to at least 3 hours in vivo, and will not be below 2 hours. Thus any dose dumping would be of less severity than seen after intake of 50 mg conventional immediate release tablet.

The immediate release tablet has been investigated as 50 mg o.d. in several clinical studies, but is associated to an increased number of adverse events, compared to lower doses, due to the increased trough-peak ratio.

GI function: GI transit time may influence the release rate. A very fast transit time where the tablet is excreted before the content is fully released, will result in a decreased AUC. This is a well-described issue for slow release products. For Carvedilol Egalet® the effect of GI transit time can be clearly demonstrated because the non-degradable shell can be collected. When all Carvedilol is released with normal transit times, remaining Carvedilol can be found in the shells with decreased transit time. This has been documented in findings from pilot study III. As release rate is constant for any given formulation, release time is depending on the length of the Egalet® tablet. For the matrix formulation described in Table 1, which releases at the rate of 1 mm/hour in in-vitro dissolution, tablets of 9 mm have shown complete release with normal transit time. The absorption of Carvedilol Egalet® in patients with Morbus Crohn and Collitis ulcerosa has not been investigated. Until that is performed, the use of the product in the patient population is contraindicated.

Diurnal rhythms: Carvedilol has been shown to preserve the diurnal rhythm of blood pressure; there are no reasons to believe that a slow release formulation will influence this rhythm differently than the IR formulation. This will be explored in the phase II study, where ambulatory BP will be measured for 24 hours.

Stereoisomers: Carvedilol is a racemic mixture of R(+) and S(−)-enantiomers; S(−), which is a potent β1 and β2 antagonist and α-adrenoceptor antagonist and R(+), which has 1/100 of the beta effect and the same α effect as the S(−). The pharmacokinetics of these is described both in healthy volunteers and in patients with cardiac insufficiency. The plasma profiles of the enantiomers seen after intake of the Carvedilol Egalet® could be different from the one seen after Carvedilol immediate release, given that the t½ of the two are different (9.6 h for R(+) and 22.1 h for S(−)). In steady state, however, the plasma profiles are similar to that of Carvedilol, and it is not expected that the blood pressure lowering effect will be different for the Carvedilol Egalet® than for the Carvedilol IR. It is planned to measure the stereoisomers in the steady state study for regulatory submission. To obtain preliminary information, blood samples from a single dose from the pilot study V or VI will be analysed for the isomers.

Pilot Phase I Studies
Completed Pharmacokinetic Studies

The pharmacokinetic studies on Carvedilol Egalet® listed in Table 1 are part of the development work to obtain preliminary information on the pharmacokinetics.

TABLE 2

Completed pilot pharmacokinetic studies, listed chronologically

| Study No. | Design | Treatment | Doses (mg)[a] | No. of subjects |
|---|---|---|---|---|
| Pilot test I | Single-dose PK: Open-label, 2-armed, parallel group (Carvedilol Egalet ® vs. Carvedilol IR) | Single-dose | C Egalet: 25 mg C IR: 25 mg | 6 |
| Pilot test II | Single-dose PK: Open-label, 2-armed, parallel group (Carvedilol Egalet ® vs. Carvedilol IR) | Single-dose | C Egalet: 50 mg C IR: 50 mg | 6 |
| Pre-Pilot I | Single-dose PK: Open-label, Carvedilol Egalet ® | Single-dose | C Egalet: 50 mg | 2 |
| Pre-Pilot II | Single-dose PK: Open-label, Carvedilol Egalet ® | Single-dose | C Egalet: 50 mg | 2 |
| Pre-Pilot III | Single-dose PK: Open-label, Carvedilol Egalet ® | Single-dose | C Egalet: 37.5 mg | 2 |
| Pre-Pilot IV | Single-dose: Collection of excreted shells | Single-dose | C Egalet: 50 mg | 2 |
| Pilot test III | Single-dose PK: Open-label, 4-way cross-over study (3 doses Carvedilol Egalet ® vs. Carvedilol | Single-dose | C Egalet: 25 mg/ 37.5 mg/50 mg o.d. | 6 |

TABLE 2-continued

Completed pilot pharmacokinetic studies, listed chronologically

| Study No. | Design | Treatment | Doses (mg)[a] | No. of subjects |
|---|---|---|---|---|
| | IR) | | C IR: 37.5 mg b.i.d. | |
| Pilot Test IV | Single-dose PK: Open-label, 4-way cross-over (3 different shapes of Carvedilol Egalet ® vs. Carvedilol IR) | Single-dose | C Egalet: 50 mg o.d. C IR: 50 mg o.d. | 10 |
| Pilot Test V | Single-dose PK: Open-label, 4-way cross-over (2 different shapes of Carvedilol Egalet ® vs. Carvedilol IR) As a final fixed sequence arm; the chosen shape of Carvedilol Egalet ® in fed subjects | Single-dose | C Egalet: 50 mg o.d. C IR: 50 mg o.d. | 10 |

In all studies, the investigational products were administered orally as tablets.

The formulations tested in these studies showed a prolonged release of Carvedilol with reduced $C_{max}$ and measurable plasma concentrations over 36 hours.

Results and Discussion—Pilot Pharmacokinetic Studies

The pilot phase I studies completed up to now clearly indicates that it is possible to produce a slow release Carvedilol Egalet® with a PK profile required of a once daily formulation. In pilot test III, the influence of the length of Egalet® tablet on the release characteristics was described. In pilot test IV, Egalet® tablets with 3 different diameters and lengths has been tested. In vitro dissolution tests indicated that an increased diameter would not influence the speed of erosion and pilot IV and V has confirmed this. $C_{max}$ is increasing proportionally to the increasing surface area exposed of Egalet® composition. $T_{max}$ does not differ between the formulations. The mean of the plasma concentrations measured for the 6 mm Carvedilol Egalet® 50 mg is reduced due to an unexpected high number of subjects having a fast transit time in that treatment group; 6 of 10 subjects excreted the Egalet® before hour 24.

In pilot study V, two of the same lengths of Carvedilol Egalet® as in pilot test IV were tested, but in a different oval shape, and compared to Carvedilol immediate release. Preliminary data assessment supports the conclusion from pilot study IV that $C_{max}$ increases with increasing diameter of the Egalet®. When comparing data for the round Egalet® in pilot IV to the "easy-to-swallow" oval shaped Egalet® in pilot V, for the 6 mm and the 7½ mm lengths respectively, and the exposed matrix area being constant, there are no observed difference by the change of shape. To obtain preliminary information on the effect of food on Carvedilol Egalet®, the 6 mm Egalet formulation was tested after a standard, high-fat meal, according to guidelines. The first 3 arms of the study were randomised and the last, the fed, was a fixed sequence arm. The data results from the last sequence have not been received yet and full data analysis for pilot study V has thus not been completed.

The composition, the Carvedilol Egalet® 6 mm, is a composition, for which we aim at showing an AUC equivalent to the marketed twice-daily formulation.

Preliminary data assessment from pilot study V shows for the 6 mm oval Egalet an

| Formulation | n | AUC (0-36 h) h * ng/ml | rel. AUC % | C max ng/ml | C (12 h) ng/ml | C (24 h) ng/ml | t max hours |
|---|---|---|---|---|---|---|---|
| CL-EG-01 (round egalet) | | | | | | | |
| 9 mm | 10 | 285 | 70 | 26.7 | 7.1 | 4.2 | 3 |
| 7½ mm | 10 | 355 | 88 | 37.8 | 10.3 | 3.8 | 4 |
| 6 mm | 10 | 336 | 76 | 37.4 | 9.1 | 2.9 | 4 |
| IR | 10 | 433 | 100 | 105.5 | 5.8 | 1.9 | 1 |
| CL-EG-02 (oval egalet) | | | | | | | |
| IR | 10 | 444 | 100 | 95.8 | 6.6 | 2.4 | 1 |
| 7½ mm | 10 | 344 | 76 | 33.2 | 9.0 | 5.0 | 4 |
| 6 mm | 10 | 421 | 97 | 41.7 | 11.8 | 4.8 | 4 |
| 6 mm + food | 10 | 362 | 80 | 39.0 | 10.9 | 3.9 | 3 |

AUC of 97.7% of the Carvedilol IR in fasting subjects. In the table is given relevant pharmacokinetic parameters from the pilot studies (see also FIG. 1).

From further studies, the results given in Tables 3-12 are obtained. The results are also shown in FIGS. 2-7. The dissolution profiles of the compositions used in Pilot study III are shown in FIGS. 8-9.

TABLE 3

: Summary Statistics for each Treatment for Pharmacokinetic Parameters from Carvedilol Profiles

| | 5.0 mm Egalet | 5.0 mm Food | 7.5 mm Egalet | Carvedilol IR |
|---|---|---|---|---|
| AUC(0-inf) ((ng/ml) * h) | | | | |
| N | 10 | 10 | 10 | 10 |
| Mean | 447.97 | 400.98 | 374.40 | 469.06 |
| SD | 108.27 | 145.18 | 160.94 | 162.93 |
| Median | 436.74 | 385.89 | 299.74 | 465.12 |
| Geometric Mean | 436.32 | 373.82 | 345.37 | 440.00 |

TABLE 3-continued

Summary Statistics for each Treatment for Pharmacokinetic Parameters from Carvedilol Profiles

|  | 5.0 mm Egalet | 5.0 mm Food | 7.5 mm Egalet | Carvedilol IR |
|---|---|---|---|---|
| Min | 301.28 | 159.21 | 167.52 | 197.27 |
| Max | 627.35 | 573.40 | 664.98 | 673.04 |
| AUC(0-36 h) ((ng/ml) * h) | | | | |
| N | 10 | 10 | 10 | 10 |
| Mean | 421.57 | 369.00 | 345.68 | 448.51 |
| SD | 109.50 | 141.11 | 144.60 | 153.57 |
| Median | 399.00 | 369.08 | 286.61 | 450.97 |
| Geometric Mean | 409.29 | 340.47 | 320.54 | 421.75 |
| Min | 285.48 | 136.15 | 163.15 | 191.18 |
| Max | 614.55 | 526.75 | 623.15 | 651.75 |
| $C_{max}$ (ng/ml) | | | | |
| N | 10 | 10 | 10 | 10 |
| Mean | 47.65 | 45.18 | 36.34 | 102.92 |
| SD | 18.34 | 18.42 | 10.64 | 36.92 |
| Median | 42.15 | 45.40 | 32.65 | 94.00 |
| Geometric Mean | 45.31 | 41.08 | 35.04 | 97.72 |
| Min | 33.70 | 14.00 | 25.10 | 66.20 |
| Max | 95.20 | 74.50 | 55.70 | 196.00 |
| $t_{max}$ (h) | | | | |
| N | 10 | 10 | 10 | 10 |
| Mean | 3.40 | 3.00 | 3.70 | 1.05 |
| SD | 0.97 | 0.94 | 0.48 | 0.55 |
| Median | 3.50 | 3.00 | 4.00 | 1.00 |
| Geometric Mean | 3.27 | 2.88 | 3.67 | 0.93 |
| Min | 3.00 | 2.00 | 3.00 | 0.50 |
| Max | 5.00 | 5.00 | 4.00 | 2.00 |
| MRT (h) | | | | |
| N | 10 | 10 | 10 | 10 |
| Mean | 12.21 | 13.48 | 13.12 | 7.31 |
| SD | 3.45 | 4.09 | 4.41 | 3.02 |
| Median | 10.82 | 12.81 | 12.18 | 6.81 |
| Geometric Mean | 11.76 | 12.93 | 12.38 | 6.81 |
| Min | 7.05 | 8.02 | 5.40 | 3.66 |
| Max | 17.17 | 20.63 | 20.27 | 13.80 | trial ID.: Egalet CL-EG-pilot-02
SD: Standard Deviation

TABLE 4

Two pairwise Comparisons of Treatments for Pharmacokinetics from Carvedilol Profiles. Estimate of Ratio with corresponding 90% Confidence Interval

|  | 6.0 mm Egalet vs Carvedilol IR | 7.5 mm Egalet vs Carvedilol IR |
|---|---|---|
| AUC (0-inf) | | |
| Estimate of Ratio | 1.00 | 0.81 |
| Lower 90% CL | 0.85 | 0.69 |
| Upper 90% CL | 1.19 | 0.96 |
| AUC (0-36 h) | | |
| Estimate of Ratio | 0.98 | 0.79 |
| Lower 90% CL | 0.84 | 0.67 |
| Upper 90% CL | 1.15 | 0.92 |
| $C_{max}$ | | |
| Estimate of Ratio | 0.47 | 0.36 |
| Lower 90% CL | 0.39 | 0.30 |
| Upper 90% CL | 0.57 | 0.44 |
| $t_{max}$ | | |
| Estimate of Ratio | 2.25 | 2.75 |
| Lower 90% CL | 1.50 | 2.25 |
| Upper 90% CL | 3.25 | 3.00 |
| MRT | | |
| Estimate of Ratio | 1.73 | 1.87 |
| Lower 90% CL | 1.38 | 1.49 |
| Upper 90% CL | 2.18 | 2.35 |

Trial ID.: Egalet CL-EG-pilot-02
CL: Confidence limit
'inf' means 'infinity'
Response in ANOVA model is the logarithm of the parameter in question.
Explanatory variables in ANOVA are Treatment (fixed) Period (fixed) and Pt.Id (random)
Estimated ratio is the antilog of the contrast between the two treatments
For $t_{max}$ the Hodges-Lehmann estimate and corresponding CL of median difference are shown.

TABLE 5

Least Square Geometric Mean for each Treatment for Pharmacokinetic Parameters from Carvedilol Profiles

| | 6.0 mm Egalet | 7.5 mm Egalet | Carvedilol IR |
|---|---|---|---|
| AUC (0-inf) ((ng/ml) * h) | | | |
| Least Square Geometric Mean | 434.88 | 352.29 | 432.79 |
| Lower 95% CL | 362.05 | 293.30 | 360.31 |
| Upper 95% CL | 522.35 | 423.16 | 519.85 |
| AUC (0-36 h) ((ng/ml * h) | | | |
| Least Square Geometric Mean | 408.26 | 326.29 | 415.37 |
| Lower 95% CL | 339.90 | 271.65 | 345.82 |
| Upper 95% CL | 490.37 | 391.91 | 498.91 |
| $C_{max}$ (ng/ml) | | | |
| Least Square Geometric Mean | 45.43 | 35.29 | 96.79 |
| Lower 95% CL | 38.32 | 29.76 | 81.64 |
| Upper 95% CL | 53.86 | 41.84 | 114.76 |
| MRT (h) | | | |
| Least Square Geometric Mean | 11.68 | 12.60 | 6.74 |
| Lower 95% CL | 9.68 | 10.44 | 5.58 |
| Upper 95% CL | 14.09 | 15.21 | 8.13 |

Trial ID.: Egalet CL-EG-pilot-02
CL: Confidence Limit
'inf' means infinity
Least square geometric means are estimated in ANOVA model
Response in ANOVA model is the logarithm of the parameter in question.
Explanatory variables in ANOVA are Treatment (fixed) Period (fixed) and Pt.Id (random)
No entries for $t_{max}$ since $t_{max}$ has been analysed using non parametric methods

TABLE 6

Summary Statistics for each Treatment for Pharmacokinetic Parameters from CarR(+) Profiles

| | 6.0 mm Egalet | 7.5 mm Egalet | Carvedilol IR |
|---|---|---|---|
| AUC(0-inf) ((ng/ml) * h) | | | |
| N | 7 | 6 | 7 |
| Mean | 317.75 | 295.92 | 334.70 |
| SD | 89.40 | 104.20 | 126.01 |
| Median | 326.35 | 303.50 | 277.18 |
| Geometric Mean | 307.53 | 279.71 | 315.09 |
| Min | 211.61 | 181.10 | 214.90 |
| Max | 478.99 | 406.12 | 518.68 |
| AUC(0-36 h) ((ng/ml) * h) | | | |
| N | 7 | 6 | 7 |
| Mean | 298.91 | 266.71 | 320.79 |
| SD | 91.24 | 93.89 | 117.71 |
| Median | 290.75 | 279.46 | 269.55 |
| Geometric Mean | 287.68 | 251.99 | 303.26 |
| Min | 190.35 | 154.15 | 208.45 |
| Max | 463.95 | 374.40 | 507.40 |
| $C_{max}$ (ng/ml) | | | |
| N | 7 | 6 | 7 |
| Mean | 37.44 | 26.20 | 74.03 |
| SD | 17.48 | 7.64 | 28.93 |
| Median | 31.70 | 24.00 | 65.40 |
| Geometric Mean | 34.83 | 25.32 | 69.95 |
| Min | 23.90 | 17.70 | 50.00 |
| Max | 74.50 | 38.50 | 129.90 |
| $t_{max}$ (h) | | | |
| N | 7 | 6 | 7 |
| Mean | 3.29 | 3.83 | 1.07 |
| SD | 1.39 | 0.41 | 0.45 |
| Median | 4.00 | 4.00 | 1.00 |
| Geometric Mean | 2.94 | 3.81 | 1.00 |
| Min | 1.00 | 3.00 | 0.50 |
| Max | 5.00 | 4.00 | 2.00 |
| MRT (h) | | | |
| N | 7 | 6 | 7 |
| Mean | 11.64 | 15.38 | 6.28 |
| SD | 2.03 | 3.34 | 3.88 |
| Median | 11.02 | 15.16 | 4.87 |
| Geometric Mean | 11.49 | 15.08 | 5.61 |
| Min | 8.52 | 11.45 | 3.58 |
| Max | 14.69 | 19.90 | 14.82 |

Trial ID.: Egalet CL-EG-pilot-02
SD: Standard Deviation

TABLE 7

Two pairwise Comparisons of Treatments for Pharmacokinetics from CarR(+) Profiles. Estimate of Ratio with corresponding 90% Confidence Interval

| | 6.0 mm Egalet vs Carvedilol IR | 7.5 mm Egalet vs Carvedilol IR |
|---|---|---|
| AUC (0-inf) | | |
| Estimate of Ratio | 0.96 | 0.94 |
| Lower 90% CL | 0.96 | 0.84 |
| Upper 90% CL | 1.06 | 1.05 |
| AUC (0-36 h) | | |
| Estimate of Ratio | 0.92 | 0.88 |
| Lower 90% CL | 0.82 | 0.78 |
| Upper 90% CL | 1.03 | 0.99 |
| $C_{max}$ | | |
| Estimate of Ratio | 0.49 | 0.38 |
| Lower 90% CL | 0.36 | 0.28 |
| Upper 90% CL | 0.66 | 0.53 |
| $t_{max}$ | | |
| Estimate of Ratio | 2.63 | 2.75 |
| Lower 90% CL | | |
| Upper 90% CL | | |
| MRT | | |
| Estimate of Ratio | 2.17 | 2.76 |
| Lower 90% CL | 1.71 | 2.11 |
| Upper 90% CL | 2.75 | 3.55 |

Trial ID.: Egalet CL-EG-pilot-02
CL: Confidence limit
'inf' means 'infinity'
Response in ANOVA model is the logarithm of the parameter in question.
Explanatory variables in ANOVA are Treatment (fixed) Period (fixed) and Pt.Id (random)
Estimated ratio is the antilog of the contrast between the two treatments
For $t_{max}$ the Hodges-Lehmann estimate of median difference is shown. No CLs are calculated.

TABLE 8

Least Square Geometric Mean for each Treatment for Pharmacokinetic Parameters from CarR(+) Profiles

| | 6.0 mm Egalet | 7.5 mm Egalet | Carvedilol IR |
|---|---|---|---|
| AUC (0-inf) ((ng/ml) * h) | | | |
| Least Square Geometric Mean | 298.34 | 292.83 | 312.29 |
| Lower 95% CL | 243.84 | 238.64 | 255.24 |

TABLE 8-continued

: Least Square Geometric Mean for each Treatment for Pharmacokinetic Parameters from CarR(+) Profiles

|  | 6.0 mm Egalet | 7.5 mm Egalet | Carvedilol IR |
|---|---|---|---|
| Upper 95% CL | 365.02 | 359.32 | 382.09 |
| AUC (0-36 h) ((ng/ml * h)) | | | |
| Least Square Geometric Mean | 277.54 | 264.24 | 301.80 |
| Lower 95% CL | 226.26 | 214.65 | 245.97 |
| Upper 95% CL | 340.54 | 325.29 | 370.30 |
| $C_{max}$ (ng/ml) | | | |
| Least Square Geometric Mean | 33.81 | 26.54 | 69.23 |
| Lower 95% CL | 26.50 | 20.44 | 54.25 |
| Upper 95% CL | 43.14 | 34.45 | 88.34 |
| MRT (h) | | | |
| Least Square Geometric Mean | 11.82 | 15.05 | 5.46 |
| Lower 95% CL | 9.54 | 11.99 | 4.40 |
| Upper 95% CL | 14.65 | 18.89 | 6.76 |

Trial ID.: Egalet CL-EG-pilot-02
CL: Confidence Limit

TABLE 9

: Summary Statistics for each Treatment for Pharmacokinetic Parameters from CarS(−) Profiles

|  | 6.0 mm Egalet | 7.5 mm Egalet | Carvedilol IR |
|---|---|---|---|
| AUC (0-inf) ((ng/ml) * h) | | | |
| N | 7 | 6 | 7 |
| Mean | 146.49 | 139.24 | 138.66 |
| SD | 41.26 | 69.99 | 45.91 |
| Median | 150.37 | 129.67 | 119.96 |
| Geometric Mean | 141.71 | 123.97 | 132.96 |
| Min | 89.32 | 48.72 | 98.47 |
| Max | 220.34 | 258.56 | 225.59 |
| AUC (0-36 h) ((ng/ml) * h) | | | |
| N | 7 | 6 | 7 |
| Mean | 132.73 | 120.03 | 130.63 |
| SD | 37.89 | 56.42 | 43.84 |
| Median | 130.60 | 116.78 | 113.65 |
| Geometric Mean | 128.43 | 107.91 | 125.13 |
| Min | 85.10 | 43.00 | 88.35 |
| Max | 205.70 | 212.20 | 214.70 |
| $C_{max}$ (ng/ml) | | | |
| N | 7 | 6 | 7 |
| Mean | 14.07 | 10.37 | 30.56 |
| SD | 3.12 | 3.86 | 12.55 |
| Median | 15.30 | 11.75 | 28.60 |
| Geometric Mean | 13.73 | 9.67 | 28.82 |
| Min | 8.80 | 5.60 | 19.70 |
| Max | 17.30 | 15.00 | 57.00 |
| $t_{max}$ (h) | | | |
| N | 7 | 6 | 7 |
| Mean | 3.43 | 3.93 | 1.14 |
| SD | 1.40 | 0.41 | 0.63 |
| Median | 3.00 | 4.00 | 1.00 |
| Geometric Mean | 3.20 | 3.81 | 1.00 |
| Min | 2.00 | 3.00 | 0.50 |
| Max | 6.00 | 4.00 | 2.00 |
| MRT (h) | | | |
| N | 7 | 6 | 7 |
| Mean | 13.93 | 16.64 | 7.00 |
| SD | 3.65 | 4.02 | 2.83 |
| Median | 13.79 | 17.08 | 6.31 |
| Geometric Mean | 13.57 | 16.16 | 6.57 |

TABLE 9-continued

: Summary Statistics for each Treatment for Pharmacokinetic Parameters from CarS(−) Profiles

|  | 6.0 mm Egalet | 7.5 mm Egalet | Carvedilol IR |
|---|---|---|---|
| Min | 10.14 | 9.63 | 4.01 |
| Max | 21.28 | 21.75 | 12.48 |

Trial ID.: Egalet CL-EG-pilot-02
SD: Standard Deviation

TABLE 10

: Two pairwise Comparisons of Treatments for Pharmacokinetics from CarS(−) Profiles. Estimate of Ratio with corresponding 90% Confidence Interval

|  | 6.0 mm Egalet vs Carvedilol IR | 7.5 mm Egalet vs Carvedilol IR |
|---|---|---|
| AUC (0-inf) | | |
| Estimate of Ratio | 1.12 | 1.03 |
| Lower 90% CL | 0.97 | 0.88 |
| Upper 90% CL | 1.31 | 1.20 |
| AUC (0-36 h) | | |
| Estimate of Ratio | 1.09 | 0.93 |
| Lower 90% CL | 0.92 | 0.78 |
| Upper 90% CL | 1.29 | 1.11 |
| $C_{max}$ | | |
| Estimate of Ratio | 0.49 | 0.34 |
| Lower 90% CL | 0.36 | 0.25 |
| Upper 90% CL | 0.68 | 0.48 |
| $t_{max}$ | | |
| Estimate of Ratio | 2.25 | 2.25 |
| Lower 90% CL | | |
| Upper 90% CL | | |
| MRT | | |
| Estimate of Ratio | 2.13 | 2.53 |
| Lower 90% CL | 1.58 | 1.85 |
| Upper 90% CL | 2.86 | 3.45 |

Trial ID.: Egalet CL-EG-pilot-02
CL: Confidence limit
'inf' means 'infinity'
Response in ANOVA model is the logarithm of the parameter in question. Explanatory variables in ANOVA are Treatment (fixed) Period (fixed) and Pt.Id (random) Estimated ratio is the antilog of the contrast between the two treatments For $t_{max}$ the Hodges-Lehmann estimate of median difference is shown. No CLs are calculated.

TABLE 11

: Least Square Geometric Mean for each Treatment for Pharmacokinetic Parameters from CarS(−) Profiles

|  | 6.0 mm Egalet | 7.5 mm Egalet | Carvedilol IR |
|---|---|---|---|
| AUC (0-inf) ((ng/ml * h)) | | | |
| Least Square Geometric Mean | 142.50 | 130.22 | 126.77 |
| Lower 95% CL | 114.39 | 103.98 | 101.71 |
| Upper 95% CL | 177.50 | 163.07 | 157.91 |
| AUC (0-36 h) ((ng/ml * h)) | | | |
| Least Square Geometric Mean | 130.24 | 111.49 | 119.98 |
| Lower 95% CL | 105.08 | 89.37 | 96.80 |
| Upper 95% CL | 161.43 | 139.09 | 148.71 |
| $C_{max}$ (ng/ml) | | | |
| Least Square Geometric Mean | 13.96 | 9.72 | 28.22 |
| Lower 95% CL | 11.13 | 7.62 | 22.51 |
| Upper 95% CL | 17.50 | 12.40 | 35.38 |

TABLE 11-continued

: Least Square Geometric Mean for each Treatment for
Pharmacokinetic Parameters from CarS(−) Profiles

|  | 6.0 mm Egalet | 7.5 mm Egalet | Carvedilol IR |
|---|---|---|---|
| MRT (h) | | | |
| Least Square Geometric Mean | 13.73 | 16.30 | 6.45 |
| Lower 95% CL | 11.02 | 12.87 | 5.18 |
| Upper 95% CL | 17.11 | 20.65 | 8.04 |

Trial ID.: Egalet CL-EG-pilot-02
CL: Confidence Limit
'inf' means infinity
Least square geometric means are estimated in ANOVA model Response in ANOVA model is the logarithm of the parameter in question. Explanatory variables in ANOVA are Treatment (fixed) Period (fixed) and Pt.Id (random) NO entries for $t_{max}$ since $t_{max}$ has been analysed using non parametric methods

TABLE 12

: Comparisons of 6.0 mm Fasting vs Food for Pharmacokinetics from Carvedilol Profiles. Estimate of Ratio with corresponding 90% Confidence Interval

|  | 6.0 mm Egalet vs 6.0 mm Food |
|---|---|
| AUC (0-inf) | |
| Estimate of Ratio | 1.17 |
| Lower 90% CL | 0.92 |
| Upper 90% CL | 1.47 |
| AUC (0-36 h) | |
| Estimate of Ratio | 1.20 |
| Lower 90% CL | 0.94 |
| Upper 90% CL | 1.54 |
| $C_{max}$ | |
| Estimate of Ratio | 1.10 |
| Lower 90% CL | 0.79 |
| Upper 90% CL | 1.55 |
| $t_{max}$ | |
| Estimate of Ratio | 0.50 |
| Lower 90% CL | −1.00 |
| Upper 90% CL | 2.00 |
| MRT | |
| Estimate of Ratio | 0.91 |
| Lower 90% CL | 0.77 |
| Upper 90% CL | 1.07 |

Trial ID.: Egalet CL-EG-pilot-02
CL: Confidence limit
'inf' means 'infinity'
Response in ANOVA model is the logarithm of the parameter in question. Explanatory variables in ANOVA are Treatment (fixed) and Pt.Id (random) Estimated ratio is the antilog of the contrast between the two treatments For $t_{max}$ the Hodges-Lehmann estimate and corresponding CL of median difference are shown. Only data from 6.0 mm Egalet and 6.0 mm Food have been included in the analyses Example 7

Preparation of a Composition of Carvedilol—DSC Measurements

A composition according to the invention was made from the following:

| PEO 200,000 | 67% w/w |
|---|---|
| Carvedilol | 28% w/w |
| Citric acid | 5% w/w |

The composition was made according to the general process described herein.

All starting materials as well as a mixture of PEO 200,000 and citric acid was subject to differential scanning caliometry measurements (thermal measurement). The final composition was also investigated at time 0 and 1 month after storage at 25° C./60% RH and 40° C./70% RH. The results show that the substances are employed in crystalline form (carvedilol, PEO and citric acid). DSC has also shown that PEO+citric acid only has one peak indicating that citric acid is present on amorphous or dissolved form. Carvedilol when admixed with PEO and citric acid maintain at least some of its crystallinity FIG. 10 shows the DSC of carvedilol as starting material and a peak is observed corresponding to that carvedilol is employed in crystalline form.

FIG. 11 shows DSC's of compositions according to the invention. No peak is present for carvedilol indicating the carvedilol is present in amorphous form. Storage of the compositions as mentioned above for about 1 month did not show any substantial difference in the DSC pattern.

Example 8

Carvedilol Containing Composition According to the Invention (Batch 02-0152-042)

A composition having the following ingredients was prepared and coated with an ethylcellulose based coating according to the general method:

| PEO 200,000 LF | 60.6% w/w |
|---|---|
| Poloxamer (Lutrol ® F68) | 19.2% w/w |
| Carvedilol | 14.0% w/w |
| Potassium metabisulfite | 0.2% w/w |
| BHT (butylhydroxytoluene) | 0.5% w/w |
| Ortho-phosporic acid | 4.5% w/w |
| Potassium dihydrogen phosphate | 1.0% w/w |

A dissolution profile of the composition is given in FIG. 12.

The composition was subject to a clinical study single dose cross over study in 12 volunteers. The results from the study are shown in the following tables and in FIGS. 13-14.

TABLE 13

[R(+) Carvedilol] Summary of results for treatment comparison A v. B
(Prolonged release Egalet 6.8 mm: Fasted v. Post-food/n = 12) 25 mg

| | Arithmetic mean ± SD | |
|---|---|---|
| Variable | A | B |
| $AUC_{0-36}$ (ng/mL · h) | 169.17 ± 113.38 | 167.65 ± 95.70 |
| $AUC_{0-\infty}$ (ng/mL · h) | 182.80 ± 118.36 | 180.70 ± 101.29 |
| $C_{max}$ (ng/mL) | 19.32 ± 11.17 | 21.77 ± 12.27 |
| $t_{max}$ (h) | 3.00 ± 0.74 | 3.50 ± 1.57 |
| $t_{1/2}$ (h) | 6.37 ± 2.55 | 6.48 ± 3.91 |
| MRT (h) | 9.92 ± 2.91 | 10.81 ± 2.74 |
| $K_{el}$ (h$^{-1}$) | 0.138 ± 0.086 | 0.158 ± 0.109 |
| % Residual | 9.25 ± 7.94 | 7.40 ± 4.44 |

TABLE 14

[S(−)Carvedilol] Summary of results for treatment comparison A v. B
(Prolonged release Egalet 6.8 mm: Fasted v. Post-food/n = 12) 25 mg

| | Arithmetic mean ± SD | |
|---|---|---|
| Variable | A | B |
| $AUC_{0-36}$ (ng/mL · h) | 62.94 ± 36.36 | 56.68 ± 24.88 |
| $AUC_{0-\infty}$ (ng/mL · h) | 77.43 ± 44.96 | 75.46 ± 41.58 |
| $C_{max}$ (ng/mL) | 6.70 ± 2.32 | 7.58 ± 3.70 |
| $t_{max}$ (h) | 3.58 ± 1.08 | 4.25 ± 2.90 |
| $t_{1/2}$ (h) | 8.48 ± 5.28 | 12.22 ± 15.44 |
| MRT (h) | 12.88 ± 6.21 | 17.56 ± 15.81 |
| $K_{el}$ (h$^{-1}$) | 0.118 ± 0.074 | 0.140 ± 0.102 |
| % Residual | 18.68 ± 8.29 | 20.04 ± 14.56 |

TABLE 15

[R(+) Carvedilol] Summary of results for treatment comparison A v. C
(Prolonged release Egalet 6.8 mm v. Immediate release Eucardic tablet/
n = 12)

| | Arithmetic mean ± SD | |
|---|---|---|
| Variable | A | C |
| $AUC_{0-36}$ (n = 12) (ng/mL · h) | 169.17 ± 113.38 | 185.67 ± 121.05 |
| $AUC_{0-\infty}$ (n = 12) (ng/mL · h) | 182.80 ± 118.36 | 197.01 ± 125.33 |
| $C_{max}$ (n = 12) (ng/mL) | 19.32 ± 11.17 | 47.08 ± 31.55 |
| $t_{max}$ (n = 12) (h) | 3.00 ± 0.74 | 1.58 ± 1.36 |
| $t_{1/2}$ (n = 12) (h) | 6.37 ± 2.55 | 6.80 ± 7.13 |
| MRT (n = 12) (h) | 9.92 ± 2.91 | 7.01 ± 5.11 |
| $K_{el}$ (n = 12) (h$^{-1}$) | 0.138 ± 0.086 | 0.188 ± 0.117 |
| % Residual (n = 12) | 9.25 ± 7.94 | 6.40 ± 7.25 |

TABLE 16

[S(−) Carvedilol] Summary of results for treatment comparison A v. C
(Prolonged release Egalet 6.8 mm v. Immediate release Eucardic tablet/
n = 12)

| | Arithmetic mean ± SD | |
|---|---|---|
| Variable | A | C |
| $AUC_{0-36}$ (n = 12) (ng/mL · h) | 62.94 ± 36.36 | 66.25 ± 33.31 |
| $AUC_{0-\infty}$ (n = 12) (ng/mL · h) | 77.43 ± 44.96 | 73.73 ± 36.57 |
| $C_{max}$ (n = 12) (ng/mL) | 6.70 ± 2.32 | 18.32 ± 11.21 |
| $t_{max}$ (n = 12) (h) | 3.58 ± 1.08 | 1.38 ± 1.37 |
| $t_{1/2}$ (n = 12) (h) | 8.48 ± 5.28 | 5.21 ± 3.38 |
| MRT (n = 12) (h) | 12.88 ± 6.21 | 6.74 ± 3.69 |
| $K_{el}$ (n = 12) (h$^{-1}$) | 0.118 ± 0.074 | 0.176 ± 0.083 |
| % Residual (n = 12) | 18.68 ± 8.29 | 10.54 ± 3.74 |

TABLE 17

[Total Carvedilol] Summary of results for treatment comparison A v. C
(Prolonged release Egalet 6.8 mm v. Immediate release Eucardic tablet/
n = 12). 25 mg

| | Arithmetic mean ± SD | |
|---|---|---|
| Variable | A | C |
| $AUC_{0-36}$ (ng/mL · h) | 228.85 ± 144.51 | 252.02 ± 152.33 |
| $AUC_{0-\infty}$ (ng/mL · h) | 243.52 ± 151.91 | 261.02 ± 154.74 |
| $C_{max}$ (ng/mL) | 25.26 ± 13.66 | 64.70 ± 43.74 |
| $t_{max}$ (h) | 2.83 ± 0.94 | 1.42 ± 1.35 |
| $t_{1/2}$ (h) | 6.53 ± 2.28 | 5.18 ± 3.67 |
| MRT (h) | 9.94 ± 2.42 | 6.14 ± 3.30 |
| $K_{el}$ (h$^{-1}$) | 0.133 ± 0.095 | 0.204 ± 0.131 |
| % Residual | 6.82 ± 3.57 | 4.10 ± 4.17 |

TABLE 18

[Total Carvedilol] Summary of results for treatment comparison A v. B
(Prolonged release Egalet 6.8 mm: Fasted v. Post-food/n = 12)

| | Arithmetic mean ± SD | |
|---|---|---|
| Variable | A | B |
| $AUC_{0-36}$ (n = 12) (ng/mL · h) | 228.85 ± 144.51 | 222.93 ± 121.10 |
| $AUC_{0-\infty}$ (n = 12) (ng/mL · h) | 243.52 ± 151.91 | 234.84 ± 125.96 |
| $C_{max}$ (n = 12) (ng/mL) | 25.26 ± 13.66 | 29.51 ± 15.99 |
| $t_{max}$ (n = 12) (h) | 2.83 ± 0.94 | 4.08 ± 1.88 |
| $t_{1/2}$ (n = 12) (h) | 6.53 ± 2.28 | 6.00 ± 2.21 |
| MRT (n = 12) (h) | 9.94 ± 2.42 | 10.35 ± 2.19 |
| $K_{el}$ (n = 12) (h$^{-1}$) | 0.133 ± 0.095 | 0.137 ± 0.069 |
| % Residual (n = 12) | 6.82 ± 3.57 | 5.27 ± 2.31 |

Absorption calculated from plasma concentrations of a 25 mg carvedilol controlled release formulation versus a 25 mg immediate release formulation in a single dose study (n=12) and are also disclosed in Tables 15-17.

TABLE 19

| | Total Carvedilol | | S(−) Carvedilol | | R(+) Carvedilol | |
|---|---|---|---|---|---|---|
| Abs. % | CR | IR | CR | IR | CR | IR |
| 50% | 115 min | 20 min | 115 min | 20 min | 115 min | 20 min |
| 80% | 265 min | 45 min | 286 min | 30 min | 275 min | 45 min |
| 90% | 380 min | 60 min | 410 min | 35 min | 390 min | 60 min |

The curves (FIGS. 15-17) are prepared from plasma concentrations on time points 0.5, 1, 2, 3, 4, 5, 6, 7, 8, 10, 12, 15, 18, 21, 24 30 and 36 hours after dosing and using a two compartment model fit of the plasma concentration where terminal elimination and volume distribution has been stripped from the curve leaving absorption rate as the residual. The software used is PCModFit by G. D. Allen Model-10-two-compartment oral, 2003.

It is observed that the differences for the controlled release formulation between the total carvedilol and the enantiomers are within 10%. The slower absorption of S(−) carvedilol from the IR formulation may be due to error induced by relative few plasma samples taken initially relative to the fast absorption.

Example 9

Carvedilol Containing Composition According to the Invention (Batch 02-0153-042)

A composition having the following ingredients was prepared according to the general description:

| | |
|---|---|
| PEO 200,000 LF | 61.3% w/w |
| Poloxamer (Lutrol ® F68) | 19.5% w/w |
| Carvedilol | 14.0% w/w |
| Potassium Metabisufite | 0.2% w/w |
| BHT (butylhydroxytoluene) | 0.5% w/w |
| Meta-phosporic acid | 4.5% w/w |

Example 10

Dissolution Duration and Dissolution Stability of Controlled Release Formulations

TABLE 20

Demonstrating stability and dissolution duration for formulations as disclosed in Examples 8 and 9 and comprising 25 mg carvedilol.

| rpm/pH | Stability Temp | Dissolition Time/min Zero order release | Comments Stability period Shape (length) of formulation |
|---|---|---|---|
| Composition Example 8 Batch | | | |
| 152 | | 380 | Baseline dissolution length 7.5 mm long shape |
| 152 | 50/6.8 | 390 | 3 month |
| 152 | 40 C. | 370 | 10 month stability |
| 49 | 25 C. | 333 | Baseline 6.8 mm long shape |
| 49 | 50/6.8 | | |
| 50 | 50/6.8 | 338 | Baseline 6.8 mm long shape |
| 50 | 50/6.8 25 C. | 343 | 4 month |
| 50 | 50/6.8 25 C. | 335 | 5 month |
| 52 | 50/6.8 | 330 | Baseline 6.8 mm long shape |
| 52 | 50/6.8 25 C. | 330 | 4 month |
| 61 | 50/6.8 | 325 | Baseline comprising TiO2 6.8 mm long shape |
| 71 | 50/6.8 | 338 | Baseline 6.8 mm long shape |
| Composition Example 9 Batch | | | |
| 153 | 50/6.8 | 375 | Baseline 7.5 mm long formulation |
| 153 | 50/6.8 30 C. | 373 | 3 month |
| 153 | 50/6.8 40 C. | 360 | 3 month |
| 153 | 50/6.8 30 C. | 360 | 10 month |

Example 11

Comparison of the Different Compositions and Clinical Studies Performed

TABLE 21

Arithmetic mean (SD not mentioned)
t = hours
C = ng/ml

| Study | mg | $T_{max}$ | $C_{max}$ | $T_{1/2}$ | MRT | $C_{12h}$ | $C_{24h}$ | $CIR_{max}/C_{max}$ (% of IR) | Ccalc | Diss Time |
|---|---|---|---|---|---|---|---|---|---|---|
| 2003 6.8 mm AUC relative 93% | 25 | 2.83 | 25.26 | 6.53 | 9.94 | 6.9 | 2.2 | 2.56 (39%) | 1 | *100%/338 min Zero order 2 h/35.5% 4 h/71% 50%/170 min 80%/270 min |
| 2003 6.8 mm S(−) | 25 | 3.58 | 6.7 | 8.48 | 12.88 | | | 2.7 (37%) | 0.27 | |
| 2003 6.8 mm R(+) | 25 | 3.00 | 19.32 | 6.37 | 9.92 | | | 2.44 (41%) | 0.77 | |
| 2000 12 mm AUC relative 53% Pilot III | 50 | 4 | 17.6 | | | | 3.8 | 2.75 (36%) | 0.35 | **100%/760 min Zero order 2 h/16% 4 h/32% 50%/380 min 80%/608 min |
| 2000 9 mm AUC relative 79% Pilot 111 | 37.5 | 4 | 15.8 | | | | 3.7 | 3 (33%) | 0.42 | **100%/508 min Zero order 2 h/24% 4 h/48% 50% 254 min 80%/406 min |
| 2000 6 mm | 25 | 4 | 16.3 | | | | 1.6 | 2.97 (34%) | 0.65 | **100%/254 min (estimated) |

TABLE 21-continued

Arithmetic mean (SD not mentioned)
t = hours
C = ng/ml

| Study | mg | $T_{max}$ | $C_{max}$ | $T_{1/2}$ | MRT | $C_{12h}$ | $C_{24h}$ | $CIR_{max}/C_{max}$ (% of IR) | Ccalc | Diss Time |
|---|---|---|---|---|---|---|---|---|---|---|
| AUC Relative 87% Pilot III | | | | | | | | | | Zero order |

*buffer media pH 6.8
**1 hour pH 1.0

The invention claimed is:

1. A controlled release pharmaceutical composition for oral use comprising:
   a solid dispersion of
   i) carvedilol at least partly in R(+) or S(−) form, wherein the carvedilol is at least partially present in amorphous form;
   ii) a polymer selected from the group consisting of
      (a) a polyethylene glycol and/or a polyethylene oxide each having a molecular weight of at least 20,000 daltons; and
      (b) a block copolymer of ethylene oxide and propylene oxide having a molecular weight of from 5,000 to 30,000 daltons;
   iii) a stabilizing agent comprising phosphoric acid or a pharmaceutically acceptable salt thereof; and
   a coating on the solid dispersion which is insoluble in and impermeable to body fluids;
   wherein said composition has improved stability shelf life.

2. A composition according to claim 1, wherein said carvedilol is in the form of the R(+) carvedilol.

3. A composition according to claim 1, wherein said carvedilol is in the form of the S(−) carvedilol.

4. The composition of claim 3, wherein said release of carvedilol from said composition after administration to a human results in a $t_{max}$ of S(−) carvedilol of from about 1.5 hour to about 8 hours.

5. A composition according to claim 1, wherein said composition is in the form of a matrix and said coating comprises a polymer and has at least one opening exposing at least one surface of said matrix.

6. A composition according to claim 1, wherein said carvedilol is selected from the group consisting of the racemate: (RS)-1-(9H-carbazol-4-yloxy)-3-[2-(2.methoxyphenoxy)-ethylaminopropan-2-ol, the two individual enantiomers: (S)-1-(9H-carbazol-4-yloxy)-3-[2-(2.methoxyphenoxy)-ethylaminopropan-2-ol and (R)-1-(9H-carbazol-4-yloxy)-3-[2-(2.methoxyphenoxy)-ethylaminopropan-2-ol, metabolites of carvedilol including desmethylcarvedilol, pharmaceutically acceptable salts, complexes, solvates and anhydrate thereof, and mixtures thereof.

7. A composition according to claim 1, wherein said carvedilol at least partially is present in solid form in the dispersion.

8. A composition according to claim 1, wherein said carvedilol at least partially is present in amorphous form with a mean particle size of from about 0.01 μm to about 500 μm.

9. A controlled release composition according to claim 1 wherein release of carvedilol from said composition after oral administration to a human results in an absorption of the carvedilol, wherein between 10% and 90% of the total carvedilol absorbed is absorbed within 2 hours from administration.

10. A controlled release composition according to claim 1 wherein release of carvedilol from said composition after oral administration to a human results in an absorption of the carvedilol, wherein between 30% and 95% of the total carvedilol absorbed is absorbed within 3 hours from administration.

11. A controlled release composition according to claim 1 wherein release of carvedilol from said composition after oral administration to a human results in an absorption of the carvedilol, wherein between 40% and 98% of the total carvedilol absorbed is absorbed within 4 hours from administration.

12. The composition of claim 1, wherein said release of carvedilol from said composition after administration to a human results in at $t_{max}$ of R(+) or S(−) carvedilol of from about 1.5 hour to about 8 hours.

13. A controlled release pharmaceutical composition for oral use comprising:
   a solid dispersion of
   i) carvedilol at least partly in R(+) or S(−) form, wherein the carvedilol is at least partially present in amorphous form;
   ii) a polymer selected from the group consisting of
      (a) a polyethylene glycol and/or a polyethylene oxide each having a molecular weight of at least 20,000 daltons and
      (b) a block copolymer of ethylene oxide and propylene oxide having a molecular weight of from 5,000 to 30,000 daltons;
   iii) a stabilizing agent comprising citric acid or a pharmaceutically acceptable salt thereof; and
   a coating on the solid dispersion which is insoluble in and impermeable to body fluids.

14. A composition according to claim 13, wherein said carvedilol is in the form of the R(+) carvedilol.

15. A composition according to claim 13, wherein said carvedilol is in the form of the S(−) carvedilol.

16. The composition of claim 15, wherein said release of carvedilol from said composition after administration to a human results in a $t_{max}$ of S(−) carvedilol of from about 1.5 hour to about 8 hours.

17. A composition according to claim 13, wherein said carvedilol is selected from the group consisting of the racemate: (RS)-1-(9H-carbazol-4-yloxy)-3-[2-(2.methoxyphenoxy)-ethylaminopropan-2-ol, the two individual enantiomers: (S)-1-(9H-carbazol-4-yloxy)-3-[2-(2.methoxyphenoxy)-ethylaminopropan-2-ol and (R)-1-(9H-carbazol-4-yloxy)-3-[2-(2.methoxyphenoxy)-ethylaminopropan-2-ol, metabolites of carvedilol including desmethylcarvedilol, pharmaceutically acceptable salts, complexes, solvates and anhydrate thereof, and mixtures thereof.

18. A composition according to claim 13, wherein said carvedilol at least partially is present in solid form in the dispersion.

19. A composition according to claim 13, wherein said carvedilol at least partially is present in amorphous form with a mean particle size of from about 0.01 µm to about 500 µm.

20. A controlled release composition according to claim 13, wherein release of carvedilol from said composition after oral administration to a human results in an absorption of the carvedilol, wherein between 10% and 90% of the total carvedilol absorbed is absorbed within 2 hours from administration.

21. A controlled release composition according to claim 13, wherein release of carvedilol from said composition after oral administration to a human results in an absorption of the carvedilol, wherein between 30% and 95% of the total carvedilol absorbed is absorbed within 3 hours from administration.

22. A controlled release composition according to claim 13, wherein release of carvedilol from said composition after oral administration to a human results in an absorption of the carvedilol, wherein between 40% and 98% of the total carvedilol absorbed is absorbed within 4 hours from administration.

23. The composition of claim 13, wherein said release of carvedilol from said composition after administration to a human results in at $t_{max}$ of R(+) or S(−) carvedilol of from about 1.5 hour to about 8 hours.

24. A controlled release pharmaceutical composition for oral use comprising:
   a) a solid dispersion comprising:
      i) carvedilol at least partly in R(+) or S(−) form and at least partially present in amorphous form, wherein the carvedilol is present in the solid dispersion in an amount of 14% w/w;
      ii) polyethylene oxide having a molecular weight of 200,000 daltons, wherein the polyethylene oxide is present in the solid dispersion in an amount of 60.6% w/w;
      iii) Poloxamer 188 present in the solid dispersion in an amount of 19.2% w/w;
      iv) a stabilizing agent comprising phosphoric acid present in the solid dispersion in an amount of 4.5% w/w; and
   b) a coating which is insoluble in and impermeable to body fluids.

25. The composition of claim 24, wherein the solid dispersion comprises an anti-oxidative agent comprising potassium metabisulfite.

26. The composition of claim 25, wherein the potassium metabisulfite is present in the solid dispersion in an amount of 0.2% w/w.

27. The composition of claim 24, wherein the solid dispersion comprises butylhydroxytoluene.

28. The composition of claim 27, wherein the butylhydroxytoluene is present in the solid dispersion in an amount of 0.5% w/w.

29. The composition of claim 24, wherein the solid dispersion comprises potassium dihydrogen phosphate.

30. The composition of claim 29, wherein the potassium dihydrogen phosphate is present in the solid dispersion in an amount of 1% w/w.

31. The composition of claim 24, wherein the solid dispersion comprises:
   an anti-oxidative agent comprising potassium metabisulfite in an amount of 0.2% w/w;
   butylhydroxytoluene in an amount of 0.5% w/w; and
   potassium dihydrogen phosphate in an amount of 1% w/w.

32. A controlled release pharmaceutical composition for oral use comprising:
   a) a solid dispersion comprising:
      i) carvedilol at least partly in R(+) or S(−) form and at least partially present in amorphous form, wherein the carvedilol is present in the solid dispersion in an amount of 14% w/w;
      ii) polyethylene oxide having a molecular weight of 200,000 daltons, wherein the polyethylene oxide is present in the solid dispersion in an amount of 60.6% w/w;
      iii) a stabilizing agent comprising phosphoric acid present in the solid dispersion in an amount of 4.5% w/w;
      iv) an anti-oxidative agent comprising potassium metabisulfite present in the solid dispersion in an amount of 0.2% w/w;
      v) butylhydroxytoluene present in the solid dispersion in an amount of 0.5% w/w;
      vi) potassium dihydrogen phosphate present in the solid dispersion in an amount of 1% w/w; and
      vii) a polaxamer; and
   b) a coating which is insoluble in and impermeable to body fluids.

* * * * *